US011485708B2

(12) United States Patent
Malathong et al.

(10) Patent No.: US 11,485,708 B2
(45) Date of Patent: Nov. 1, 2022

(54) COMPOUNDS FOR TREATMENT OF PD-L1 DISEASES

(71) Applicant: CHEMOCENTRYX, INC., Mountain View, CA (US)

(72) Inventors: Viengkham Malathong, Mountain View, CA (US); Pingchen Fan, Fremont, CA (US); Christopher Lange, El Cerrito, CA (US); Venkat Reddy Mali, Cupertino, CA (US); Darren J. McMurtrie, Sunnyvale, CA (US); Sreenivas Punna, Sunnyvale, CA (US); Howard S. Roth, Sunnyvale, CA (US); Rajinder Singh, Belmont, CA (US); Ju Yang, Palo Alto, CA (US); Penglie Zhang, Foster City, CA (US)

(73) Assignee: ChemoCentryx, Inc., San Carlos, CA (US)

(*) Notice: Subject to any disclaimer, the term of this patent is extended or adjusted under 35 U.S.C. 154(b) by 0 days.

(21) Appl. No.: 16/905,979

(22) Filed: Jun. 19, 2020

(65) Prior Publication Data

US 2021/0002229 A1 Jan. 7, 2021

Related U.S. Application Data

(60) Provisional application No. 62/864,002, filed on Jun. 20, 2019.

(51) Int. Cl.
| | | |
|---|---|---|
| *C07D 217/04* | (2006.01) |
| *A61K 45/06* | (2006.01) |
| *C07D 401/12* | (2006.01) |
| *A61K 31/4725* | (2006.01) |
| *C07C 217/58* | (2006.01) |
| *A61K 31/137* | (2006.01) |
| *C07D 211/58* | (2006.01) |
| *A61K 31/4468* | (2006.01) |
| *A61K 31/4545* | (2006.01) |
| *C07C 229/16* | (2006.01) |
| *A61K 31/197* | (2006.01) |
| *C07D 207/06* | (2006.01) |
| *A61K 31/40* | (2006.01) |
| *C07D 319/18* | (2006.01) |
| *A61K 31/357* | (2006.01) |
| *C07D 213/64* | (2006.01) |
| *A61K 31/4402* | (2006.01) |
| *C07D 215/227* | (2006.01) |
| *A61K 31/4704* | (2006.01) |
| *C07C 309/14* | (2006.01) |
| *A61K 31/185* | (2006.01) |
| *A61K 31/472* | (2006.01) |

(52) U.S. Cl.
CPC .......... *C07D 217/04* (2013.01); *A61K 31/137* (2013.01); *A61K 31/185* (2013.01); *A61K 31/197* (2013.01); *A61K 31/357* (2013.01); *A61K 31/40* (2013.01); *A61K 31/4402* (2013.01); *A61K 31/4468* (2013.01); *A61K 31/4545* (2013.01); *A61K 31/472* (2013.01); *A61K 31/4704* (2013.01); *A61K 31/4725* (2013.01); *A61K 45/06* (2013.01); *C07C 217/58* (2013.01); *C07C 229/16* (2013.01); *C07C 309/14* (2013.01); *C07D 207/06* (2013.01); *C07D 211/58* (2013.01); *C07D 213/64* (2013.01); *C07D 215/227* (2013.01); *C07D 319/18* (2013.01); *C07D 401/12* (2013.01)

(58) Field of Classification Search
CPC ................................... C07D 217/04
See application file for complete search history.

(56) References Cited

U.S. PATENT DOCUMENTS 10,654,815 B2   5/2020   Yang et al.
10,815,208 B2   10/2020  Feng et al.
(Continued)

FOREIGN PATENT DOCUMENTS

CN   108395443 A   8/2018
CN   108863963 A   11/2018
(Continued)

OTHER PUBLICATIONS

International Search Report and Written Opinion dated Sep. 14, 2020 corresponding to PCT/US2020/032904 filed May 14, 2020; 10 pages.

(Continued)

*Primary Examiner* — Golam M Shameem
(74) *Attorney, Agent, or Firm* — Mintz Levin Cohn Ferris Glovsky and Popeo PC

(57) ABSTRACT

Compounds are provided that are useful as immunomodulators. The compounds have the Formula (I)

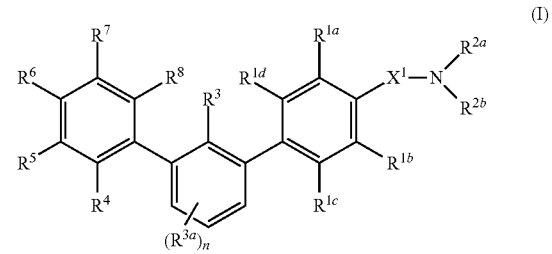

including stereoisomers and pharmaceutically acceptable salts thereof, wherein $R^{1a}$, $R^{1b}$, $R^{1c}$, $R^{1d}$, $R^{2a}$, $R^{2b}$, $R^3$, $R^{3a}$, $R^4$, $R^5$, $R^6$, $R^7$, $R^8$ and the subscript n are as defined herein. Methods associated with preparation and use of such compounds, as well as pharmaceutical compositions comprising such compounds, are also disclosed.

21 Claims, No Drawings

(56) References Cited

U.S. PATENT DOCUMENTS

| | | |
|---|---|---|
| 10,882,833 B2 | 1/2021 | Feng et al. |
| 10,941,129 B2 | 3/2021 | Feng et al. |
| 10,975,049 B2 | 4/2021 | Feng et al. |
| 2017/0107216 A1 | 4/2017 | Wu et al. |
| 2017/0145025 A1 | 5/2017 | Li et al. |
| 2017/0174679 A1 | 6/2017 | Lajkiewicz et al. |
| 2018/0177784 A1 | 6/2018 | Wu et al. |
| 2018/0264079 A1 | 9/2018 | Eike et al. |
| 2019/0308957 A1 | 10/2019 | Wang et al. |
| 2020/0383979 A1 | 12/2020 | Fan et al. |
| 2020/0392083 A1 | 12/2020 | Jiang et al. |
| 2021/0032270 A1 | 2/2021 | Yang et al. |

FOREIGN PATENT DOCUMENTS

| | | |
|---|---|---|
| CN | 109336857 A | 2/2019 |
| CN | 109438263 A | 3/2019 |
| CN | 109503546 A | 3/2019 |
| CN | 109665968 A | 4/2019 |
| CN | 109721527 A | 5/2019 |
| CN | 109776377 A | 5/2019 |
| CN | 109776445 A | 5/2019 |
| CN | 110128415 A | 8/2019 |
| CN | 110200959 A | 9/2019 |
| EP | 3 733 659 A1 | 11/2020 |
| WO | 2007/126957 A2 | 11/2007 |
| WO | 2007/126957 A3 | 11/2007 |
| WO | 2008/008059 A1 | 1/2008 |
| WO | 2015/033299 A1 | 3/2015 |
| WO | 2015/033301 A1 | 3/2015 |
| WO | 2015/034820 A1 | 3/2015 |
| WO | 2015/160641 A2 | 10/2015 |
| WO | 2015/160641 A3 | 10/2015 |
| WO | 2017/066227 A1 | 4/2017 |
| WO | 2017/070089 A1 | 4/2017 |
| WO | 2017/106634 A1 | 6/2017 |
| WO | 2017/112730 A1 | 6/2017 |
| WO | 2017/118762 A1 | 7/2017 |
| WO | 2017/192961 A1 | 11/2017 |
| WO | 2017/202273 A1 | 11/2017 |
| WO | 2017/202274 A1 | 11/2017 |
| WO | 2017/202275 A1 | 11/2017 |
| WO | 2017/202276 A1 | 11/2017 |
| WO | 2017/205464 A1 | 11/2017 |
| WO | 2017/222976 A1 | 12/2017 |
| WO | 2018/005374 A1 | 1/2018 |
| WO | 2018/006795 A1 | 1/2018 |
| WO | 2018/009505 A1 | 1/2018 |
| WO | 2018/013789 A1 | 1/2018 |
| WO | 2018/044783 A1 | 3/2018 |
| WO | 2018/044963 A1 | 3/2018 |
| WO | 2018/045142 A1 | 3/2018 |
| WO | 2018/118848 A1 | 6/2018 |
| WO | 2018/119221 A1 | 6/2018 |
| WO | 2018/119224 A1 | 6/2018 |
| WO | 2018/119236 A1 | 6/2018 |
| WO | 2018/119263 A1 | 6/2018 |
| WO | 2018/119266 A1 | 6/2018 |
| WO | 2018/119286 A1 | 6/2018 |
| WO | 2018/121560 A1 | 7/2018 |
| WO | 2018/183171 A1 | 10/2018 |
| WO | 2018/195321 A1 | 10/2018 |
| WO | 2018/196768 A1 | 11/2018 |
| WO | 2019/034172 A1 | 2/2019 |
| WO | 2019/070643 A1 | 4/2019 |
| WO | 2019/076343 A1 | 4/2019 |
| WO | 2019/087214 A1 | 5/2019 |
| WO | 2019/120297 A1 | 6/2019 |
| WO | 2019/128918 A1 | 7/2019 |
| WO | 2019/147662 A1 | 8/2019 |
| WO | 2019/149183 A1 | 8/2019 |
| WO | 2019/160882 A1 | 8/2019 |
| WO | 2019/169123 A1 | 9/2019 |
| WO | 2019/174533 A1 | 9/2019 |
| WO | 2019/175897 A1 | 9/2019 |
| WO | 2019/191707 A1 | 10/2019 |
| WO | 2019/192506 A1 | 10/2019 |
| WO | 2019/204609 A1 | 10/2019 |
| WO | 2019/217821 A1 | 11/2019 |
| WO | 2020/011209 A1 | 1/2020 |
| WO | 2020/011243 A1 | 1/2020 |
| WO | 2020/014643 A1 | 1/2020 |
| WO | 2020/015716 A1 | 1/2020 |
| WO | 2020/015717 A1 | 1/2020 |
| WO | 2020/025030 A1 | 2/2020 |

OTHER PUBLICATIONS

International Search Report dated Feb. 9, 2021 corresponding to PCT/US2020/055669 filed Oct. 15, 2020; 12 pages.

International Search Report dated Feb. 9, 2021 corresponding to PCT/US2020/055672 filed Oct. 15, 2020; 11 pages.

International Search Report dated Feb. 12, 2021 corresponding to PCT/US2020/038586 filed Jun. 19, 2020; 11 pages.

Patrick, Donald A. et al., "Synthesis and Antiprotozoal Activity of Dicationic m. Terphenyl and 1,3-Dipyridylbenzene Derivatives," *J. Med. Chem.* (Jun. 24, 2013) 56:5473-5494.

PUBMED-CID: 101577998 Create Date: Dec. 18, 2015; pp. 1-7; p. 2, structure; 7 pages.

Harvey, R.D., "Immunologic and Clinical Effects of Targeting PD-1 in Lung Cancer," *Clinical Pharmacology & Therapeutics* (Aug. 2014; advance online publication May 7, 2014) 96(2):214-233.

Jin, Hyun-Tak et al. "Role of PD-1 in Regulating T-Cell Immunity," *Current Topics in Microbiology and Immunoloty 350*, DOI 10.1007/82_2010_116 (© Springer-Verlag Berlin Heidelberg 2011; published online Sep. 11, 2010) 21 pages.

COMPOUNDS FOR TREATMENT OF PD-L1 DISEASES

CROSS-REFERENCES TO RELATED APPLICATIONS

This application is an application claiming benefit under 35 U.S.C. § 119(e) of U.S. Provisional Application No. 62/864,002 filed Jun. 20, 2019, which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE DISCLOSURE

Programmed cell death protein-1 (PD-1) is a member of the CD28 superfamily that delivers negative signals upon interaction with its two ligands, PD-L1 or PD-L2. PD-1 and its ligands are broadly expressed and exert a wide range of immunoregulatory roles in T cell activation and tolerance. PD-1 and its ligands are involved in attenuating infectious immunity and tumor immunity, and facilitating chronic infection and tumor progression.

Modulation of the PD-1 pathway has therapeutic potential in various human diseases (Hyun-Tak Jin et al., *Curr Top Microbiol Immunol*. (2011); 350:17-37). Blockade of the PD-1 pathway has become an attractive target in cancer therapy. Therapeutic antibodies that block the programmed cell death protein-1 (PD-1) immune checkpoint pathway prevent T-cell downregulation and promote immune responses against cancer. Several PD-1 pathway inhibitors have shown robust activity in various phases of clinical trials (R D Harvey, *Clinical Pharmacology and Therapeutics* (2014); 96(2), 214-223).

Agents that block the interaction of PD-L1 with either PD-1 or CD80 are desired. Some antibodies have been developed and commercialized. A few patent applications disclosing non-peptidic small molecules have been published (WO 2015/160641, WO 2015/034820, and WO 2017/066227 and WO2018/009505 from Bristol-Myers Squibb; WO 2015/033299 and WO 2015/033301 from Aurigene; WO 2017/070089, US 2017/0145025, WO 2017/106634, US2017/0174679, WO2017/192961, WO2017/222976, WO2017/205464, WO2017/112730, WO2017/041899 and WO2018/013789 from Incyte, WO2018/006795 from Maxinovel and WO2018/005374 from us, ChemoCentryx). However there is still a need for alternative compounds such as small molecules as inhibitors of PD-L1, and which may have advantageous characteristics in term of oral administration, stability, bioavailability, therapeutic index, and toxicity.

BRIEF SUMMARY OF THE DISCLOSURE

In one aspect, provided herein are compounds having formula (I):

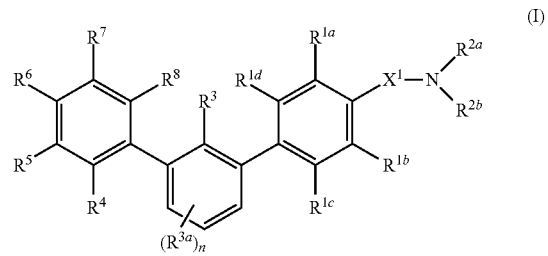

or a pharmaceutically acceptable salt thereof, or a prodrug or bioisostere thereof, wherein $R^{1a}$, $R^{1b}$, $R^{1c}$, $R^{1d}$, $R^{2a}$, $R^{2b}$, $R^3$, $R^{3a}$, $R^4$, $R^5$, $R^6$, $R^7$, $R^8$ and the subscript n are as defined herein.

In addition to the compounds provided herein, the present disclosure further provides pharmaceutical compositions containing one or more of these compounds, as well as methods associated with preparation and use of such compounds. In some embodiments, the compounds are used in therapeutic methods to treat diseases associated with the PD-1/PD-L1 pathway.

BRIEF DESCRIPTION OF THE DRAWINGS

Not Applicable

DETAILED DESCRIPTION OF THE DISCLOSURE

Abbreviation and Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "alkyl", by itself or as part of another substituent, means, unless otherwise stated, a straight or branched chain hydrocarbon group, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of alkenyl groups include vinyl, 2-propenyl, crotyl, 2-isopentenyl, 2-(butadienyl), 2,4-pentadienyl and 3-(1,4-pentadienyl). Examples of alkynyl groups include ethynyl, 1- and 3-propynyl, 3-butynyl, and the higher homologs and isomers.

The term "cycloalkyl" refers to a hydrocarbon ring or rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The bicyclic or polycyclic rings may be fused, bridged, spiro or a combination thereof.

The term "heterocycloalkyl" or "heterocyclyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. The bicyclic or polycyclic rings may be fused, bridged, spiro or a combination thereof. It is understood that the recitation '$C_{4-12}$ heterocyclyl', for example, refers to a group having from 4 to 12 ring members where at least one of the ring members is a heteroatom. Non limiting examples of heterocycloalkyl groups include pyrrolidine, imidazolidine, pyrazolidine, butyrolactam, valerolactam, imidazolidinone, tetrazolone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "alkylene" by itself or as part of another substituent means a divalent group derived from an alkane, as exemplified by —$CH_2CH_2CH_2CH_2$—. An alkylene group can be linear or branched. An examples of the latter are —$CH_2C(CH_3)_2CH_2$—, —$CH_2C(CH_3)_2$— or —$CH(CH_3)CH_2CH_2$—. Typically, an alkyl (or alkylene) group will have from 1 to 12 carbon atoms, with those groups having 8 or fewer carbon atoms being preferred in the present disclosure. Similarly, "alkenylene" and "alkynylene" refer to the unsaturated forms of "alkylene" having double or triple bonds, respectively.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, 2,2,2-trifluoroethyl, 4-chlorobutyl, 3-bromopropyl, and the like.

The term "hydroxyalkyl" or "alkyl-OH" refers to an alkyl group, as defined above, where at least one (and up to three) of the hydrogen atoms is replaced with a hydroxy group. As for the alkyl group, hydroxyalkyl groups can have any suitable number of carbon atoms, such as $C_{1-6}$. Exemplary hydroxyalkyl groups include, but are not limited to, hydroxymethyl, hydroxyethyl (where the hydroxy is in the 1- or 2-position), hydroxypropyl (where the hydroxy is in the 1-, 2- or 3-position), and 2,3-dihydroxypropyl.

The term "aryl" means, unless otherwise stated, a polyunsaturated, typically aromatic, hydrocarbon group which can be a single ring or multiple rings (up to three rings) which are fused together or linked covalently.

The term "heteroaryl" refers to a five- to ten-membered aromatic ring (or rings) that have from one to five heteroatom ring vertices, each of which is selected from N, O, and S, wherein the nitrogen and sulfur atoms are optionally oxidized, and the nitrogen atom(s) are optionally quaternized. A heteroaryl group can be attached to the remainder of the molecule through a heteroatom. It is understood that the recitation '$C_{5-10}$ heteroaryl', refers to a heteroaryl moiety having from 5 to 10 ring members where at least one of the ring members is a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

When any of the above terms (e.g., "alkyl," "aryl" and "heteroaryl") are referred to as 'substituted' without further notation on the substituents, the substituted forms of the indicated group will be as provided below.

Substituents for the alkyl groups (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —$CO_2$R', —CONR'R", —OC(O)NR'R", —NR"C(O)R', —NR'—C(O)NR'R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —$NO_2$ in a number ranging from zero to (2 m'+1), where m' is the total number of carbon atoms in such group. R', R" and R'" each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl group wherein two substitutents on the carbon that is closest to the point of attachment for the group is replaced with the substitutent =O (e.g., —C(O)CH$_3$, —C(O)CH$_2$CH$_2$OR' and the like).

Similarly, substituents for the aryl and heteroaryl groups are varied and are generally selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR'R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —$N_3$, perfluoro($C_1$-$C_4$)alkoxy, and perfluoro($C_1$-

$C_4$)alkyl, in a number ranging from zero to the total number of open valences on the aromatic ring system; and where R', R" and R'" are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si). Within a ring system, heteroatoms at ring vertices include N, O and S.

The disclosure herein further relates to prodrugs and bioisosteres thereof. Suitable bioisosteres, for example, will include carboxylate replacements (phosphonic acids, phosphinic acids, sulfonic acids, sulfinic acids, and acidic heterocyclic groups such as tetrazoles). Suitable prodrugs will include those conventional groups known to hydrolyze and/or oxidize under physiological conditions to provide a compound of Formula I.

The terms "patient" and "subject" include primates (especially humans), domesticated companion animals (such as dogs, cats, horses, and the like) and livestock (such as cattle, pigs, sheep, and the like).

As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms).

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer to the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are intended to be encompassed within the scope of the present disclosure. For example, the compounds may be prepared such that any number of hydrogen atoms are replaced with a deuterium ($^2$H) isotope. The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure.

Compounds

In one aspect, the present disclosure provides compounds having formula (I):

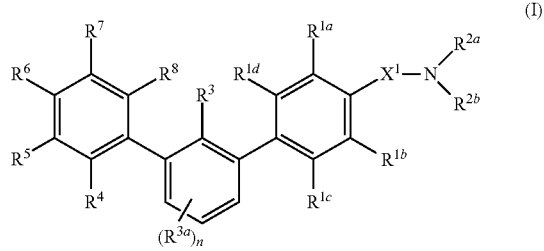

or a pharmaceutically acceptable salt thereof, or a prodrug or bioisostere thereof; wherein:
$R^{1a}$, $R^{1b}$, $R^{1c}$ and $R^{1d}$ are each independently selected from the group consisting of H, F, Cl, $C_{1-3}$ alkyl, $C_{1-3}$ haloalkyl, $C_{1-3}$ alkoxy and CN;
$X^1$ is $C_{1-3}$ alkylene, optionally substituted with one or two $C_{1-2}$ alkyl or $CO_2H$;
$R^{2a}$ and $R^{2b}$ are each independently selected from the group consisting of H, $C_{1-8}$ alkyl, $C_{1-8}$ haloalkyl, —Y, —$X^2$—$C(O)_2R^a$, —$X^2$—$OR^a$, —$X^2$—$NR^aR^b$, —$X^2$—$CONR^aR^b$, —$X^2$—$SO_2R^a$, —$X^2$—$SO_2NR^aR^b$, —$X^2$—$SO_3R^a$ and —$X^2$—Y wherein each $X^2$ is $C_{1-6}$ alkylene and any $C_{1-8}$ alkyl or $C_{1-6}$ alkylene, is optionally further substituted with one or two members independently selected from OH, $SO_2NH_2$, $CONH_2$, $C(O)NHOH$, $PO_3H_2$, COO—$C_{1-8}$alkyl or $CO_2H$, and each Y is selected from the group consisting of $C_{3-6}$ cycloalkyl, $C_{4-8}$ heterocyclyl and 5- to 6-membered heteroaryl, each of which is optionally further substituted with one to four substituents independently selected from the group consisting of oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, COO—$C_{1-8}$alkyl, and $CO_2H$;

or $R^{2a}$ and $R^{2b}$ are combined to form a 4- to 8-membered ring or spirocyclic ring, optionally having one or two additional ring vertices selected from O, N or S;
or $R^{1a}$ and $R^{2a}$ or $X^1$ are combined to form a 5- to 7-membered ring;
or $R^{1b}$ and $R^{2b}$ or $X^1$ are combined to form a 5- to 7-membered ring;
wherein the rings formed by combining $R^{2a}$ and $R^{2b}$, $R^{1a}$ and $R^{2a}$ or $X^1$, or $R^{1b}$ and $R^{2b}$ or $X^1$, are substituted with 0 to 4 substituents independently selected from the group consisting of oxo, $C_{1-8}$ alkyl, $C_{1-8}$ haloalkyl, —$X^3$—$C(O)_2R^a$, —$X^3$—$OR^a$, —$X^3$—$NR^aR^b$, —$X^3$—$CONR^aR^b$, —$X_3$—$SO_2R^a$, —$X^3$—$SO_2NR^aR^b$, and —$X^3$—$SO_3R^a$; wherein $X^3$ is a bond or $C_{1-6}$ alkylene;
$R^3$ is selected from the group consisting of H, F, Cl, $C_{1-3}$ alkyl, $C_{1-3}$ alkoxy, $C_{1-3}$ haloalkyl, $C_{1-3}$ haloalkoxy, $C_{2-3}$ alkenyl and CN;
the subscript n is 0, 1 or 2;
each $R^{3a}$ is independently selected from the group consisting of F, Cl, $C_{1-3}$ alkyl, $C_{1-3}$ alkoxy, $C_{1-3}$ haloalkyl, $C_{1-3}$ haloalkoxy, $C_{2-3}$ alkenyl and CN;
each of $R^4$, $R^6$, $R^7$ and $R^8$ is independently selected from the group consisting of H, halogen, CN, $C_{1-6}$ alkyl, $C_{2-6}$ alkenyl, $C_{2-6}$ alkynyl, $C_{1-6}$ haloalkyl, $C_{1-6}$ hydroxyalkyl, —$Y^1$, —$X^4$—$C(O)_2R^a$, —$X^4$—$OR^a$, —$X^4$—$NR^aR^b$, $X^4$—$CONR^aR^b$, —$X^4$—$SO_2R^a$, —$X^4$—$SO_2NR^aR^b$, —$X^4$—$SO_3R^a$, —O—$X^4$—$Y^1$ and —$X^4$—$Y^1$ wherein each $X^4$ is a bond or $C_{1-6}$ alkylene and is optionally further substituted with OH, $SO_2NH_2$, $CONH_2$, $C(O)NHOH$, $PO_3H_2$, COO—$C_{1-8}$alkyl or $CO_2H$, and each $Y^1$ is selected from the group consisting of $C_{3-6}$ cycloalkyl, $C_{4-8}$ heterocyclyl and 5- to 6-membered heteroaryl, each of which is optionally further substituted with one to four substituents independently selected from the group consisting of oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, COO—$C_{1-8}$alkyl, and $CO_2H$;
$R^5$ is a member selected from the group consisting of H, halogen, CN, $C_{1-6}$ alkyl, $C_{1-6}$ haloalkyl, $C_{1-6}$ hydroxyalkyl, —$Y^2$, —$X^5$—$C(O)_2R^a$, —$X^5$—$OR^a$, —$X^5$—$NR^aR^b$, —$X^5$—$CONR^aR^b$, —$X^5$—$SO_2R^a$, —$X^5$—$SO_2NR^aR^b$, —$X^5$—$SO_3R^a$, —$X^5$—$Y^2$, —O—$X^5$—$Y^2$ and -A-Z, wherein each $X^5$ is a bond or $C_{1-6}$ alkylene and is optionally further substituted with OH, $SO_2NH_2$, $CONH_2$, $C(O)NHOH$, $PO_3H_2$, COO—$C_{1-8}$alkyl or $CO_2H$, and each $Y^2$ is selected from the group consisting of $C_{3-6}$ cycloalkyl, $C_{4-8}$ heterocyclyl, $C_{7-9}$ spiroheterocyclyl, and 5- to 6-membered heteroaryl, each of which is optionally further substituted with one to four substituents independently selected from the group consisting of oxo, halogen, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, COO—$C_{1-8}$alkyl, and $CO_2H$;
wherein
A is a member selected from the group consisting of a bond, —O— and —$N(R^a)$—;
Z is selected from the group consisting of:
i) a monocyclic 5- or 6-membered heteroaryl ring, optionally substituted with one to three $R^c$;
ii) phenyl, optionally substituted with one to three $R^c$; and
iii) a 5- or 6-membered non-aromatic heterocyclic ring, optionally substituted with one to three $R^c$;
and when A is —O— or —$N(R^a)$—, then Z is other than phenyl;

and two of $R^4$, $R^5$, $R^6$, $R^7$ and $R^8$ on adjacent carbon atoms are optionally combined to form a 5- or 6-membered non-aromatic heterocyclic ring having one or two ring vertices selected from the group consisting of O, —N($R^b$)— and =N—; wherein said non-aromatic heterocyclic ring is optionally substituted with oxo and optionally with from one to four $R^c$;

and at least one of $R^4$, $R^5$, $R^6$, $R^7$ and $R^8$ is other than H;

each $R^a$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2$H, $C_{1-6}$ alkylene-COO—$C_{1-8}$alkyl, $C_{1-6}$ alkylene-$SO_3$H;

each $R^b$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2$H, $C_{1-6}$ alkylene-$SO_3$H and $C_{1-6}$ alkylene-$Y^3$, wherein $Y^3$ is $C_{3-6}$ cycloalkyl or $C_{4-8}$ heterocyclyl, and each $R^b$ is optionally further substituted with one or two members independently selected from oxo, OH, $SO_2NH_2$, $CONH_2$, C(O)NHOH, $PO_3H_2$, COO—$C_{1-8}$alkyl and $CO_2$H;

and $R^a$ and $R^b$, when attached to the same nitrogen atom, are optionally combined to form a 4- to 8-membered ring or spirocyclic ring, optionally substituted with halogen, OH, $SO_2NH_2$, $CONH_2$, C(O)NHOH, $PO_3H_2$, COO—$C_{1-8}$alkyl or $CO_2$H;

each $R^c$ is independently selected from the group consisting of H, halogen, CN, $C_{1-6}$ alkyl, $C_{1-6}$ haloalkyl, —$Y^4$, —$X^6$—C(O)$_2R^a$, —$X^6$—O$R^a$, —$X^6$—N$R^aR^b$, —$X^6$—CONR$^aR^b$, —$X^6$—SO$_2R^a$, —$X^6$—SO$_2$NR$^aR^b$, —$X^6$—SO$_3R^a$, and —N($R^a$)—$X^6$—C(O)$_2R^a$, wherein each $X^6$ is a bond or $C_{1-6}$ alkylene, and each $Y^4$ is selected from the group consisting of $C_{3-6}$ cycloalkyl and $C_{4-8}$ heterocyclyl; and optionally two $R^c$ on adjacent ring vertices are combined to form a fused 5- or 6-membered heterocyclic ring.

In some embodiments, the present disclosure provides compounds having the formula formula (Ia):

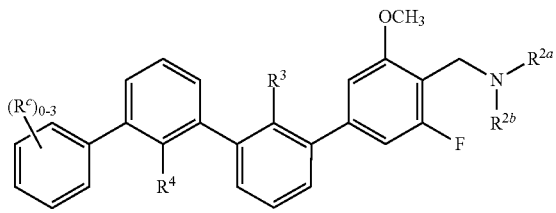

(Ia)

wherein $R^{2a}$, $R^{2b}$, $R^3$, $R^4$, and $R^c$, are as defined for formula (I).

In some embodiments, the present disclosure provides compounds having the formula formula (Ib):

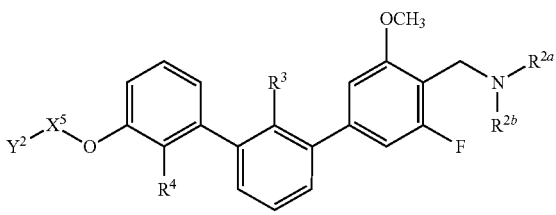

(Ib)

wherein $R^{2a}$, $R^{2b}$, $R^3$, $R^4$, $X^5$ and $Y^2$ are as defined for formula (I). In some selected embodiments, compounds of formula (Ib) are provided wherein $Y^2$ is selected from the group consisting of:

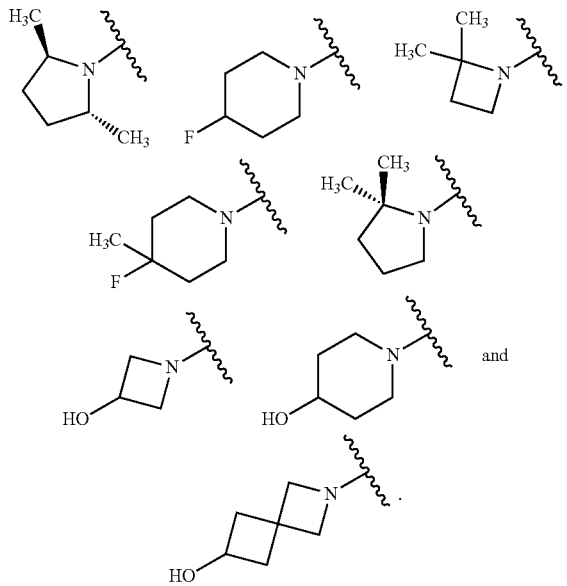

In some embodiments, the present disclosure provides compounds having the formula formula (Ic):

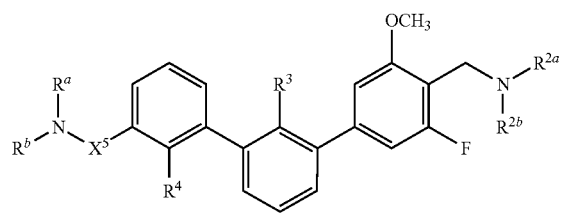

(Ic)

wherein $R^{2a}$, $R^{2b}$, $R^3$, $R^4$, $R^a$, $R^b$ and $X^5$ are as defined for formula (I).

In some selected embodiments, the compounds of formula (I), are those compounds wherein $R^5$ is -A-Z.

In some selected embodiments, the compounds of formula (I), are those compounds wherein $R^5$ is —O—$X^5$—$Y^2$.

In some selected embodiments, the compounds of formula (I), are those compounds wherein $R^5$ is -A-Z, A is a bond, and Z is phenyl, optionally substituted with one to three $R^c$.

In some selected embodiments, the compounds of formula (I), are those compounds wherein $X^1$ is —$CH_2$—.

In some selected embodiments, the compounds of formula (I), are those compounds wherein $R^{1c}$, $R^7$ and $R^8$ are H, and $R^3$ is selected from the group consisting of F, Cl, $CH_3$, $CF_3$ and $OCH_3$.

In some selected embodiments, the compounds of formula (I), are those wherein a ring is formed between one pair of $R^4$ and $R^5$, $R^5$ and $R^6$, $R^{1b}$ and $R^{2b}$, or $R^{1a}$ and $R^{2a}$.

In some selected embodiments, the compounds of formula (I), are those compounds wherein $R^5$ is -A-Z, and Z is selected from the group consisting of piperidinyl, imidazolyl and pyridinyl.

In some selected embodiments, the compounds of formula (I), are those compounds wherein n is 0.

In some selected embodiments, the compounds of formula (I), are those compounds wherein $R^4$ is selected from the group consisting of F, Cl, $CH_3$, $CF_3$ and $OCH_3$.

In some selected embodiments, the compounds of formula (I), are those compounds wherein $R^{1a}$ is $OCH_3$ and $R^{1b}$ is F.

In some selected embodiments, the compounds of formula (I), are those compounds wherein $R^{2a}$ and $R^{2b}$ are each H.

In some selected embodiments, the compounds of formula (I), are those compounds wherein $R^{2a}$ and $R^{2b}$ are combined to form a 4- to 8-membered ring or spirocyclic ring, optionally having one or two additional ring vertices selected from O, N or S; wherein said ring or spirocyclic ring is substituted with 0 to 4 substituents independently selected from the group consisting of oxo, $C_{1-8}$ alkyl, $C_{1-8}$ haloalkyl, $C_{1-8}$hydroxyalkyl, $—X^2—C(O)_2R^a$, $—X^2—OR^a$, $—X^2—NR^aR^b$, $—X^2—CONR^aR^b$, $—X^2—SO_2R^a$, $—X^2—SO_2NR^aR^b$, and $—X^2—SO_3R^a$; wherein $X^2$ is a bond or $C_{1-6}$ alkylene.

In some selected embodiments, the compounds of formula (I), are those compounds wherein $R^{2a}$ is H or $C_{1-8}$ alkyl; and $R^{2b}$ is $—Y$ or $—X^1—Y$. In further selected embodiments, Y is selected from the group consisting of $C_{3-6}$ cycloalkyl and $C_{4-8}$ heterocyclyl, each of which is optionally further substituted with one to four substituents independently selected from the group consisting of oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO—C_{1-8}$alkyl, and $CO_2H$.

In some embodiments, for each of formula (I), (Ia), (Ib) and (Ic), and the further selected embodiments above, the compounds or a pharmaceutically acceptable salt thereof, are those selected from Table 1, having ++ or +++ activity.

In addition to the compounds provided above, pharmaceutically acceptable salts of those compounds are also provided. In some embodiments, the pharmaceutically acceptable salts are selected from ammonium, calcium, magnesium, potassium, sodium, zinc, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, procaine, purines, theobromine, triethylamine, trimethylamine, tripropylamine, tromethamine, hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids. In some embodiments, the pharmaceutically acceptable salts are selected from ammonium, calcium, magnesium, potassium, sodium, hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids. In some embodiments, the pharmaceutically acceptable salts are sodium or hydrochloric.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

An ester may be used as a prodrug for the corresponding carboxylic acid. A $C_{1-10}$ alkyl ester or a $C_{1-10}$ haloalkyl ester may be used as a prodrug for the corresponding carboxylic acid. The following esters may be used: tert-butyl ester, methyl ester, ethyl ester, isopropyl ester.

Pharmaceutical Compositions

In addition to the compounds provided herein, compositions of those compounds will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In another embodiment, a pharmaceutical composition comprising a compound of the present disclosure including a compound of Formulae (I), (Ia), (Ib), (Ic) or (Id), or a pharmaceutically acceptable salt thereof, and a pharmaceutically acceptable excipient, is provided.

In some embodiments, the pharmaceutical composition further comprises one or more additional therapeutic agents. In some embodiments, the one or more additional therapeutic agent is selected from the group consisting of an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. In some embodiments, the one or more additional therapeutic agent is an antagonist of a chemokine and/or chemoattractant receptor, which includes but is not limited to, CCR1, CCR2, CCR3, CCR4, CCR5, CCR6, CCR7, CCR8, CCR9, CCR10, CCR11, CCR12, CXCR1, CXCR2, CXCR3, CXCR4, CXCR5, CXCR6, CXCR7, C3aR, and/or C5aR. Chemokine and/or chemoattractant receptor antagonists are known in the art and described in, for example, WO2007/002667, WO2007/002293, WO/2003/105853, WO/2007/022257, WO/2007/059108, WO/2007/044804, WO2007/115232, WO2007/115231, WO2008/147815, WO2010/030815, WO2010/075257, WO2011/163640, WO2010/054006, WO2010/051561, WO2011/035332, WO2013/082490, WO2013/082429, WO2014/085490, WO2014/100735, WO2014/089495, WO2015/084842, WO2016/187393, WO2017/127409, WO 2017/087607, WO2017/087610, WO2017/176620, WO2018/222598, WO2018/222601, WO2013/130811, WO2006/076644, WO2008/008431, WO2009/038847, WO2008/008375, WO2008/008374, WO2008/010934, WO2009/009740, WO2005/112925, WO2005/112916, WO2005/113513, WO2004/085384, WO2004/046092. Chemokine and/or chemoattractant receptor antagonists also include CCX354, CCX9588, CCX140, CCX872, CCX598, CCX6239, CCX9664, CCX2553, CCX3587, CCX3624, CCX 2991, CCX282, CCX025, CCX507, CCX430, CCX765, CCX224, CCX662, CCX650, CCX832, CCX168, CCX168-M1, CCX3022 and/or CCX3384.

The pharmaceutical compositions for the administration of the compounds of this disclosure may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, anti-oxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, polyethylene glycol (PEG) of various average sizes (e.g., PEG400, PEG4000) and certain surfactants such as cremophor or solutol, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono- or di-glycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present disclosure are employed. As used herein, topical application is also meant to include the use of mouth washes and gargles.

The compounds of this disclosure may also be coupled with a carrier that is a suitable polymer for targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the disclosure may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the disclosure, the compound of the disclosure is coupled to a polymer or semipermeable polymer matrix that is formed as a stent or stent-graft device.

Methods of Treating Diseases and Disorders

The compounds of the disclosure may be used as immunomodulators. The compounds of the disclosure may be used as agonists, antagonists, partial agonists, inverse agonists, inhibitors of PD-1 and/or PD-L1 in a variety of contexts, both in vitro and in vivo. In some embodiments, the compounds of the disclosure may be used as inhibitors of the PD-1/PD-L1 protein protein interaction. In some embodiments, the compounds of the disclosure may be used as inhibitors of PD-L1. In some embodiments, the compounds of the disclosure may be used as inhibitors of the CD80/PD-L1 protein protein interaction. In some embodiments, the compounds of the disclosure may be used to inhibit the interaction between PD-1 and PD-L1 and/or PD-1 and CD80 and/or PD-L1 and PD-L2 in vitro or in vivo. In some embodiments, the compounds of the disclosure may be used to inhibit VISTA and/or TIM-3. In some embodiments, the compounds of the disclosure may be inhibitors of the PD-1/PD-L1 protein protein interaction and inhibitors of VISTA and/or TIM-3. In some embodiments, in addition to being inhibitors of the PD-1/PD-L1 protein protein interaction, the compounds of the disclosure may be inhibitors of CTLA-4 and/or BTLA and/or LAG-3 and/or KLRG-1 and/or 2B4 and/or CD160 and/or HVEM and/or CD48 and/or E-cadherin and/or MHC-II and/or galectin-9 and/or CD86 and/or PD-L2 and/or VISTA and/or TIM-3 and/or CD80.

The compounds of the disclosure may be contacted with the receptor they interact with, in aqueous solution and under conditions otherwise suitable for binding of the ligand to the receptor. The receptor may be present in suspension (e.g., in an isolated membrane or cell preparation), in a cultured or isolated cell, or in a tissue or organ.

Preferably, the amount of the compounds of the disclosure contacted with the receptor should be sufficient to inhibit the PD-1/PD-L1 binding in vitro as measured, for example, using an ELISA. The receptor may be present in solution or suspension, in a cultured or isolated cell preparation or within a patient.

In some embodiments, the compounds of the present disclosure are useful for restoring and augmenting T cell activation. In some embodiments, the compounds of the present disclosure are useful for enhancing an immune response in a patient. In some embodiments, the compounds of the present disclosure are useful for treating, preventing, or slowing the progression of diseases or disorders in a variety of therapeutic areas, such as cancer and infectious diseases.

In some embodiments, the compounds of the present disclosure can be used for treating patients suffering from conditions that are responsive to PD-1/PD-L1 protein protein interaction modulation.

In some embodiments, a method of modulating an immune response mediated by the PD-1 signaling pathway in a subject, comprising administering to the subject a therapeutically effective amount of a compound of the present disclosure including a compound of Formulae (I), (Ia), (Ib), (Ic) or (Id), or a pharmaceutically acceptable salt thereof or a composition comprising a compound of Formulae (I), (Ia), (Ib), (Ic) or (Id), or a pharmaceutically acceptable salt thereof, is provided.

In some embodiments, a method of enhancing, stimulating, modulating and/or increasing the immune response in a subject in need thereof, comprising administering to the subject a therapeutically effective amount of a compound of the present disclosure including a compound of Formulae (I), (Ia), (Ib), (Ic) or (Id), or a pharmaceutically acceptable salt thereof or a composition of a compound of the present disclosure including a compound of Formula (I), (Ta), (Ib), (II), (IIa), or (IIb), or a pharmaceutically acceptable salt thereof, is provided.

In some embodiments, a method of inhibiting growth, proliferation, or metastasis of cancer cells in a subject in need thereof, comprising administering to the subject a therapeutically effective amount of a compound of the present disclosure including a compound of Formula (I), (Ta), (Ib), (Ic), or (Id), or a pharmaceutically acceptable salt thereof or a composition of a compound of the present disclosure including a compound of Formula (I), (Ta), (Ib), (Ic), or (Id), or a pharmaceutically acceptable salt thereof, is provided.

In some embodiments, a method of treating a subject in need thereof, comprising administering to the subject a therapeutically effective amount of a compound of the present disclosure including a compound of Formulae (I), (Ia), (Ib), (Ic) or (Id), or a pharmaceutically acceptable salt thereof or a composition of a compound of the present disclosure including a compound of Formulae (I), (Ia), (Tb), (Ic) or (Id), or a pharmaceutically acceptable salt thereof, is provided.

In some embodiments, the subject suffers from a disease or disorder selected from the group consisting of an infectious disease, a bacterial infectious disease, a viral infectious disease a fungal infectious disease, a solid tumor, a hematological malignancy, an immune disorder, an inflammatory disease, and cancer. In some embodiments, the disease or disorder is selected from the group consisting of melanoma, glioblastoma, esophagus tumor, nasopharyngeal carcinoma, uveal melanoma, lymphoma, lymphocytic lymphoma, primary CNS lymphoma, T-cell lymphoma, diffuse large B-cell lymphoma, primary mediastinal large B-cell lymphoma, prostate cancer, castration-resistant prostate cancer, chronic myelocytic leukemia, Kaposi's sarcoma fibrosarcoma, liposarcoma, chondrosarcoma, osteogenic sarcoma, angiosarcoma, lymphangiosarcoma, synovioma, meningioma, leiomyosarcoma, rhabdomyosarcoma, sarcoma of soft tissue, sarcoma, sepsis, biliary tumor, basal cell carcinoma, thymus neoplasm, cancer of the thyroid gland, cancer of the parathyroid gland, uterine cancer, cancer of the adrenal gland, liver infection, Merkel cell carcinoma, nerve tumor, follicle center lymphoma, colon cancer, Hodgkin's disease, non-Hodgkin's lymphoma, leukemia, chronic or acute leukemias including acute myeloid leukemia, chronic myeloid leukemia, acute lymphoblastic leukemia, chronic lymphocytic leukemia, multiple myeloma, ovary tumor, myelodysplastic syndrome, cutaneous or intraocular malignant melanoma, renal cell carcinoma, small-cell lung cancer, lung cancer, mesothelioma, breast cancer, squamous non-small cell lung cancer (SCLC), non-squamous NSCLC, colorectal cancer, ovarian cancer, gastric cancer, hepatocellular carcinoma, pancreatic carcinoma, pancreatic cancer, Pancreatic ductal adenocarcinoma, squamous cell carcinoma of the head and neck, cancer of the head or neck, gastrointestinal tract, stomach cancer, HIV, Hepatitis A, Hepatitis B, Hepatitis C, hepatitis D, herpes viruses, papillomaviruses, influenza, bone cancer, skin cancer, rectal cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the urethra, cancer of the penis, cancer of the bladder, cancer of the kidney, cancer of the ureter, carcinoma of the renal pelvis, neoplasm of the central nervous system (CNS), tumor angiogenesis, spinal axis tumor, brain stem glioma, pituitary adenoma, epidermoid cancer, abestosis, carcinoma, adenocarcinoma, papillary carcinoma, cystadenocarcinoma, bronchogenic carcinoma, renal cell carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and fibroma.

In some embodiments, a therapeutically effective amount of one or more additional therapeutic agents is further administered to the subject. In some embodiments, the one or more additional therapeutic agents is selected from the group consisting of an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. In some embodiments, the one or more additional therapeutic agent is an antagonist of a chemokine and/or chemoattractant receptor, which includes but is not limited to, CCR1, CCR2, CCR3, CCR4, CCR5, CCR6, CCR7, CCR8, CCR9, CCR10, CCR11, CCR12, CXCR1, CXCR2, CXCR3, CXCR4, CXCR5, CXCR6, CXCR7, C3aR, and/or C5aR. Chemokine and/or chemoattractant receptor antagonists are known in the art and described in, for example, WO2007/002667, WO2007/002293, WO/2003/105853, WO/2007/022257, WO/2007/059108, WO/2007/044804, WO2007/115232, WO2007/115231, WO2008/147815, WO2010/030815, WO2010/075257, WO2011/163640, WO2010/054006, WO2010/051561, WO2011/035332, WO2013/082490, WO2013/082429, WO2014/085490, WO2014/100735, WO2014/089495, WO2015/084842, WO2016/187393, WO2017/127409, WO 2017/087607, WO2017/087610, WO2017/176620, WO2018/222598, WO2018/222601, WO2013/130811, WO2006/076644, WO2008/008431, WO2009/038847, WO2008/008375, WO2008/008374, WO2008/010934, WO2009/009740, WO2005/112925, WO2005/112916, WO2005/113513, WO2004/085384, WO2004/046092. Chemokine and/or chemoattractant receptor antagonists also include CCX354, CCX9588, CCX140, CCX872, CCX598, CCX6239, CCX9664, CCX2553, CCX3587, CCX3624, CCX 2991, CCX282, CCX025, CCX507, CCX430, CCX765, CCX224, CCX662, CCX650, CCX832, CCX168, CCX168-M1, CCX3022 and/or CCX3384.

In some embodiments, the compounds of the present disclosure may be used to inhibit an infectious disease. The infectious disease includes but is not limited to HIV, Influenza, Herpes, Giardia, Malaria, Leishmania, the pathogenic infection by the virus Hepatitis (A, B, and C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, mycobacteria, staphylococci, streptococci, pneumonococci, meningococci and conococci, *klebsiella, proteus, serratia, pseudomonas, E. coli, legionella*, diphtheria, *salmonella*, bacilli, cholera, tetanus, botulism, anthrax, plague, leptospirosis, and Lyme's disease bacteria, pathogenic infection by the fungi *Candida* (*albicans, krusei, glabrata, tropicalis,* etc.), *Cryptococcus neoformans, Aspergillus* (*fumigatus, niger,* etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis.*

In some embodiments, the compounds of the present disclosure may be used to inhibit HIV infection, delay AIDS progression, deplete HIV viral reservoir or decrease the severity of symptoms or HIV infection and AIDS.

The compounds of the present disclosure may be used for the treatment of cancers and precancerous conditions in a subject.

Treatment methods provided herein include, in general, administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In a preferred embodiment, the compound(s) of the disclosure are preferably administered to a patient (e.g., a human) intravenously, orally or topically. The effective amount may be an amount sufficient to modulate the PD-1/PD-L1 interaction and/or an amount sufficient to reduce or alleviate the symptoms presented by the patient. Preferably, the amount administered is sufficient to yield a plasma concentration of the compound (or its active metabolite, if the compound is a pro-drug) high enough to sufficiently modulate the PD-1/PD-L1 interaction. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Combinations

A concomitant medicine comprising the compounds of the present disclosure and other drug may be administered as a combination preparation in which both components are contained in a single formulation, or administered as separate formulations. The administration by separate formulations includes simultaneous administration and administration with some time intervals. In the case of the administration with some time intervals, the compound of the present disclosure can be administered first, followed by another drug or another drug can be administered first, followed by the compound of the present disclosure. The administration method of the respective drugs may be the same or different.

The dosage of the other drug can be properly selected, based on a dosage that has been clinically used. The compounding ratio of the compound of the present disclosure and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present disclosure. The other drug may be a combination of two or more kind of arbitrary drugs in a proper proportion.

The compounds described herein may be used or combined with one or more therapeutic agent such as an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. These therapeutic agents may be in the forms of compounds, antibodies, polypeptides, or polynucleotides.

The compounds described herein may be used or combined with one or more of a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a virus, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, or any combination thereof.

Examples of chemotherapeutics include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs.

The compounds described herein may be used or combined with a cancer treatment adjunct, such as a leucopenia (neutropenia) treatment drug, thrombocytopenia treatment drug, antiemetic and cancer pain intervention drug, concomitantly or in a mixture form.

The compounds described herein may be used or combined with a kinase inhibitor.

In one embodiment, the compounds of the present disclosure can be used with other immunomodulators and/or a potentiating agent concomitantly or in a mixture form. Examples of the immunomodulator include various cytokines, vaccines and adjuvants. Examples of these cytokines, vaccines and adjuvants that stimulates immune responses include but not limited to GM-CSF, M-CSF, G-CSF, interferon-a, beta, or gamma, IL-1, IL-2, IL-3, IL-12, Poly (I:C) and CPG. The potentiating agents include cyclophosphamide and analogs of cyclophosphamide, anti-TGF and imatinib (Gleevac), a mitosis inhibitor, such as paclitaxel, Sunitinib (Sutent) or other antiangiogenic agents, an aromatase inhibitor, such as letrozole, an A2a adenosine receptor (A2AR) antagonist, an angiogenesis inhibitor, anthracyclines, oxaliplatin, doxorubicin, TLR4 antagonists, and IL-18 antagonists.

In some embodiments, the compounds described herein may be used or combined with one or more modulator of CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, ChemR23, C5aR, C5a, and C5. In some embodiments, the modulator is an antagonist.

In some embodiments, the compounds described herein may be used or combined with one or more chemokine and/or chemoattractant receptor antagonists described in, for example, WO2007/002667, WO2007/002293, WO/2003/105853, WO/2007/022257, WO/2007/059108, WO/2007/044804, WO2007/115232, WO2007/115231, WO2008/147815, WO2010/030815, WO2010/075257, WO2011/163640, WO2010/054006, WO2010/051561, WO2011/035332, WO2013/082490, WO2013/082429, WO2014/085490, WO2014/100735, WO2014/089495, WO2015/084842, WO2016/187393, WO2017/127409, WO 2017/087607, WO2017/087610, WO2017/176620, WO2018/222598, WO2018/222601, WO2013/130811, WO2006/076644, WO2008/008431, WO2009/038847, WO2008/008375, WO2008/008374, WO2008/010934, WO2009/009740, WO2005/112925, WO2005/112916, WO2005/113513, WO2004/085384, WO2004/046092. Chemokine and/or chemoattractant receptor antagonists useful in the present disclosure also include CCX354, CCX9588, CCX140, CCX872, CCX598, CCX6239, CCX9664, CCX2553, CCX3587, CCX3624, CCX 2991, CCX282, CCX025, CCX507, CCX430, CCX765, CCX224, CCX662, CCX650, CCX832, CCX168, CCX168-M1, CCX3022 and/or CCX3384.

Dosage

Dosage levels of the order of from about 0.1 mg to about 140 mg per kilogram of body weight per day are useful in the treatment or preventions of conditions involving the PD-1/PD-L1 interaction. The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 μg (micrograms)/mL serum, more preferably sufficient compound to achieve a serum concentration of 20 ng-1 μg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

In another aspect of the disclosure, the compounds of the disclosure can be used in a variety of non-pharmaceutical in vitro and in vivo application. The compounds of the disclosure may also be used as positive controls in assays for PD-1/PD-L1 interaction activity, i.e., as standards for determining the ability of a candidate agent to bind to PD-1 and/or PD-L1, or as radiotracers for positron emission tomography (PET) imaging or for single photon emission computerized tomography (SPECT).

Also within the scope of the present disclosure are kits comprising a compound of the present disclosure or pharmaceutically acceptable salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

EXAMPLES

The following Examples illustrate various methods of making compounds of this disclosure including compounds of Formulae (I), (Ia), (Ib), (Ic) or (Id). The following examples are offered to illustrate, but not to limit the claimed disclosure.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge. In the examples, a single m/z value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol or CH$_3$CN at 0.1 mg/mL and 1 microliter was infused with the delivery solvent into the mass spectrometer, which scanned from 100 to 1000 Daltons. All compounds could be analyzed in the positive or negative ESI mode, using acetonitrile/water with 1% formic acid as the delivery solvent.

The following abbreviations are used in the Examples and throughout the description of the disclosure: TLC means Thin layer chromatography; THF means tetrahydrofuran; DCE means 1,2-dichloroethane; DMF means N,N-dimethylformamide; TFA means trifluoroacetic acid; Bpin and pinB both mean 4,4,5,5-tetramethyl-1,3,2-dioxaborolan-2-yl.

Compounds within the scope of this disclosure can be synthesized as described below, using a variety of reactions known to the skilled artisan. One skilled in the art will also recognize that alternative methods may be employed to synthesize the target compounds of this disclosure, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed unless a specific enantiomer is specified.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: 6-(2,2'-dimethyl-[1,1'-biphenyl]-3-yl)-1,2,3,4-tetrahydroisoquinoline

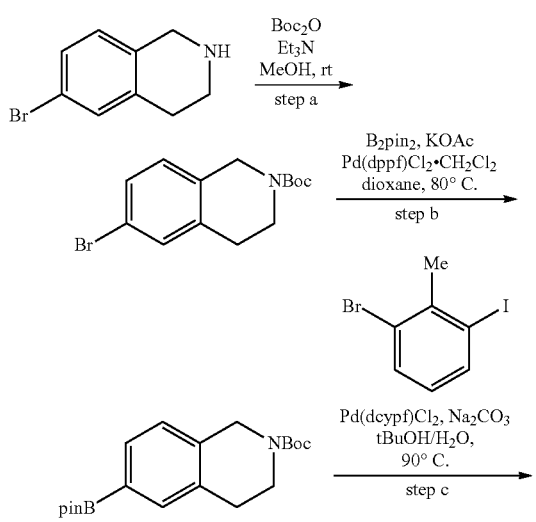

-continued

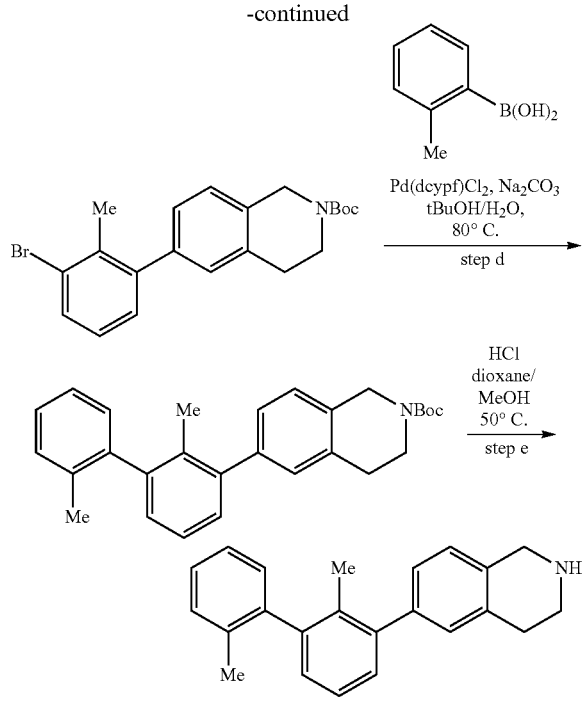

Step a: A solution of 6-bromo-1,2,3,4-tetrahydroisoquinoline (3.18 g, 15.0 mmol), di-tert-butyl dicarbonate (6.55 g, 30.0 mmol), and Et₃N (8.4 mL, 60.0 mmol) in MeOH (40 mL) was stirred at room temperature overnight. The reaction mixture was concentrated and purified by silica gel flash chromatography (0-40% EtOAc/hexanes) to yield tert-butyl 6-bromo-3,4-dihydroisoquinoline-2(1H)-carboxylate.

Step b: A mixture of tert-butyl 6-bromo-3,4-dihydroisoquinoline-2(1H)-carboxylate (3.12 g, 10.0 mmol), bis(pinacolato)diboron (3.05 g, 12.0 mmol), and KOAc (2.94 g, 30.0 mmol) in dioxane (50 mL) was degassed (N₂) for 20 minutes. [1,1'-bis(diphenylphosphino)ferrocene]-dichloropalladium(II) complex with dichloromethane (817 mg, 1.0 mmol) was added, and the reaction mixture was degassed (N₂) for an additional 5 minutes and stirred at 80° C. overnight under N₂. The reaction mixture was cooled to room temperature, diluted with sat. NaHCO₃ (100 mL), and extracted with EtOAc (3×100 mL). The combined organic layers were washed with brine (100 mL), dried over MgSO₄, filtered, and concentrated. Purification by silica gel flash chromatography (0-30% EtOAc/hexanes) gave tert-butyl 6-(4,4,5,5-tetramethyl-1,3,2-dioxaborolan-2-yl)-3,4-dihydroisoquinoline-2(1H)-carboxylate.

Step c: A mixture of tert-butyl 6-(4,4,5,5-tetramethyl-1,3,2-dioxaborolan-2-yl)-3,4-dihydroisoquinoline-2(1H)-carboxylate (750 mg, 2.1 mmol), 1-bromo-3-iodo-2-methylbenzene (802 mg, 2.7 mmol), dichloro[1,1'-bis(dicyclohexylphosphino)ferrocene]palladium(II) (159 mg, 0.21 mmol), and Na₂CO₃ (562 mg, 5.3 mmol) in 3:1 t-BuOH:H₂O (12 mL) was degassed (N₂) for 10 minutes and stirred at 90° C. overnight. The reaction mixture was cooled to room temperature, diluted with H₂O (20 mL), and extracted with CH₂Cl₂ (3×10 mL). The combined organic layers were washed with brine (20 mL), dried over MgSO₄, filtered, and concentrated. Purification by silica gel flash chromatography (0-30% EtOAc/hexanes) gave tert-butyl 6-(3-bromo-2-methylphenyl)-3,4-dihydroisoquinoline-2(1H)-carboxylate.

Step d: A mixture of tert-butyl 6-(3-bromo-2-methylphenyl)-3,4-dihydroisoquinoline-2(1H)-carboxylate (100 mg, 0.25 mmol), o-tolylboronic acid (52 mg, 0.38 mmol), dichloro[1,1'-bis(dicyclohexylphosphino)ferrocene]palladium(II) (19 mg, 0.025 mmol), and Na₂CO₃ (67 mg, 0.63 mmol) in 3:1 t-BuOH:H₂O (2 mL) was degassed (N₂) for 5 minutes and stirred at 80° C. overnight. The reaction mixture was cooled to room temperature, diluted with H₂O (10 mL), and extracted with CH₂Cl₂ (3×10 mL). The combined organic layers were washed with brine (10 mL), dried over MgSO₄, filtered, and concentrated. Purification by silica gel flash chromatography (0-100% CH₂Cl₂/hexanes) gave tert-butyl 6-(2,2'-dimethyl-[1,1'-biphenyl]-3-yl)-3,4-dihydroisoquinoline-2(1H)-carboxylate.

Step e: tert-butyl 6-(2,2'-dimethyl-[1,1'-biphenyl]-3-yl)-3,4-dihydroisoquinoline-2(1H)-carboxylate (65 mg, 0.16 mmol) was dissolved in MeOH (0.5 mL), 4M HCl/dioxane (0.5 mL) was added, and the reaction mixture was stirred at 50° C. for 1 hour. Purification by reverse phase preparative HPLC (H₂O/MeCN with 0.1% TFA) gave 6-(2,2'-dimethyl-[1,1'-biphenyl]-3-yl)-1,2,3,4-tetrahydroisoquinoline as a TFA salt. ¹H-NMR (400 MHz, (CD₃)₂SO) δ 9.09 (br s, 2H), 7.34-7.22 (m, 7H), 7.18 (dd, J=1.4, 7.7 Hz, 1H), 7.10 (td, J=1.6, 7.4 Hz, 2H), 4.33 (t, J=4.2 Hz, 2H), 3.42 (dd, J=5.1, 7.8 Hz, 2H), 3.06 (t, J=6.4 Hz, 2H), 2.05 (s, 3H), 1.85 (s, 3H). MS: (ES) m/z calculated for C₂₃H₂₄N [M+H]⁺ 314.2, found 314.1.

Example 2: 6-(3'-methoxy-2-methyl-[1,1'-biphenyl]-3-yl)-1,2,3,4-tetrahydroisoquinoline

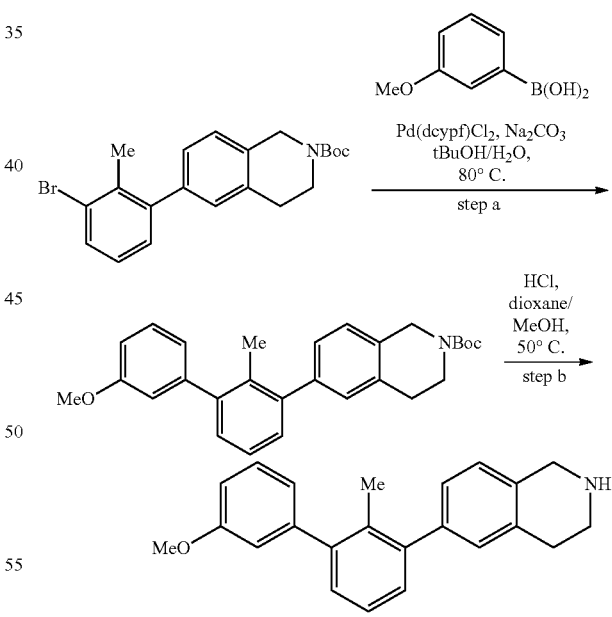

Step a: A mixture of tert-butyl 6-(3-bromo-2-methylphenyl)-3,4-dihydroisoquinoline-2(1H)-carboxylate (100 mg, 0.25 mmol), 3-methoxyphenylboronic acid (58 mg, 0.38 mmol), dichloro[1,1'-bis(dicyclohexylphosphino)ferrocene]palladium(II) (19 mg, 0.025 mmol), and Na₂CO₃ (67 mg, 0.63 mmol) in 3:1 t-BuOH:H₂O (2 mL) was degassed (N₂) for 5 minutes and stirred at 80° C. overnight. The reaction mixture was cooled to room temperature, diluted with H₂O (10 mL), and extracted with CH₂Cl₂ (3×10 mL). The combined organic layers were washed with brine (10 mL), dried over MgSO$_4$, filtered, and concentrated. Purification by silica gel flash chromatography (0-30% EtOAc/hexanes) gave tert-butyl 6-(3'-methoxy-2-methyl-[1,1'-biphenyl]-3-yl)-3,4-dihydroisoquinoline-2(1H)-carboxylate.

Step b: tert-butyl 6-(3'-methoxy-2-methyl-[1,1'-biphenyl]-3-yl)-3,4-dihydroisoquinoline-2(1H)-carboxylate (75 mg, 0.17 mmol) was dissolved in MeOH (0.5 mL), 4M HCl/dioxane (0.5 mL) was added, and the reaction mixture was stirred at 50° C. for 1 hour. Purification by reverse phase preparative HPLC (H$_2$O/MeCN with 0.1% TFA) gave 6-(3'-methoxy-2-methyl-[1,1'-biphenyl]-3-yl)-1,2,3,4-tetrahydroisoquinoline as a TFA salt. $^1$H-NMR (400 MHz, (CD$_3$)$_2$SO) δ 9.06 (br s, 2H), 7.39-7.16 (m, 7H), 6.95-6.89 (m, 3H), 4.36-4.30 (m, 2H), 3.79 (s, 3H), 3.47-3.40 (m, 2H), 3.05 (t, J=6.3 Hz, 2H), 2.06 (s, 3H). MS: (ES) m/z calculated for C$_{23}$H$_{24}$NO [M+H]$^+$ 330.2, found 330.1.

Example 3: 6-(3'-methoxy-2,2'-dimethyl-[1,1'-biphenyl]-3-yl)-1,2,3,4-tetrahydroisoquinoline

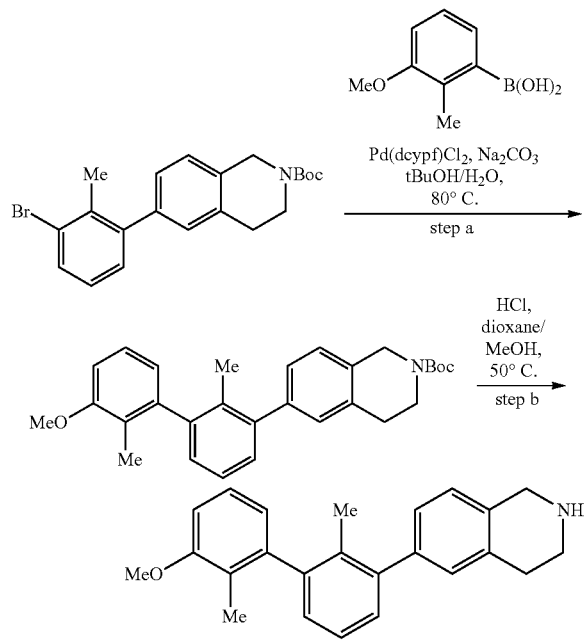

Step a: A mixture of tert-butyl 6-(3-bromo-2-methylphenyl)-3,4-dihydroisoquinoline-2(1H)-carboxylate (100 mg, 0.25 mmol), 3-methoxy-2-methylphenylboronic acid (63 mg, 0.38 mmol), dichloro[1,1'-bis(dicyclohexylphosphino)ferrocene]palladium(II) (19 mg, 0.025 mmol), and Na$_2$CO$_3$ (67 mg, 0.63 mmol) in 3:1 t-BuOH:H$_2$O (2 mL) was degassed (N$_2$) for 5 minutes and stirred at 80° C. overnight. The reaction mixture was cooled to room temperature, diluted with H$_2$O (10 mL), and extracted with CH$_2$Cl$_2$ (3×10 mL). The combined organic layers were washed with brine (10 mL), dried over MgSO$_4$, filtered, and concentrated. Purification by silica gel flash chromatography (0-30% EtOAc/hexanes) gave tert-butyl 6-(3'-methoxy-2,2'-dimethyl-[1,1'-biphenyl]-3-yl)-3,4-dihydroisoquinoline-2(1H)-carboxylate.

Step b: tert-butyl 6-(3'-methoxy-2,2'-dimethyl-[1,1'-biphenyl]-3-yl)-3,4-dihydroisoquinoline-2(1H)-carboxylate (70 mg, 0.16 mmol) was dissolved in MeOH (0.5 mL), 4M HCl/dioxane (0.5 mL) was added, and the reaction mixture was stirred at 50° C. for 1 hour. Purification by reverse phase preparative HPLC (H$_2$O/MeCN with 0.1% TFA) gave 6-(3'-methoxy-2,2'-dimethyl-[1,1'-biphenyl]-3-yl)-1,2,3,4-tetrahydroisoquinoline as a TFA salt. $^1$H-NMR (400 MHz, (CD$_3$)$_2$SO) δ 9.05 (br s, 2H), 7.33-7.20 (m, 5H), 7.18 (dd, J=1.4, 7.8 Hz, 1H), 7.07 (dd, J=1.4, 7.6 Hz, 1H), 6.97 (dd, J=1.1, 8.4 Hz, 1H), 6.72 (dd, J=1.1, 7.5 Hz, 1H), 4.35-4.30 (m, 2H), 3.83 (s, 3H), 3.47-3.39 (m, 2H), 3.05 (t, J=6.3 Hz, 2H), 1.88 (s, 3H), 1.85 (s, 3H). MS: (ES) m/z calculated for C$_{24}$H$_{26}$NO [M+H]$^+$ 344.2, found 344.2.

Example 4: 6-(3'-(3-(2,2-dimethylazetidin-1-yl)propoxy)-2,2'-dimethyl-[1,1'-biphenyl]-3-yl)-1,2,3,4-tetrahydroisoquinoline

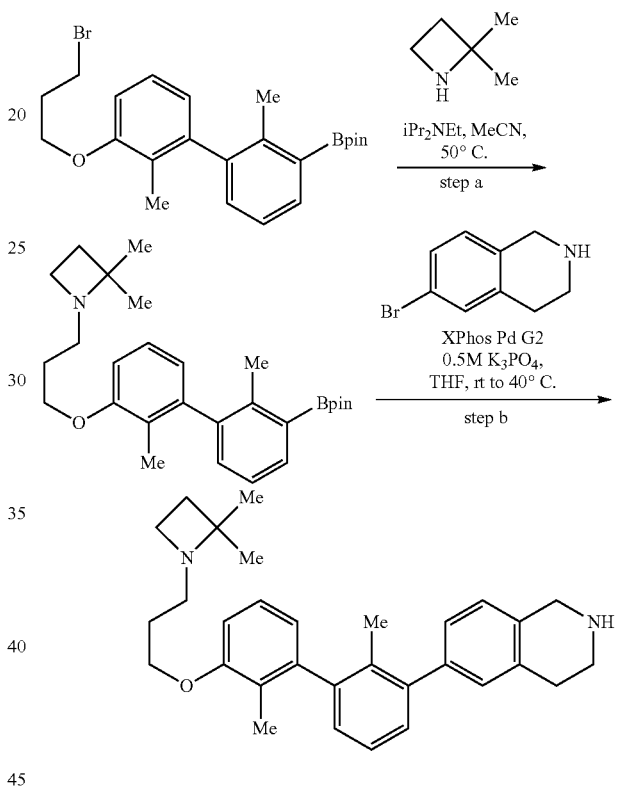

Step a: To a solution of 2-(3'-(3-bromopropoxy)-2,2'-dimethyl-[1,1'-biphenyl]-3-yl)-4,4,5,5-tetramethyl-1,3,2-dioxaborolane (130 mg, 0.29 mmol) and 2,2-dimethylazetidine (33 mg, 0.38 mmol) in MeCN (2 mL) was slowly added iPr$_2$NEt (0.15 mL, 0.87 mmol). The mixture was heated to 50° C. and stirred for 3 h. The reaction mixture was concentrated, and the crude material was purified by silica gel flash chromatography (0-15% MeOH/CH$_2$Cl$_2$) to obtain 1-(3-((2,2'-dimethyl-3'-(4,4,5,5-tetramethyl-1,3,2-dioxaborolan-2-yl)-[1,1'-biphenyl]-3-yl)oxy)propyl)-2,2-dimethylazetidine.

Step b: To a biphasic mixture of 1-(3-((2,2'-dimethyl-3'-(4,4,5,5-tetramethyl-1,3,2-dioxaborolan-2-yl)-[1,1'-biphenyl]-3-yl)oxy)propyl)-2,2-dimethylazetidine (45 mg, 0.10 mmol), 6-bromo-1,2,3,4-tetrahydroisoquinoline (42 mg, 0.20 mmol) in 0.5 M K$_3$PO$_4$ (0.60 mL 0.30 mmol) and THF (1.5 mL) was added XPhos Pd G2 (16 mg, 0.020 mmol). The reaction mixture was stirred at room temperature for 1 h and then heated to 40° C. for 12 h. The reaction mixture was allowed to cool to room temperature, and the organic layer was separated, filtered, and purified by reverse phase preparative HPLC (H$_2$O/MeCN with 0.1% TFA) to obtain 6-(3'-(3-(2,2-dimethylazetidin-1-yl)propoxy)-2,2'- dimethyl-[1,1'-biphenyl]-3-yl)-1,2,3,4-tetrahydroisoquinoline. MS: (ES) m/z calculated for $C_{31}H_{39}N_2O$ [M+H]$^+$ 445.3, found 455.3. $^1$H-NMR (400 MHz, CDC$_3$) δ 7.29-7.26 (m, 1H), 7.25-7.22 (m, 1H), 7.22-7.18 (m, 1H), 7.18-7.16 (m, 2H), 7.15 (d, J=8.0 Hz, 1H), 7.10 (dt, J=7.5, 1.6 Hz, 11H), 6.82 (d, J=1.8 Hz, 11H), 6.80 (d, J=2.5 Hz, 1H), 4.43-4.34 (m, 3H), 4.12-4.02 (m, 2H), 3.62-3.47 (m, 3H), 3.36-3.25 (m, 1H), 3.21-3.08 (m, 3H), 2.67 (q, J=9.9 Hz, 1H), 2.23-2.14 (m, 2H), 2.14-2.06 (m, 1H), 1.95 (s, 3H), 1.89 (s, 3H), 1.69 (s, 3H), 1.61 (s, 3H).

Example 5: 6-(3'-(3-(2,2-dimethylazetidin-1-yl)propoxy)-2'-methyl-[1,1'-biphenyl]-3-yl)-1,2,3,4-tetrahydroisoquinoline

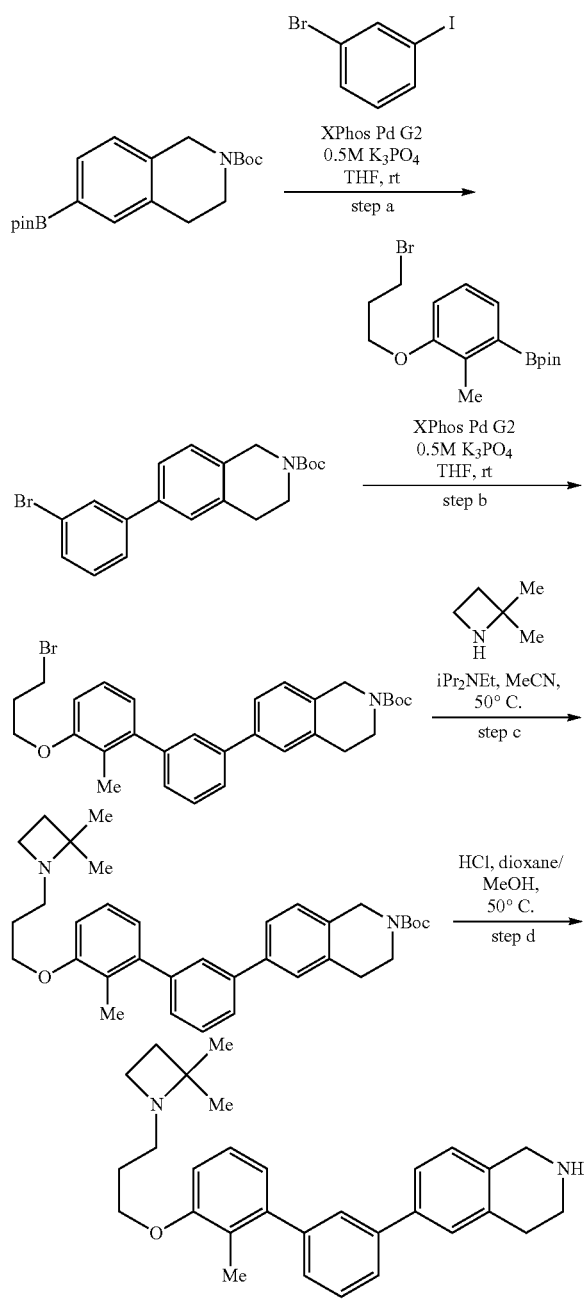

Step a. A mixture of 1-bromo-3-iodobenzene (283 mg, 1.0 mmol), tert-butyl 6-(4,4,5,5-tetramethyl-1,3,2-dioxaborolan-2-yl)-3,4-dihydroisoquinoline-2(1H)-carboxylate (359 mg, 1.0 mmol), THF (10 mL), and 0.5 M K$_3$PO$_4$ (10 mL) was degassed (N$_2$) for 5 minutes. XPhos Pd G2 (79 mg, 0.10 mmol) was added, and the reaction mixture was degassed (N$_2$) for an additional 5 minutes and stirred at room temperature overnight. The reaction mixture was diluted with H$_2$O (10 mL) and extracted with EtOAc (3×10 mL). The combined organic layers were washed with brine (10 mL), dried over MgSO$_4$, filtered, and concentrated. Purification by silica gel flash chromatography (0-30% EtOAc/hexanes) gave tert-butyl 6-(3-bromophenyl)-3,4-dihydroisoquinoline-2(1H)-carboxylate.

Step b: A mixture of tert-butyl 6-(3-bromophenyl)-3,4-dihydroisoquinoline-2(1H)-carboxylate (100 mg, 0.26 mmol), 2-(3-(3-bromopropoxy)-2-methylphenyl)-4,4,5,5-tetramethyl-1,3,2-dioxaborolane (173 mg, 0.39 mmol), THF (3 mL), and 0.5 M K$_3$PO$_4$ (3 mL) was degassed (N$_2$) for 5 minutes. XPhos Pd G2 (20 mg, 0.026 mmol) was added, and the reaction mixture was degassed (N$_2$) for an additional 5 minutes and stirred at room temperature overnight. The reaction mixture was diluted with H$_2$O (10 mL) and extracted with EtOAc (3×10 mL). The combined organic layers were washed with brine (10 mL), dried over MgSO$_4$, filtered, and concentrated. Purification by silica gel flash chromatography (0-30% EtOAc/hexanes) gave tert-butyl 6-(3'-(3-bromopropoxy)-2'-methyl-[1,1'-biphenyl]-3-yl)-3,4-dihydroisoquinoline-2(1H)-carboxylate.

Step c: A solution of tert-butyl 6-(3'-(3-bromopropoxy)-2'-methyl-[1,1'-biphenyl]-3-yl)-3,4-dihydroisoquinoline-2(1H)-carboxylate (80 mg, 0.15 mmol), 2,2-dimethylazetidine (26 mg, 0.30 mmol), and iPr$_2$NEt (79 μL, 0.45 mmol) in MeCN (2 mL) was stirred at 50° C. for 5 hours. The reaction mixture was cooled to room temperature and concentrated. Purification by silica gel flash chromatography (0-10% MeOH/CH$_2$Cl$_2$) gave tert-butyl 6-(3'-(3-(2,2-dimethylazetidin-1-yl)propoxy)-2'-methyl-[1,1'-biphenyl]-3-yl)-3,4-dihydroisoquinoline-2(1H)-carboxylate.

Step d: tert-butyl 6-(3'-(3-(2,2-dimethylazetidin-1-yl)propoxy)-2'-methyl-[1,1'-biphenyl]-3-yl)-3,4-dihydroisoquinoline-2(1H)-carboxylate (55 mg, 0.10 mmol) was dissolved in MeOH (0.5 mL), 4M HCl/dioxane (0.5 mL) was added, and the reaction mixture was stirred at 50° C. for 1 hour. Purification by reverse phase preparative HPLC (H$_2$O/MeCN with 0.1% TFA) gave 6-(3'-(3-(2,2-dimethylazetidin-1-yl)propoxy)-2'-methyl-[1,1'-biphenyl]-3-yl)-1,2,3,4-tetrahydroisoquinoline as a bis-TFA salt. $^1$H-NMR (400 MHz, (CD$_3$)$_2$SO) δ 9.64 (br s, 1H) 9.09 (br s, 2H), 7.67 (d, J=8.0 Hz, 1H), 7.62-7.58 (m, 2H), 7.56-7.51 (m, 2H), 7.33-7.28 (m, 2H), 7.25 (t, J=7.9 Hz, 1H), 6.99 (d, J=8.4 Hz, 1H), 6.91 (d, J=7.6 Hz, 1H), 4.35-4.29 (m, 2H), 4.13-4.01 (m, 2H), 3.99-3.87 (m, 2H), 3.46-3.38 (m, 2H), 3.33-3.20 (m, 1H), 3.19-3.10 (m, 1H), 3.06 (t, J=6.3 Hz, 2H), 2.39-2.29 (m, 1H), 2.15-2.06 (m, 4H), 2.03-1.94 (m, 2H), 1.57 (s, 3H), 1.55 (s, 3H). MS: (ES) m/z calculated for $C_{30}H_{37}N_2O$ [M+H]$^+$ 441.3, found 441.3.

Example 6: 3'-(3-(2,2-dimethylazetidin-1-yl)propoxy)-2'-methyl-3-(1,2,3,4-tetrahydroisoquinolin-6-yl)-[1,1'-biphenyl]-2-carbonitrile

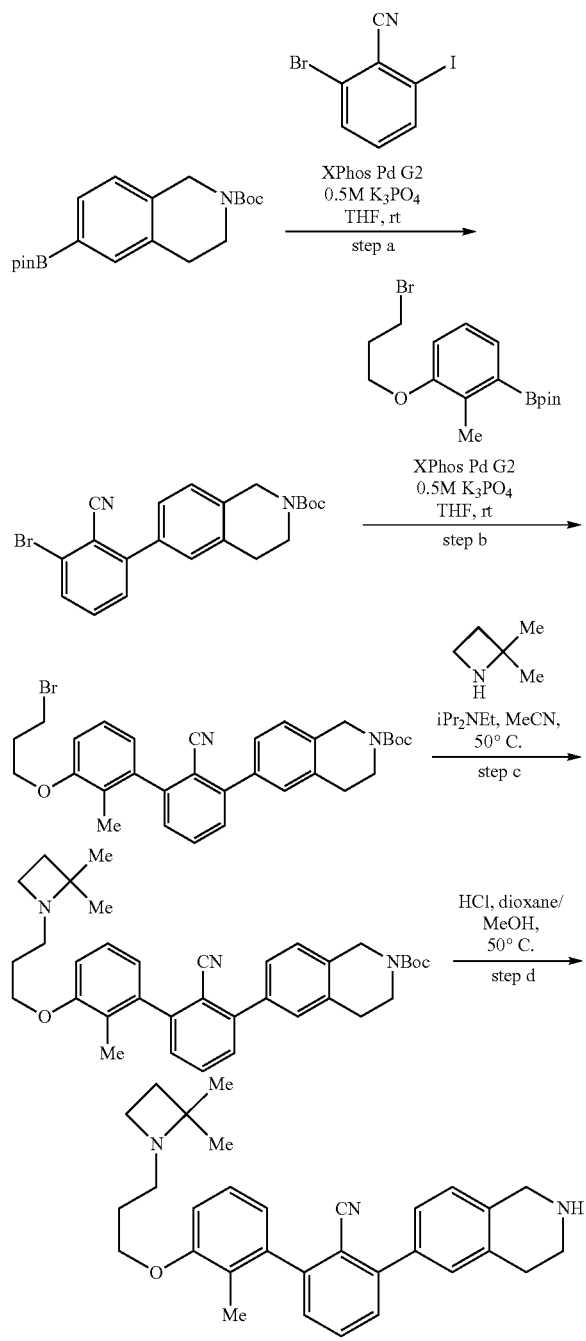

Step a: A mixture of 2-bromo-6-iodobenzonitrile (308 mg, 1.0 mmol), tert-butyl 6-(4,4,5,5-tetramethyl-1,3,2-dioxaborolan-2-yl)-3,4-dihydroisoquinoline-2(1H)-carboxylate (359 mg, 1.0 mmol), THF (10 mL), and 0.5 M K$_3$PO$_4$ (10 mL) was degassed (N$_2$) for 5 minutes. XPhos Pd G2 (79 mg, 0.10 mmol) was added, and the reaction mixture was degassed (N$_2$) for an additional 5 minutes and stirred at room temperature overnight. The reaction mixture was diluted with H$_2$O (10 mL) and extracted with EtOAc (3×10 mL). The combined organic layers were washed with brine (10 mL), dried over MgSO$_4$, filtered, and concentrated. Purification by silica gel flash chromatography (0-50% EtOAc/hexanes) gave tert-butyl 6-(3-bromo-2-cyanophenyl)-3,4-dihydroisoquinoline-2(1H)-carboxylate.

Step b: A mixture of tert-butyl 6-(3-bromo-2-cyanophenyl)-3,4-dihydroisoquinoline-2(1H)-carboxylate (170 mg, 0.41 mmol), 2-(3-(3-bromopropoxy)-2-methylphenyl)-4,4,5,5-tetramethyl-1,3,2-dioxaborolane (275 mg, 0.62 mmol), THF (4 mL), and 0.5 M K$_3$PO$_4$ (4 mL) was degassed (N$_2$) for 5 minutes. XPhos Pd G2 (32 mg, 0.041 mmol) was added, and the reaction mixture was degassed (N$_2$) for an additional 5 minutes and stirred at room temperature overnight. The reaction mixture was diluted with H$_2$O (10 mL) and extracted with EtOAc (3×10 mL). The combined organic layers were washed with brine (10 mL), dried over MgSO$_4$, filtered, and concentrated. Purification by silica gel flash chromatography (0-30% EtOAc/hexanes) gave tert-butyl 6-(3'-(3-bromopropoxy)-2-cyano-2'-methyl-[1,1'-biphenyl]-3-yl)-3,4-dihydroisoquinoline-2(1H)-carboxylate.

Step c: A solution of tert-butyl 6-(3'-(3-bromopropoxy)-2-cyano-2'-methyl-[1,1'-biphenyl]-3-yl)-3,4-dihydroisoquinoline-2(1H)-carboxylate (140 mg, 0.25 mmol), 2,2-dimethylazetidine (43 mg, 0.50 mmol), and iPr$_2$NEt (0.13 mL, 0.75 mmol) in MeCN (3 mL) was stirred at 50° C. for 5 hours. The reaction mixture was cooled to room temperature and concentrated. Purification by silica gel flash chromatography (0-10% MeOH/CH$_2$Cl$_2$) gave tert-butyl 6-(2-cyano-3'-(3-(2,2-dimethylazetidin-1-yl)propoxy)-2'-methyl-[1,1'-biphenyl]-3-yl)-3,4-dihydroisoquinoline-2(1H)-carboxylate.

Step d: tert-butyl 6-(2-cyano-3'-(3-(2,2-dimethylazetidin-1-yl)propoxy)-2'-methyl-[1,1'-biphenyl]-3-yl)-3,4-dihydroisoquinoline-2(1H)-carboxylate (120 mg, 0.21 mmol) was dissolved in MeOH (0.5 mL), 4M HCl/dioxane (0.5 mL) was added, and the reaction mixture was stirred at 50° C. for 1 hour. Purification by reverse phase preparative HPLC (H$_2$O/MeCN with 0.1% TFA) gave 3'-(3-(2,2-dimethylazetidin-1-yl)propoxy)-2'-methyl-3-(1,2,3,4-tetrahydroisoquinolin-6-yl)-[1,1'-biphenyl]-2-carbonitrile as a bis-TFA salt. $^1$H-NMR (400 MHz, (CD$_3$)$_2$SO) δ 9.28 (br s, 1H) 9.16 (br s, 2H), 7.84 (d, J=7.8 Hz, 1H), 7.61 (dd, J=1.1, 7.9 Hz, 1H), 7.53-7.47 (m, 2H), 7.45 (dd, J=1.1, 7.8 Hz, 1H), 7.39 (d, J=8.0 Hz, 1H), 7.29 (t, J=7.9 Hz, 1H), 7.07 (d, J=8.3 Hz, 1H), 6.90 (d, J=7.6 Hz, 1H), 4.37 (t, J=4.2 Hz, 2H), 4.17-4.02 (m, 2H), 4.00-3.87 (m, 2H), 3.49-3.41 (m, 2H), 3.34-3.22 (m, 1H), 3.19-3.11 (m, 1H), 3.08 (t, J=6.2 Hz, 2H), 2.39-2.29 (m, 1H), 2.14-2.05 (m, 1H), 2.05-1.95 (m, 5H), 1.57 (s, 3H), 1.55 (s, 3H). MS: (ES) m/z calculated for C$_{31}$H$_{36}$N$_3$O [M+H]$^+$ 466.3, found 466.4.

Example 7: 6-(3'-(3-(2,2-dimethylazetidin-1-yl)propoxy)-2-fluoro-2'-methyl-[1,1'-biphenyl]-3-yl)-1,2,3,4-tetrahydroisoquinoline

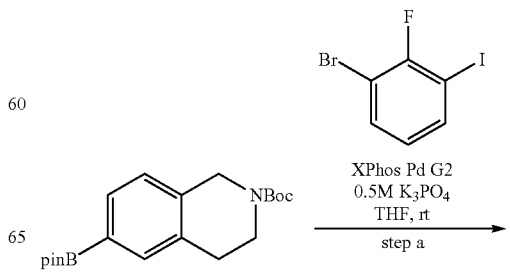

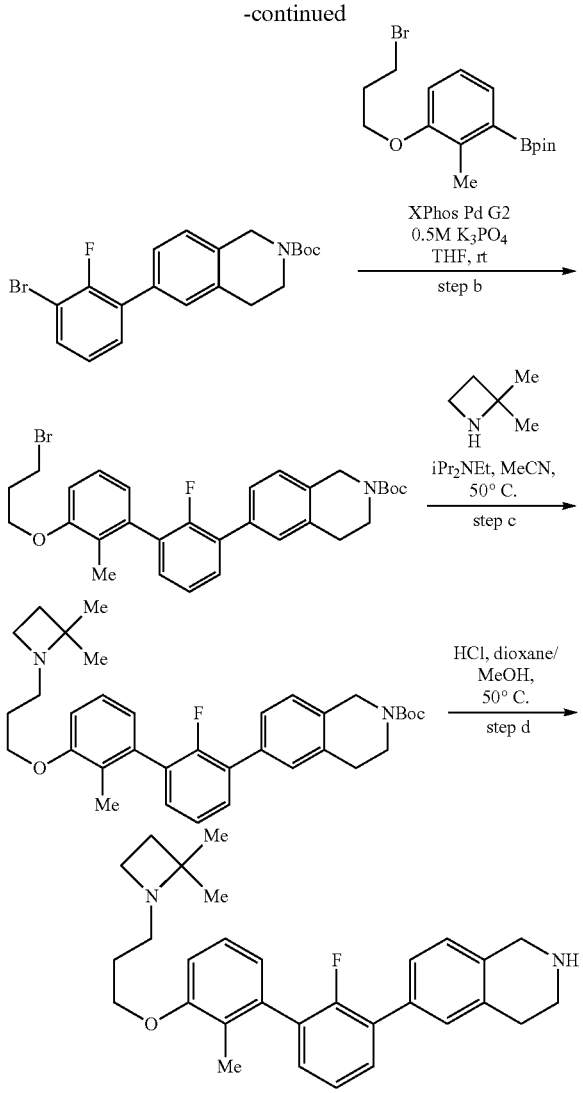

and extracted with EtOAc (3×10 mL). The combined organic layers were washed with brine (10 mL), dried over MgSO4, filtered, and concentrated. Purification by silica gel flash chromatography (0-30% EtOAc/hexanes) gave tert-butyl 6-(3'-(3-bromopropoxy)-2-fluoro-2'-methyl-[1,1'-biphenyl]-3-yl)-3,4-dihydroisoquinoline-2(1H)-carboxylate.

Step c: A solution of tert-butyl 6-(3'-(3-bromopropoxy)-2-fluoro-2'-methyl-[1,1'-biphenyl]-3-yl)-3,4-dihydroisoquinoline-2(1H)-carboxylate (60 mg, 0.11 mmol), 2,2-dimethylazetidine (19 mg, 0.22 mmol), and iPr2NEt (58 µL, 0.33 mmol) in MeCN (1 mL) was stirred at 50° C. for 3 hours. The reaction mixture was cooled to room temperature and concentrated. Purification by silica gel flash chromatography (0-10% MeOH/CH2Cl2) gave tert-butyl 6-(2-fluoro-3'-(3-(2,2-dimethylazetidin-1-yl)propoxy)-2'-methyl-[1,1'-biphenyl]-3-yl)-3,4-dihydroisoquinoline-2(1H)-carboxylate.

Step d: tert-butyl 6-(2-fluoro-3'-(3-(2,2-dimethylazetidin-1-yl)propoxy)-2'-methyl-[1,1'-biphenyl]-3-yl)-3,4-dihydroisoquinoline-2(1H)-carboxylate (35 mg, 0.063 mmol) was dissolved in MeOH (0.5 mL), 4M HCl/dioxane (0.5 mL) was added, and the reaction mixture was stirred at 50° C. for 1 hour. Purification by reverse phase preparative HPLC (H2O/MeCN with 0.1% TFA) gave 6-(3'-(3-(2,2-dimethylazetidin-1-yl)propoxy)-2-fluoro-2'-methyl-[1,1'-biphenyl]-3-yl)-1,2,3,4-tetrahydroisoquinoline as a bis-TFA salt. $^1$H-NMR (400 MHz, (CD3)2SO) δ 9.64 (br s, 1H) 9.10 (br s, 2H), 7.53 (td, J=1.8, 7.6 Hz, 1H), 7.47-7.42 (m, 2H), 7.38 (t, J=7.6 Hz, 1H), 7.35-7.23 (m, 3H), 7.02 (d, J=8.0 Hz, 1H), 6.88 (d, J=7.6 Hz, 1H), 4.36-4.30 (m, 2H), 4.14-4.02 (m, 2H), 3.98-3.86 (m, 2H), 3.47-3.38 (m, 2H), 3.32-3.21 (m, 1H), 3.18-3.09 (m, 1H), 3.05 (t, J=6.3 Hz, 2H), 2.39-2.29 (m, 1H), 2.14-2.06 (m, 1H), 2.04-1.94 (m, 5H), 1.57 (s, 3H), 1.54 (s, 3H). MS: (ES) m/z calculated for $C_{30}H_{36}FN_2O$ [M+H]$^+$ 459.3, found 459.4.

Example 8: 6-(3'-(3-(2,2-dimethylazetidin-1-yl)propoxy)-2-chloro-2'-methyl-[1,1'-biphenyl]-3-yl)-1,2,3,4-tetrahydroisoquinoline

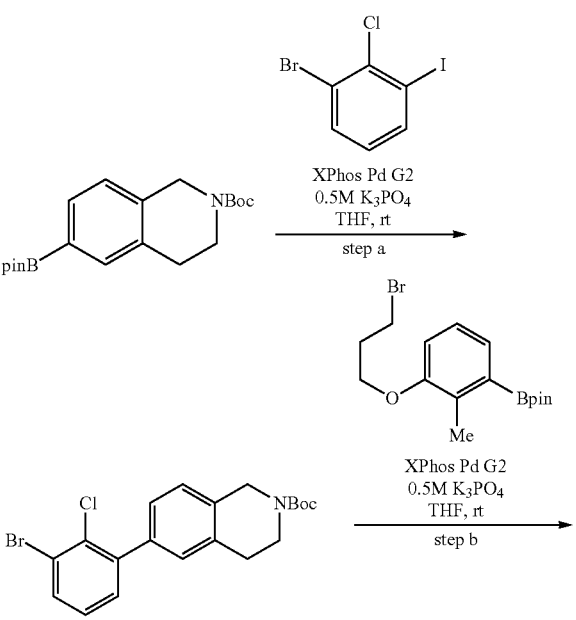

Step a: A mixture of 1-bromo-2-fluoro-3-iodobenzene (250 mg, 0.83 mmol), tert-butyl 6-(4,4,5,5-tetramethyl-1,3,2-dioxaborolan-2-yl)-3,4-dihydroisoquinoline-2(1H)-carboxylate (298 mg, 0.83 mmol), Na2CO3 (180 mg, 1.7 mmol), DME (8 mL), and H2O (2 mL) was degassed (N2) for 5 minutes. Pd(PPh3)4 (197 mg, 0.17 mmol) was added, and the reaction mixture was degassed (N2) for an additional 5 minutes and stirred at 80° C. overnight. The reaction mixture was cooled to room temperature, diluted with H2O (10 mL), and extracted with EtOAc (3×10 mL). The combined organic layers were washed with brine (10 mL), dried over MgSO4, filtered, and concentrated. Purification by silica gel flash chromatography (0-100% CH2Cl2/hexanes) gave tert-butyl 6-(3-bromo-2-fluorophenyl)-3,4-dihydroisoquinoline-2(1H)-carboxylate.

Step b: A mixture of tert-butyl 6-(3-bromo-2-fluorophenyl)-3,4-dihydroisoquinoline-2(1H)-carboxylate (90 mg, 0.22 mmol), 2-(3-(3-bromopropoxy)-2-methylphenyl)-4,4,5,5-tetramethyl-1,3,2-dioxaborolane (146 mg, 0.33 mmol), THF (2 mL), and 0.5 M K3PO4 (2 mL) was degassed (N2) for 5 minutes. XPhos Pd G2 (17 mg, 0.022 mmol) was added, and the reaction mixture was degassed (N2) for an additional 5 minutes and stirred at room temperature overnight. The reaction mixture was diluted with H2O (10 mL)

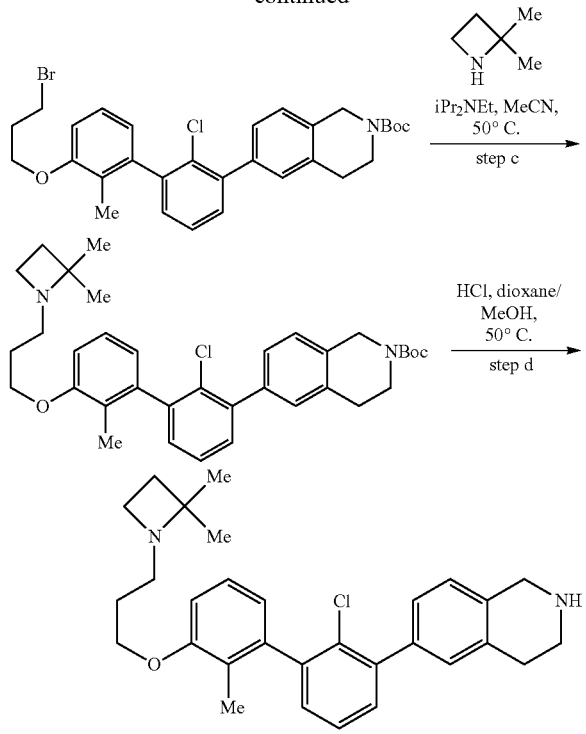

Step a: A mixture of 1-bromo-2-chloro-3-iodobenzene (250 mg, 0.79 mmol), tert-butyl 6-(4,4,5,5-tetramethyl-1,3,2-dioxaborolan-2-yl)-3,4-dihydroisoquinoline-2(1H)-carboxylate (284 mg, 0.79 mmol), THF (8 mL), and 0.5 M $K_3PO_4$ (8 mL) was degassed ($N_2$) for 5 minutes. XPhos Pd G2 (62 mg, 0.079 mmol) was added, and the reaction mixture was degassed ($N_2$) for an additional 5 minutes and stirred at room temperature overnight. The reaction mixture was diluted with $H_2O$ (10 mL) and extracted with EtOAc (3×10 mL). The combined organic layers were washed with brine (10 mL), dried over $MgSO_4$, filtered, and concentrated. Purification by silica gel flash chromatography (0-100% $CH_2Cl_2$/hexanes) gave tert-butyl 6-(3-bromo-2-chlorophenyl)-3,4-dihydroisoquinoline-2(1H)-carboxylate.

Step b: A mixture of tert-butyl 6-(3-bromo-2-chlorophenyl)-3,4-dihydroisoquinoline-2(1H)-carboxylate (100 mg, 0.23 mmol), 2-(3-(3-bromopropoxy)-2-methylphenyl)-4,4,5,5-tetramethyl-1,3,2-dioxaborolane (155 mg, 0.35 mmol), THF (3 mL), and 0.5 M $K_3PO_4$ (3 mL) was degassed ($N_2$) for 5 minutes. XPhos Pd G2 (18 mg, 0.023 mmol) was added, and the reaction mixture was degassed ($N_2$) for an additional 5 minutes and stirred at room temperature overnight. The reaction mixture was diluted with $H_2O$ (10 mL) and extracted with EtOAc (3×10 mL). The combined organic layers were washed with brine (10 mL), dried over $MgSO_4$, filtered, and concentrated. Purification by silica gel flash chromatography (0-100% $CH_2Cl_2$/hexanes) gave tert-butyl 6-(3'-(3-bromopropoxy)-2-chloro-2'-methyl-[1,1'-biphenyl]-3-yl)-3,4-dihydroisoquinoline-2(1H)-carboxylate.

Step c: A solution of tert-butyl 6-(3'-(3-bromopropoxy)-2-chloro-2'-methyl-[1,1'-biphenyl]-3-yl)-3,4-dihydroisoquinoline-2(1H)-carboxylate (100 mg, 0.18 mmol), 2,2-dimethylazetidine (31 mg, 0.36 mmol), and $iPr_2NEt$ (94 μL, 0.54 mmol) in MeCN (2 mL) was stirred at 50° C. for 4 hours. The reaction mixture was cooled to room temperature and concentrated. Purification by silica gel flash chromatography (0-10% MeOH/$CH_2Cl_2$) gave tert-butyl 6-(2-chloro-3'-(3-(2,2-dimethylazetidin-1-yl)propoxy)-2'-methyl-[1,1'-biphenyl]-3-yl)-3,4-dihydroisoquinoline-2(1H)-carboxylate.

Step d: tert-butyl 6-(2-chloro-3'-(3-(2,2-dimethylazetidin-1-yl)propoxy)-2'-methyl-[1,1'-biphenyl]-3-yl)-3,4-dihydroisoquinoline-2(1H)-carboxylate (70 mg, 0.12 mmol) was dissolved in MeOH (0.5 mL), 4M HCl/dioxane (0.5 mL) was added, and the reaction mixture was stirred at 50° C. for 1 hour. Purification by reverse phase preparative HPLC ($H_2O$/MeCN with 0.1% TFA) gave 6-(3'-(3-(2,2-dimethylazetidin-1-yl)propoxy)-2-chloro-2'-methyl-[1,1'-biphenyl]-3-yl)-1,2,3,4-tetrahydroisoquinoline as a bis-TFA salt. $^1$H-NMR (400 MHz, $(CD_3)_2SO$) δ 9.66 (br s, 1H), 9.10 (br s, 2H), 7.48 (t, J=7.6 Hz, 1H), 7.39 (dd, J=1.8, 7.6 Hz, 1H), 7.36-7.29 (m, 3H), 7.29-7.21 (m, 2H), 6.99 (d, J=8.2 Hz, 1H), 6.78 (d, J=7.5 Hz, 1H), 4.37-4.31 (m, 2H), 4.13-4.00 (m, 2H), 3.99-3.86 (m, 2H), 3.47-3.39 (m, 2H), 3.33-3.21 (m, 1H), 3.19-3.09 (m, 1H), 3.05 (t, J=6.3 Hz, 2H), 2.39-2.29 (m, 1H), 2.14-2.06 (m, 1H), 2.03-1.92 (m, 5H), 1.57 (s, 3H), 1.55 (s, 3H). MS: (ES) m/z calculated for $C_{30}H_{36}ClN_2O$ $[M+H]^+$ 475.3, found 475.3.

Example 9: 6-(3'-(3-(2,2-dimethylazetidin-1-yl)propoxy)-2-methoxy-2'-methyl-[1,1'-biphenyl]-3-yl)-1,2,3,4-tetrahydroisoquinoline

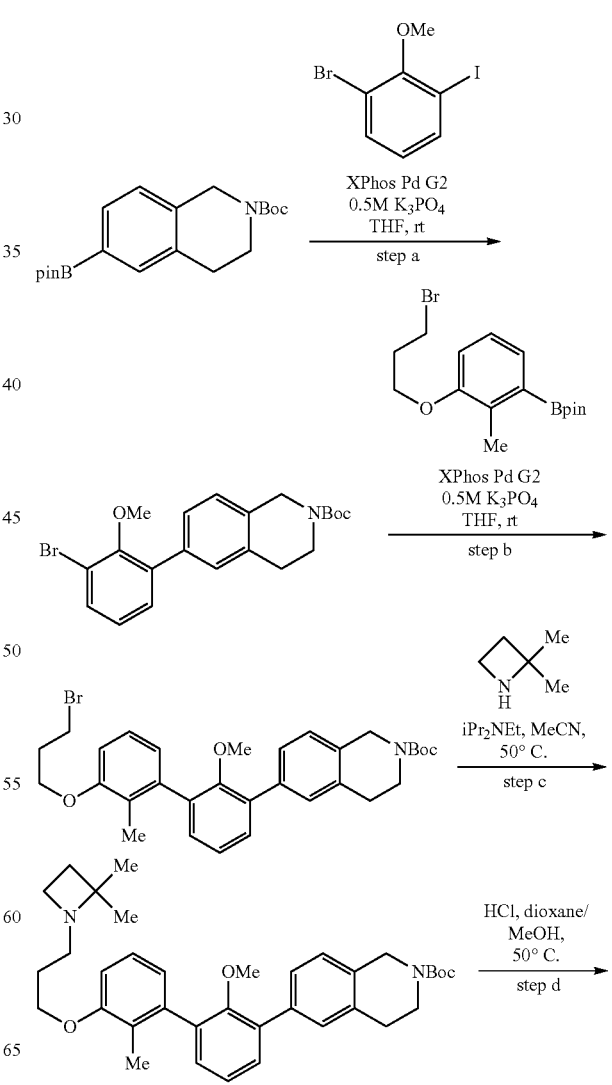

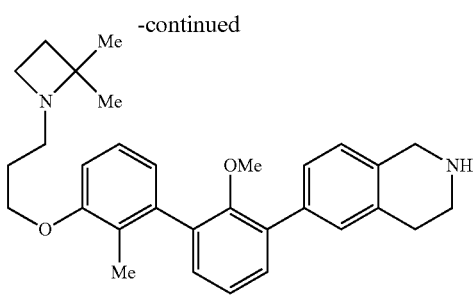

3.34-3.22 (m, 1H), 3.19-3.09 (m, 1H), 3.09-3.01 (m, 5H), 2.39-2.29 (m, 1H), 2.15-2.06 (m, 1H), 2.04-1.94 (m, 5H), 1.58 (s, 3H), 1.55 (s, 3H). MS: (ES) m/z calculated for $C_{31}H_{39}N_2O_2$ [M+H]$^+$ 471.3, found 471.4.

Example 10: 6-(3'-(3-(2,2-dimethylazetidin-1-yl)propoxy)-2'-methyl-2-vinyl-[1,1'-biphenyl]-3-yl)-1,2,3,4-tetrahydroisoquinoline

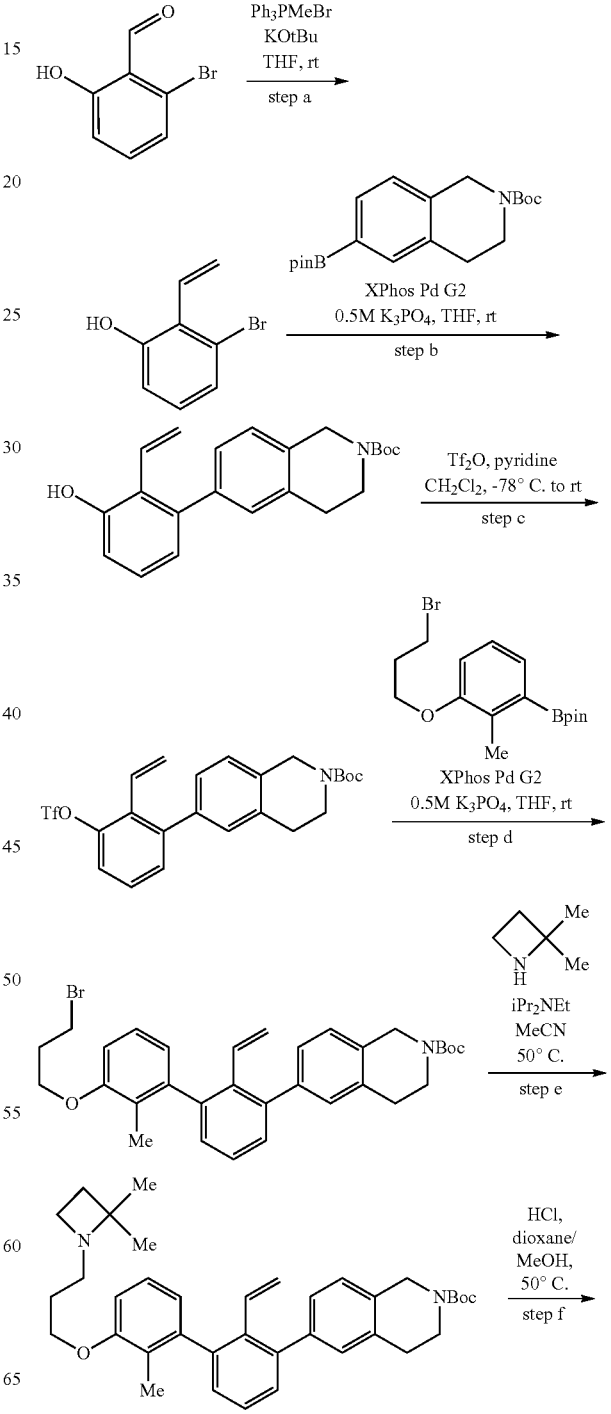

Step a: A mixture of 2-bromo-6-iodoanisole (250 mg, 0.80 mmol), tert-butyl 6-(4,4,5,5-tetramethyl-1,3,2-dioxaborolan-2-yl)-3,4-dihydroisoquinoline-2(1H)-carboxylate (287 mg, 0.80 mmol), THF (8 mL), and 0.5 M K$_3$PO$_4$ (8 mL) was degassed (N$_2$) for 5 minutes. XPhos Pd G2 (63 mg, 0.080 mmol) was added, and the reaction mixture was degassed (N$_2$) for an additional 5 minutes and stirred at room temperature overnight. The reaction mixture was diluted with H$_2$O (10 mL) and extracted with EtOAc (3×10 mL). The combined organic layers were washed with brine (10 mL), dried over MgSO$_4$, filtered, and concentrated. Purification by silica gel flash chromatography (0-100% CH$_2$Cl$_2$/hexanes) gave tert-butyl 6-(3-bromo-2-methoxyphenyl)-3,4-dihydroisoquinoline-2(1H)-carboxylate.

Step b: A mixture of tert-butyl 6-(3-bromo-2-methoxyphenyl)-3,4-dihydroisoquinoline-2(1H)-carboxylate (80 mg, 0.19 mmol), 2-(3-(3-bromopropoxy)-2-methylphenyl)-4,4,5,5-tetramethyl-1,3,2-dioxaborolane (128 mg, 0.29 mmol), THF (2 mL), and 0.5 M K$_3$PO$_4$ (2 mL) was degassed (N$_2$) for 5 minutes. XPhos Pd G2 (15 mg, 0.019 mmol) was added, and the reaction mixture was degassed (N$_2$) for an additional 5 minutes and stirred at room temperature overnight. The reaction mixture was diluted with H$_2$O (10 mL) and extracted with EtOAc (3×10 mL). The combined organic layers were washed with brine (10 mL), dried over MgSO$_4$, filtered, and concentrated. Purification by silica gel flash chromatography (0-100% CH$_2$Cl$_2$/hexanes, then 0-20% EtOAc/CH$_2$Cl$_2$) gave tert-butyl 6-(3'-(3-bromopropoxy)-2-methoxy-2'-methyl-[1,1'-biphenyl]-3-yl)-3,4-dihydroisoquinoline-2(1H)-carboxylate.

Step c: A solution of tert-butyl 6-(3'-(3-bromopropoxy)-2-methoxy-2'-methyl-[1,1'-biphenyl]-3-yl)-3,4-dihydroisoquinoline-2(1H)-carboxylate (60 mg, 0.11 mmol), 2,2-dimethylazetidine (19 mg, 0.22 mmol), and iPr$_2$NEt (58 µL, 0.33 mmol) in MeCN (1 mL) was stirred at 50° C. for 4 hours. The reaction mixture was cooled to room temperature and concentrated. Purification by silica gel flash chromatography (0-10% MeOH/CH$_2$Cl$_2$) gave tert-butyl 6-(2-methoxy-3'-(3-(2,2-dimethylazetidin-1-yl)propoxy)-2'-methyl-[1,1'-biphenyl]-3-yl)-3,4-dihydroisoquinoline-2(1H)-carboxylate.

Step d: tert-butyl 6-(2-methoxy-3'-(3-(2,2-dimethylazetidin-1-yl)propoxy)-2'-methyl-[1,1'-biphenyl]-3-yl)-3,4-dihydroisoquinoline-2(1H)-carboxylate (40 mg, 0.070 mmol) was dissolved in MeOH (0.5 mL), 4M HCl/dioxane (0.5 mL) was added, and the reaction mixture was stirred at 50° C. for 1 hour. Purification by reverse phase preparative HPLC (H$_2$O/MeCN with 0.1% TFA) gave 6-(3'-(3-(2,2-dimethylazetidin-1-yl)propoxy)-2-methoxy-2'-methyl-[1,1'-biphenyl]-3-yl)-1,2,3,4-tetrahydroisoquinoline as a bis-TFA salt. $^1$H-NMR (400 MHz, (CD$_3$)$_2$SO) δ 9.67 (br s, 1H), 9.09 (br s, 2H), 7.47-7.39 (m, 2H), 7.36 (dd, J=1.8, 7.6 Hz, 1H), 7.32-7.20 (m, 3H), 7.14 (dd, J=1.8, 7.5 Hz, 1H), 6.97 (d, J=8.4 Hz, 1H), 6.86 (d, J=7.6 Hz, 1H), 4.37-4.30 (m, 2H), 4.14-4.01 (m, 2H), 3.99-3.88 (m, 2H), 3.47-3.41 (m, 2H),

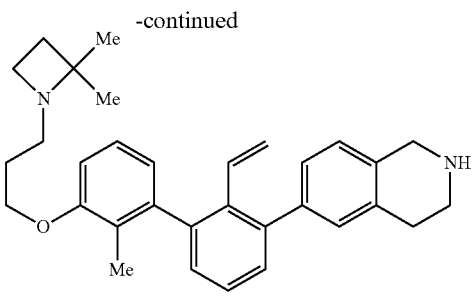

Step a: Methyltriphenylphosphonium bromide (4.47 g, 12.5 mmol) was dissolved in THF (20 mL), and KOtBu (1.0 M solution in THF, 12.5 mL, 12.5 mmol) was added. The mixture was stirred at room temperature for 1 hour. A solution of 2-bromo-6-hydroxy-benzaldehyde (1.01 g, 5.0 mmol) in THF (5 mL) was added dropwise, and the reaction mixture was stirred at room temperature overnight. The reaction mixture was quenched with 1 M HCl (50 mL) and extracted with EtOAc (3×50 mL). The combined organic layers were washed with brine (50 mL), dried over MgSO$_4$, filtered, and concentrated. Purification by silica gel flash chromatography (0-50% EtOAc/hexanes) gave 3-bromo-2-vinylphenol.

Step b: A mixture of 3-bromo-2-vinylphenol (299 mg, 1.5 mmol), tert-butyl 6-(4,4,5,5-tetramethyl-1,3,2-dioxaborolan-2-yl)-3,4-dihydroisoquinoline-2(1H)-carboxylate (647 mg, 1.8 mmol), THF (15 mL), and 0.5 M K$_3$PO$_4$ (15 mL) was degassed (N$_2$) for 10 minutes. XPhos Pd G2 (118 mg, 0.15 mmol) was added, and the reaction mixture was degassed (N$_2$) for an additional 10 minutes and stirred at room temperature overnight. The reaction mixture was diluted with H$_2$O (20 mL) and extracted with EtOAc (3×20 mL). The combined organic layers were washed with brine (20 mL), dried over MgSO$_4$, filtered, and concentrated. Purification by silica gel flash chromatography (0-60% EtOAc/hexanes) gave tert-butyl 6-(3-hydroxy-2-vinylphenyl)-3,4-dihydroisoquinoline-2(1H)-carboxylate.

Step c: tert-butyl 6-(3-hydroxy-2-vinylphenyl)-3,4-dihydroisoquinoline-2(1H)-carboxylate (175 mg, 0.50 mmol) was dissolved in CH$_2$Cl$_2$ (5 mL). The solution was stirred at −78° C., and pyridine (0.5 mL) was added, followed by the dropwise addition of trifluoromethanesulfonic anhydride (0.17 mL, 1.0 mmol). The reaction mixture was stirred at room temperature for 2 hours. The reaction mixture was quenched with sat. NaHCO$_3$ (10 mL). The layers were separated, and the aqueous layer was extracted with CH$_2$Cl$_2$ (2×10 mL). The combined organic layers were washed with brine (10 mL), dried over MgSO$_4$, filtered, and concentrated. Purification by silica gel flash chromatography (0-30% EtOAc/hexanes) gave tert-butyl 6-(3-(((trifluoromethyl)sulfonyl)oxy)-2-vinylphenyl)-3,4-dihydroisoquinoline-2(1H)-carboxylate.

Step d: A mixture of tert-butyl 6-(3-(((trifluoromethyl)sulfonyl)oxy)-2-vinylphenyl)-3,4-dihydroisoquinoline-2(1H)-carboxylate (90 mg, 0.19 mmol), 2-(3-(3-bromopropoxy)-2-methylphenyl)-4,4,5,5-tetramethyl-1,3,2-dioxaborolane (102 mg, 0.23 mmol), THF (2 mL), and 0.5 M K$_3$PO$_4$ (2 mL) was degassed (N$_2$) for 5 minutes. XPhos Pd G2 (15 mg, 0.019 mmol) was added, and the reaction mixture was degassed (N$_2$) for an additional 5 minutes and stirred at room temperature overnight. The reaction mixture was diluted with H$_2$O (10 mL) and extracted with EtOAc (3×10 mL). The combined organic layers were washed with brine (10 mL), dried over MgSO$_4$, filtered, and concentrated. Purification by silica gel flash chromatography (0-30% EtOAc/hexanes) gave tert-butyl 6-(3'-(3-bromopropoxy)-2'-methyl-2-vinyl-[1,1'-biphenyl]-3-yl)-3,4-dihydroisoquinoline-2(1H)-carboxylate.

Step e: A solution of tert-butyl 6-(3'-(3-bromopropoxy)-2'-methyl-2-vinyl-[1,1'-biphenyl]-3-yl)-3,4-dihydroisoquinoline-2(1H)-carboxylate (80 mg, 0.14 mmol), 2,2-dimethylazetidine (24 mg, 0.28 mmol), and iPr$_2$NEt (73 µL, 0.42 mmol) in MeCN (2 mL) was stirred at 50° C. for 3 hours. The reaction mixture was cooled to room temperature and concentrated. Purification by silica gel flash chromatography (0-10% MeOH/CH$_2$Cl$_2$) gave tert-butyl 6-(3'-(3-(2,2-dimethylazetidin-1-yl)propoxy)-2'-methyl-2-vinyl-[1,1'-biphenyl]-3-yl)-3,4-dihydroisoquinoline-2(1H)-carboxylate.

Step f: tert-butyl 6-(3'-(3-(2,2-dimethylazetidin-1-yl)propoxy)-2'-methyl-2-vinyl-[1,1'-biphenyl]-3-yl)-3,4-dihydroisoquinoline-2(1H)-carboxylate (55 mg, 0.097 mmol) was dissolved in MeOH (0.5 mL), 4M HCl/dioxane (0.5 mL) was added, and the reaction mixture was stirred at 50° C. for 1 hour. Purification by reverse phase preparative HPLC (H$_2$O/MeCN with 0.1% TFA) gave 6-(3'-(3-(2,2-dimethylazetidin-1-yl)propoxy)-2'-methyl-2-vinyl-[1,1'-biphenyl]-3-yl)-1,2,3,4-tetrahydroisoquinoline as a bis-TFA salt. $^1$H-NMR (400 MHz, (CD$_3$)$_2$SO) δ 9.51 (br s, 1H), 9.01 (br s, 2H), 7.39 (t, J=7.6 Hz, 1H), 7.28-7.17 (m, 5H), 7.10 (d, J=7.9 Hz, 2H), 6.94 (d, J=8.3 Hz, 1H), 6.77 (d, J=7.7 Hz, 1H), 6.30 (dd, J=11.6, 17.8 Hz, 1H), 4.93 (dd, J=1.6, 11.6 Hz, 1H), 4.59 (dd, J=1.6, 17.8 Hz, 1H), 4.35-4.29 (m, 2H), 4.12-3.98 (m, 2H), 3.97-3.87 (m, 2H), 3.32-3.18 (m, 2H), 3.18-3.07 (m, 2H), 3.03 (t, J=6.4 Hz, 2H), 2.38-2.28 (m, 1H), 2.15-2.05 (m, 1H), 2.02-1.92 (m, 2H), 1.87 (s, 3H), 1.56 (s, 3H), 1.54 (s, 3H). MS: (ES) m/z calculated for C$_{32}$H$_{39}$N$_2$O [M+H]$^+$ 467.3, found 467.3.

Example 11: 2,2'-(((3,3'''-difluoro-5,5'''-dimethoxy-2',2''-dimethyl-[1,1':3',1'':3'',1'''-quaterphenyl]-4,4'''-diyl)bis(methylene))bis(azanediyl))bis(ethan-1-ol)

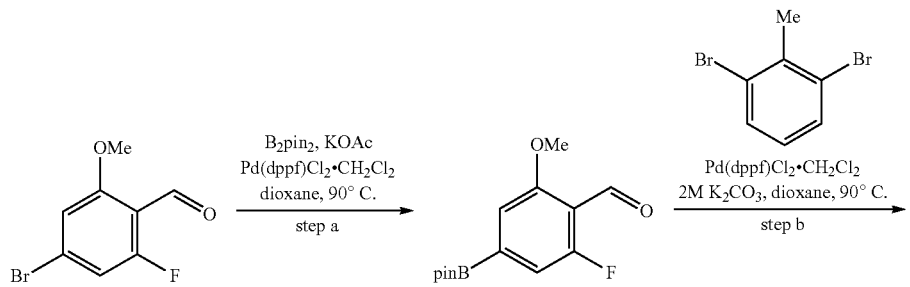

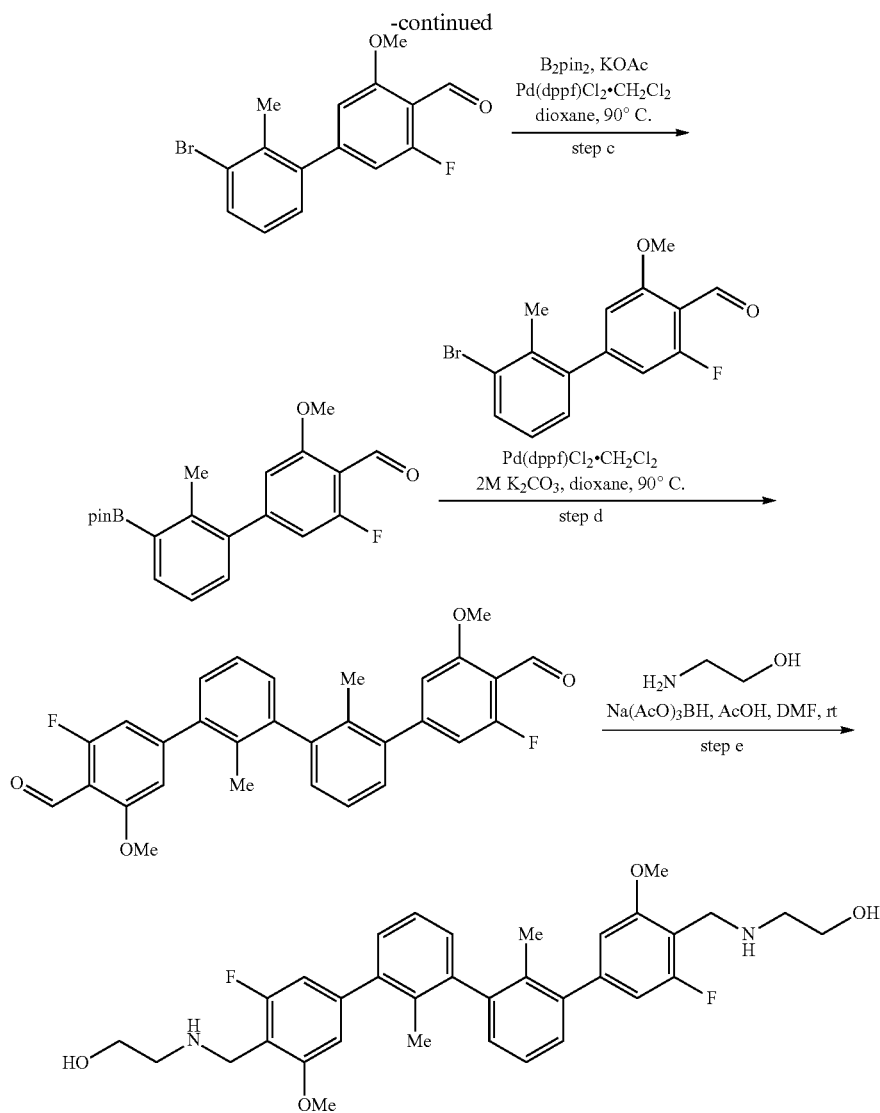

Step a: In a 2 L round-bottom flask a mixture was prepared containing 4-bromo-2-fluoro-6-methoxybenzaldehyde (22 g, 94 mmol), bis(pinacolato)diboron (27 g, 106 mmol), [1,1'-bis(diphenylphosphino)ferrocene]dichloropalladium(II) complex with dichloromethane (7.4 g, 9.1 mmol), potassium acetate (32 g, 330 mmol) and dioxane (460 mL). The mixture was thoroughly degassed ($N_2$) for 1 hour, then stirred under $N_2$ at 90° C. for 19 h. Afterwards, dioxane was removed under reduced pressure, the residue was taken up in ethyl acetate and water, and filtered through Celite®. The aqueous phase was separated and discarded. The organic phase was washed with brine, adsorbed onto silica gel, and purified by silica gel flash chromatography (6-15% EtOAc/hexanes) to give 2-fluoro-6-methoxy-4-(4,4,5,5-tetramethyl-1,3,2-dioxaborolan-2-yl)benzaldehyde.

Step b: In a 200 mL round-bottom flask were combined 2,6-dibromotoluene (6.2 g, 25 mmol), 2-fluoro-6-methoxy-4-(4,4,5,5-tetramethyl-1,3,2-dioxaborolan-2-yl)benzaldehyde (4.0 g, 14 mmol), [1,1'-bis(diphenylphosphino)ferrocene]dichloropalladium(II) complex with dichloromethane (1.1 g, 1.3 mmol), 2 M $K_2CO_3$ (20 mL, 40 mmol) and dioxane (50 mL). The mixture was thoroughly degassed ($N_2$) for 45 minutes, then stirred under $N_2$ at 90° C. for 2.5 h. After the reaction mixture was cooled to room temperature, it was diluted with diethyl ether and ethyl acetate, and the aqueous phase was separated. The resulting organic phase was purified by silica gel flash chromatography (4-16% EtOAc/hexanes) to afford 3'-bromo-3-fluoro-5-methoxy-2'-methyl-[1,1'-biphenyl]-4-carbaldehyde.

Step c: In a 100 mL round-bottom flask were combined 3'-bromo-3-fluoro-5-methoxy-2'-methyl-[1,1'-biphenyl]-4-carbaldehyde (1.5 g, 4.6 mmol), bis(pinacolato)diboron (1.9 g, 7.3 mmol), [1,1'-bis(diphenylphosphino)ferrocene]dichloropalladium(II) complex with dichloromethane (510 mg, 0.62 mmol), potassium acetate (1.5 g, 15 mmol), and dioxane (55 mL). The mixture was degassed ($N_2$) and stirred under $N_2$ at 90° C. for 16 h. After cooling to room temperature, the reaction mixture was diluted with ethyl acetate, ether and water, and filtered through Celite®. The aqueous phase was separated and discarded, and the remaining organic phase was purified by silica gel flash chromatography (8-14% EtOAc/hexanes) to obtain 3-fluoro-5-methoxy-2'-methyl-3'-(4,4,5,5-tetramethyl-1,3,2-dioxaborolan-2-yl)-[1,1'-biphenyl]-4-carbaldehyde.

Step d: To a mixture of 3'-bromo-3-fluoro-5-methoxy-2'-methyl-[1,1'-biphenyl]-4-carbaldehyde (500 mg, 1.5 mmol), 3-fluoro-5-methoxy-2'-methyl-3'-(4,4,5,5-tetramethyl-1,3,2-dioxaborolan-2-yl)-[1,1'-biphenyl]-4-carbaldehyde (930 mg, 2.5 mmol), 2 M $K_2CO_3$ (2.0 mL, 4.0 mmol), and dioxane (12 mL) was added [1,1'-bis(diphenylphosphino)ferrocene]-dichloropalladium(II) complex with dichloromethane (120 mg, 0.15 mmol). The mixture was degassed ($N_2$) and stirred at 90° C. for 5 h. After cooling to room temperature, the mixture was diluted with ethyl acetate, and the aqueous phase was separated and discarded. The organic phase was purified by silica gel flash chromatography (4 to 100% EtOAc/hexanes) to obtain 3,3'''-difluoro-5,5'''-dimethoxy-2',2''-dimethyl-[1,1':3',1'':3'',1'''-quaterphenyl]-4,4'''-dicarbaldehyde.

Step e: To a solution of 3,3'''-difluoro-5,5'''-dimethoxy-2',2''-dimethyl-[1,1':3',1'':3'',1'''-quaterphenyl]-4,4'''-dicarbaldehyde (70 mg, 0.14 mmol) and acetic acid (0.050 mL, 0.87 mmol) in DMF (2 mL) was added 2-aminoethanol (0.087 mL, 1.4 mmol). After stirring at room temperature for 10 minutes, $Na(AcO)_3BH$ (180 mg, 0.85 mmol) was added and the mixture was stirred at room temperature for an additional 1.5 h. The reaction mixture was diluted with 2:1 chloroform:isopropanol and water, and the aqueous layer was separated and discarded. The resulting organic phase was concentrated under reduced pressure, and the resulting residue was purified by reverse phase preparative HPLC ($H_2O$/MeCN with 0.1% TFA) to give 2,2'-(((3,3'''-difluoro-5,5'''-dimethoxy-2',2''-dimethyl-[1,1':3',1'':3'',1'''-quaterphenyl]-4,4'''-diyl)bis(methylene))bis(azanediyl))bis(ethan-1-ol). $^1$H-NMR (400 MHz, $CD_3OD$) δ 7.34 (t, J=7.6 Hz, 2H), 7.25 (d, J=7.5 Hz, 2H), 7.18 (d, J=7.5 Hz, 2H), 6.95-6.83 (m, 4H), 4.36 (s, 4H), 3.98 (s, 6H), 3.88-3.81 (m, 4H), 3.19 (t, J=5.2 Hz, 4H), 1.97 (s, 6H). MS: (ES) m/z calculated for $C_{34}H_{39}F_2N_2O_4$ [M+H]+ 577.3, found 577.2.

Example 12: 2-(((4'''-((dimethylamino)methyl)-3,3'''-difluoro-5,5'''-dimethoxy-2',2''-dimethyl-[1,1':3',1'':3'',1'''-quaterphenyl]-4-yl)methyl)amino)ethan-1-ol

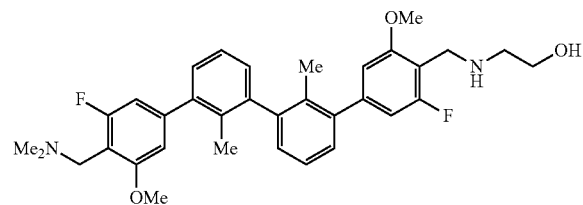 [SMILES: COc1cc(-c2cccc(-c3cccc(-c4cc(F)c(CN(C)C)c(OC)c4)c3C)c2C)cc(F)c1CNCCO]

This compound was isolated as a side product during the preparation of Example 11. $^1$H-NMR (400 MHz, $CD_3OD$) δ 7.37-7.15 (m, 6H), 6.98-6.83 (m, 4H), 4.43 (s, 2H), 4.36 (s, 2H), 3.99 (s, 3H), 3.98 (s, 3H), 3.88-3.81 (m, 2H), 3.19 (t, J=5.3 Hz, 2H), 2.93 (s, 6H), 1.98 (s, 3H), 1.97 (s, 3H). MS: (ES) m/z calculated for $C_{34}H_{39}F_2N_2O_3$ [M+H]$^+$ 561.3, found 561.2.

Example 13: N-(4''-(aminomethyl)-3''-fluoro-5''-methoxy-2,2'-dimethyl-[1,1':3',1''-terphenyl]-3-yl)piperidin-4-amine

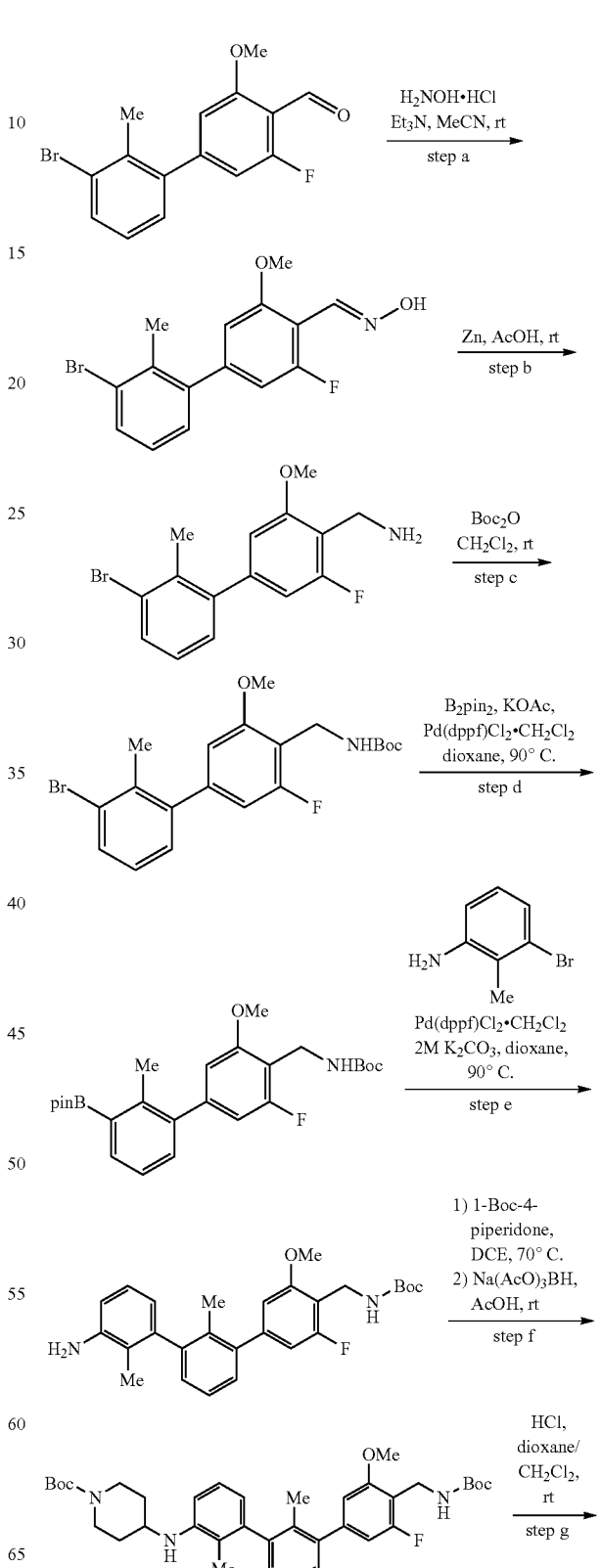

-continued

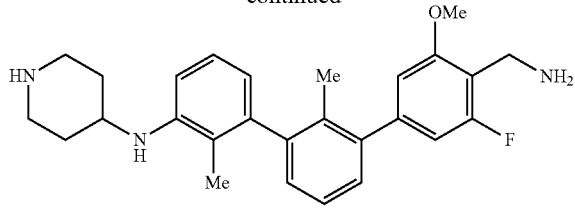

Step a: To a stirred solution of 3'-bromo-3-fluoro-5-methoxy-2'-methyl-[1,1'-biphenyl]-4-carbaldehyde (5.0 g, 15 mmol) in acetonitrile (100 mL) was added hydroxylamine hydrochloride (1.6 g, 24 mmol) and triethylamine (3.3 mL, 24 mmol). The mixture was stirred at room temperature for 12 h, then poured into saturated sodium bicarbonate (300 mL). The precipitated 3'-bromo-3-fluoro-5-methoxy-2'-methyl-[1,1'-biphenyl]-4-carbaldehyde oxime was collected by filtration, partially dried, and used in the next step without purification.

Step b: 3'-bromo-3-fluoro-5-methoxy-2'-methyl-[1,1'-biphenyl]-4-carbaldehyde oxime was stirred in acetic acid to form a slurry. To this was added zinc dust (8.0 g, 120 mmol), and the mixture was stirred at room temperature for 1.5 h. The reaction mixture was filtered through Celite® to remove zinc, and the acetic acid was removed under reduced pressure. The residue was taken up in 2:1 chloroform:isopropanol and a combination of saturated sodium bicarbonate, 6 M NaOH, and water. The aqueous phase was separated and the organic phase was washed with brine and concentrated to give a crude viscous oil of (3'-bromo-3-fluoro-5-methoxy-2'-methyl-[1,1'-biphenyl]-4-yl)methanamine (5.3 g).

Step c: To a solution of the oily residue from the previous step in dichloromethane (80 mL) was added di-tert-butyl dicarbonate (6.4 g, 29 mmol). After stirring at room temperature for 2 d, the dichloromethane was removed under reduced pressure and the residue was purified by silica gel flash chromatography (4-80% EtOAc/hexane) to afford tert-butyl ((3'-bromo-3-fluoro-5-methoxy-2'-methyl-[1,1'-biphenyl]-4-yl)methyl)carbamate.

Step d: In a 500 mL round-bottom flask were combined tert-butyl ((3'-bromo-3-fluoro-5-methoxy-2'-methyl-[1,1'-biphenyl]-4-yl)methyl)carbamate (5.3 g, 13 mmol), bis(pinacolato)-diboron (4.0 g, 16 mmol), [1,1'-bis(diphenylphosphino)ferrocene]dichloropalladium(II) complex with dichloromethane (1.3 g, 1.6 mmol), potassium acetate (3.2 g, 33 mmol), and dioxane (100 mL). The mixture was degassed ($N_2$) and stirred under $N_2$ at 90° C. for 3 h. After cooling to room temperature, approximately half of the dioxane was removed in vacuo, and the resulting mixture was diluted with ethyl acetate and water and filtered through Celite®. The organic phase was separated, washed with brine, and purified by silica gel flash chromatography (10-40% EtOAc/hexane) to afford tert-butyl ((3-fluoro-5-methoxy-2'-methyl-3'-(4,4,5,5-tetramethyl-1,3,2-dioxaborolan-2-yl)-[1,1'-biphenyl]-4-yl)methyl)carbamate.

Step e: In a 40 mL vial were combined tert-butyl ((3-fluoro-5-methoxy-2'-methyl-3'-(4,4,5,5-tetramethyl-1,3,2-dioxaborolan-2-yl)-[1,1'-biphenyl]-4-yl)methyl)carbamate (700 mg, 1.5 mmol), 3-bromo-2-methylaniline (340 mg, 1.8 mmol), [1,1'-bis(diphenylphosphino)-ferrocene]dichloropalladium(II) complex with dichloromethane (140 mg, 0.17 mmol), 2M $K_2CO_3$ (2.0 mL, 4.0 mmol) and dioxane (12 mL). The mixture was thoroughly degassed ($N_2$) before stirring at 90° C. for 5 h. After cooling, the reaction mixture was diluted with the addition of brine and ether. The aqueous phase was separated and the organic phase was purified by silica gel flash chromatography (10-34% EtOAc/hexane) to obtain tert-butyl ((3"-amino-3-fluoro-5-methoxy-2',2"-dimethyl-[1,1':3',1"-terphenyl]-4-yl)methyl)carbamate.

Step f: To a solution of tert-butyl ((3"-amino-3-fluoro-5-methoxy-2',2"-dimethyl-[1,1:3',1"-terphenyl]-4-yl)methyl)carbamate (40 mg, 0.089 mmol) in DCE (1 mL) was added 1-Boc-4-piperidone (24 mg, 0.12 mmol) and the reaction mixture was stirred at 70° C. for 1 h. After cooling to room temperature, $Na(AcO)_3BH$ (87 mg, 0.41 mmol) was added, followed by acetic acid (0.010 mL, 0.17 mmol). After stirring at room temperature for 2.5 d, the reaction mixture was taken up in chloroform and water. The aqueous phase was separated, and the organic phase was purified by silica gel flash chromatography (4-30% EtOAc/hexane) to obtain tert-butyl 4-((4"-(((tert-butoxycarbonyl)amino)methyl)-3"-fluoro-5"-methoxy-2,2'-dimethyl-[1,1':3',1"-terphenyl]-3-yl)amino)piperidine-1-carboxylate.

Step g: To a solution of tert-butyl 4-((4"-(((tert-butoxycarbonyl)amino)methyl)-3"-fluoro-5"-methoxy-2,2'-dimethyl-[1,1':3',1"-terphenyl]-3-yl)amino)piperidine-1-carboxylate (45 mg, 0.071 mmol) in dichloromethane (1 mL) was added 4M HCl in dioxane (0.40 mL, 1.6 mmol). The reaction mixture was stirred at room temperature for 4 hours. Solvents were removed in vacuo, and the resulting residue was purified by reverse phase preparative HPLC ($H_2O$/MeCN with 0.1% TFA as eluent) to give N-(4"-(aminomethyl)-3"-fluoro-5"-methoxy-2,2'-dimethyl-[1,1':3',1"-terphenyl]-3-yl)piperidin-4-amine. $^1$H-NMR (400 MHz, $CD_3OD$) δ 7.29 (t, J=8.0 Hz, 1H), 7.20 (dd, J=1.5, 8.0 Hz, 1H), 7.15-7.06 (m, 3H), 6.82 (dd, J=1.4, 10.0 Hz, 1H), 6.77 (d, J=8.4 Hz, 1H), 6.52 (d, J=7.2 Hz, 1H), 4.22 (s, 2H), 3.97 (s, 3H), 3.80-3.69 (m, 1H), 3.48 (d, J=13.4 Hz, 2H), 3.18 (t, J=12.1 Hz, 2H), 2.31 (d, J=14.2 Hz, 2H), 1.91 (s, 3H), 1.88 (s, 3H), 1.83-1.68 (m, 2H). MS: (ES) m/z calculated for $C_{27}H_{33}FN_3O$ [M+H]$^+$ 434.3, found 434.2.

Example 14: 1,1'-((3,3'''-difluoro-5,5'''-dimethoxy-2',2''-dimethyl-[1,1':3',1":3",1'''-quaterphenyl]-4,4'''-diyl)bis(methylene))bis(piperidin-4-ol)

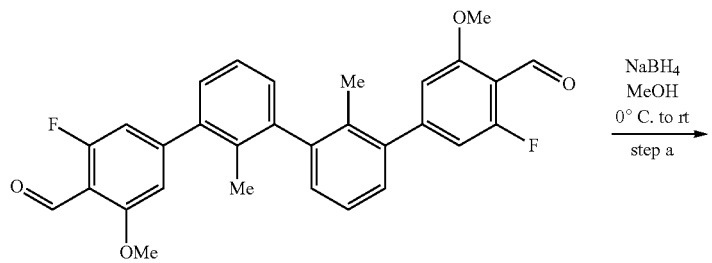

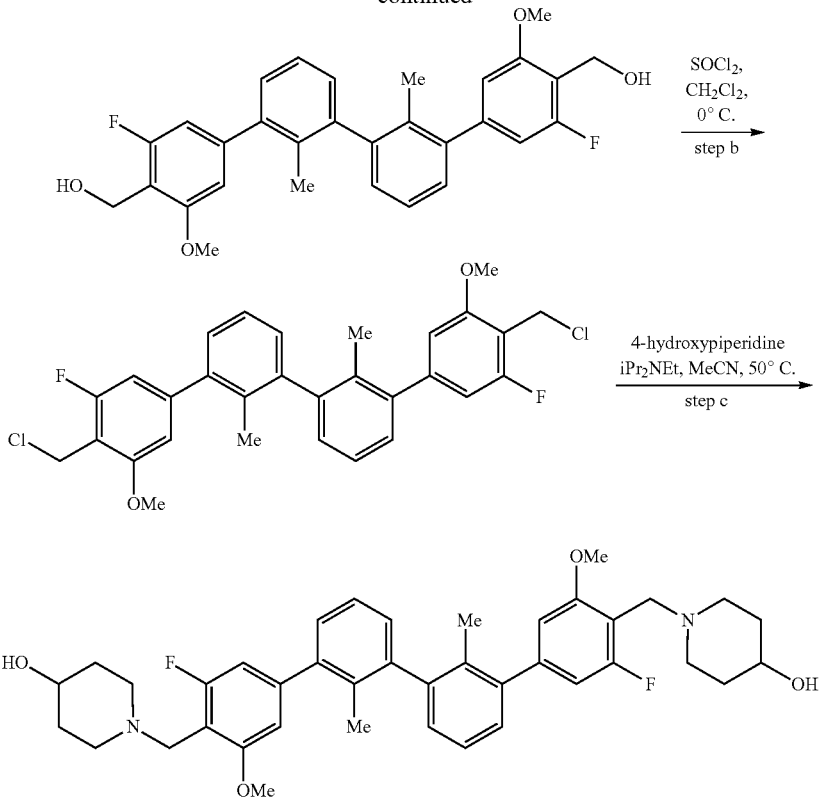

Step a: 3,3'''-difluoro-5,5'''-dimethoxy-2',2''-dimethyl-[1,1':3',1'':3'',1'''-quaterphenyl]-4,4'''-dicarbaldehyde (97 mg, 0.20 mmol) was dissolved in MeOH (2 mL). The solution was stirred at 0° C., and sodium borohydride (30 mg, 0.80 mmol) was added slowly. The reaction mixture was stirred for 2.5 hours while allowing to warm to room temperature gradually. The reaction mixture was quenched with sat. NaHCO$_3$ (10 mL) and extracted with CH$_2$Cl$_2$ (3×10 mL). The combined organic layers were washed with brine (10 mL), dried over MgSO$_4$, filtered, and concentrated. Purification by silica gel flash chromatography gave (3,3'''-difluoro-5,5'''-dimethoxy-2',2''-dimethyl-[1,1':3',1'':3'',1'''-quaterphenyl]-4,4'''-diyl)dimethanol.

Step b: (3,3'''-difluoro-5,5'''-dimethoxy-2',2''-dimethyl-[1,1':3',1'':3'',1'''-quaterphenyl]-4,4'''-diyl)dimethanol (38 mg, 0.077 mmol) was dissolved in CH$_2$Cl$_2$ (2 mL). The solution was stirred at 0° C., and thionyl chloride (34 µL, 0.46 mmol) was added dropwise. The reaction mixture was stirred at 0° C. for 1 hour. The reaction mixture was concentrated to yield 4,4'''-bis(chloromethyl)-3,3'''-difluoro-5,5'''-dimethoxy-2',2''-dimethyl-1,1':3',1'':3'',1'''-quaterphenyl, which was used without further purification.

Step c: A mixture of 4,4'''-bis(chloromethyl)-3,3'''-difluoro-5,5'''-dimethoxy-2',2''-dimethyl-1,1':3',1'':3'',1'''-quaterphenyl (40 mg, 0.076 mmol), 4-hydroxypiperidine (47 mg, 0.46 mmol), iPr$_2$NEt (0.13 mL, 0.76 mmol), and MeCN (1 mL) was stirred at 50° C. overnight. Purification by reverse phase preparative HPLC (H$_2$O/MeCN with 0.1% TFA) gave 1,1'-(((3,3'''-difluoro-5,5'''-dimethoxy-2',2''-dimethyl-[1,1':3',1'':3'',1'''-quaterphenyl]-4,4'''-diyl)bis(methylene))bis(piperidin-4-ol). $^1$H-NMR (400 MHz, CD$_3$OD) δ 7.32 (t, J=7.6 Hz, 2H), 7.24 (d, J=6.6 Hz, 2H), 7.15 (d, J=7.3 Hz, 2H), 6.80 (s, 2H), 6.73 (d, J=9.7 Hz, 2H), 3.88 (s, 6H), 3.74 (br s, 4H), 3.61 (br s, 2H), 2.96-2.87 (m, 4H), 2.43-2.32 (m, 4H), 1.98 (s, 6H), 1.90-1.80 (m, 4H), 1.66-1.54 (m, 4H). MS: (ES) m/z calculated for C$_{40}$H$_{47}$F$_2$N$_2$O$_4$[M+H]$^+$ 657.3, found 657.2.

Example 15: 4,4'-(((3,3'''-difluoro-5,5'''-dimethoxy-2',2''-dimethyl-[1,1':3',1'':3'',1'''-quaterphenyl]-4,4'''-diyl)bis(methylene))bis(azanediyl))dibutyric acid

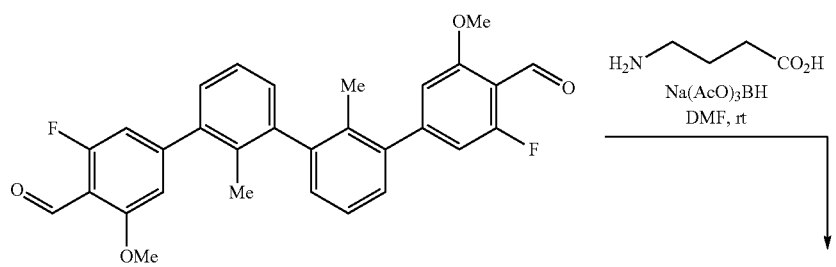

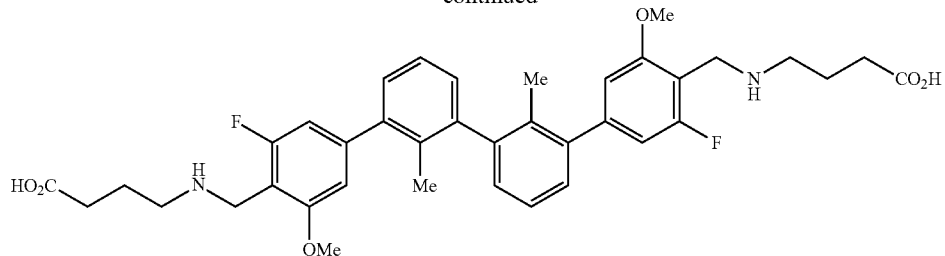

A solution of 3,3'''-difluoro-5,5'''-dimethoxy-2',2''-dimethyl-[1,1':3',1'':3'',1'''-quaterphenyl]-4,4'''-dicarbaldehyde (36 mg, 0.074 mmol) and γ-aminobutyric acid (46 mg, 0.44 mmol) was stirred in DMF (3 mL) at room temperature for 2 h before Na(AcO)$_3$BH (50 mg, 0.22 mmol) was added in portions over 5 min. The reaction mixture was left to stir overnight at room temperature. The majority of DMF was removed in vacuo, and the crude material was re-diluted in MeOH and filtered. The filtrate was purified by reverse phase preparative HPLC (H$_2$O/MeCN with 0.1% TFA) to obtain 4,4'-(((3,3'''-difluoro-5,5'''-dimethoxy-2',2''-dimethyl-[1,1':3',1'':3'',1'''-quaterphenyl]-4,4'''-diyl)bis(methylene))bis(azanediyl))dibutyric acid. MS: (ES) m/z calculated for $C_{38}H_{43}F_2N_2O_6[M+H]^+$ 661.3, found 661.2. $^1$H-NMR (400 MHz, CD$_3$OD) δ 7.34 (t, J=7.6 Hz, 2H), 7.25 (d, J=7.6 Hz, 2H), 7.22-7.13 (m, 2H), 6.92 (s, 2H), 6.90-6.82 (m, 2H), 4.33 (d, J=1.2 Hz, 4H), 3.98 (s, 6H), 3.23-3.09 (m, 4H), 2.49 (t, J=6.9 Hz, 4H), 2.05-1.98 (m, 4H), 1.98 (s, 6H).

Example 16: (3''-(3-((2R,5R)-2,5-dimethylpyrrolidin-1-yl)propoxy)-2',2''-dimethyl-[1,1':3',1''-terphenyl]-4-yl)methanamine 5R)-2,5-dimethylpyrrolidine hydrochloride (74 mg, 0.55 mmol) in MeCN (2 mL) was slowly added iPr$_2$NEt (0.30 mL, 1.7 mmol). The mixture was sonicated for a few minutes, heated to 50° C., and stirred for 18 h. After incomplete reaction, a catalytic amount of sodium iodide (3 mg) was added, and the solution was stirred for an additional 8 h at 50° C. The reaction mixture was concentrated. The crude material was purified by silica gel flash chromatography (0-5% MeOH/CH$_2$Cl$_2$) to obtain (2R,5R)-1-(3-((3'-bromo-2,2'-dimethyl-[1,1'-biphenyl]-3-yl)oxy)propyl)-2,5-dimethylpyrrolidine.

Step b: To a biphasic mixture of (2R,5R)-1-(3-((3'-bromo-2,2'-dimethyl-[1,1'-biphenyl]-3-yl)oxy)propyl)-2,5-dimethylpyrrolidine (38 mg, 0.091 mmol) and 4-(aminomethyl)phenylboronic acid hydrochloride (34 mg, 0.18 mmol) in 0.5 M K$_3$PO$_4$ (0.90 mL 0.46 mmol) and THF (2 mL) was added XPhos Pd G2 (14 mg, 0.018 mmol). The reaction mixture was heated to 50° C. for 12 h. The reaction mixture was allowed to cool to room temperature, and the organic layer was separated, filtered, and purified by reverse phase preparative HPLC (H$_2$O/MeCN with 0.1% TFA) to obtain (3''-(3-((2R,5R)-2,5-dimethylpyrrolidin-1-yl)

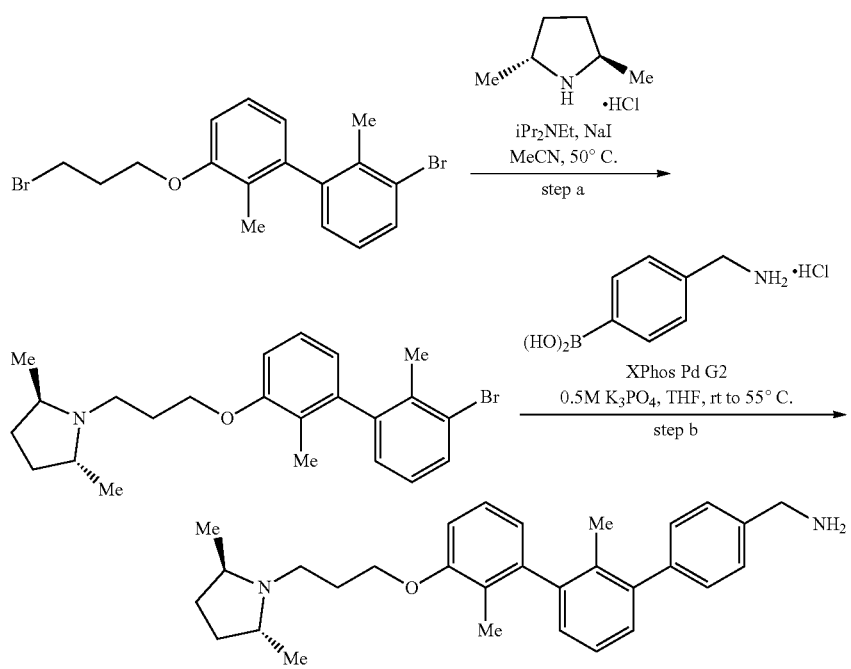

Step a: To a solution of 3-bromo-3'-(3-bromopropoxy)-2,2'-dimethyl-1,1'-biphenyl (170 mg, 0.42 mmol) and (2R, propoxy)-2',2''-dimethyl-[1,1':3',1''-terphenyl]-4-yl)methanamine. MS: (ES) m/z calculated for $C_{30}H_{39}N_2O\ [M+H]^+$ 443.3, found 443.2. ¹H-NMR (400 MHz, CDCl₃) δ 8.70-8.10 (br s, 2H), 7.40 (d, J=8.0 Hz, 2H), 7.36-7.29 (m, 2H), 7.21-7.04 (m, 4H), 6.83-6.66 (m, 2H), 4.15-3.66 (m, 4H), 3.47-3.22 (m, 2H), 3.22-2.91 (m, 2H), 2.34-2.20 (m, 2H), 2.19 (s, 2H), 1.90 (s, 3H), 1.82 (d, J=3.0 Hz, 3H), 1.53 (d, J=6.6 Hz, 2H), 1.30 (d, J=6.9 Hz, 3H), 1.27 (dd, J=6.9, 8.6 Hz, 3H).

Example 17: (3-fluoro-5-methoxy-2',2"-dimethyl-[1,1':3',1":3",1'''-quaterphenyl]-4,4'''-diyl)dimethanamine

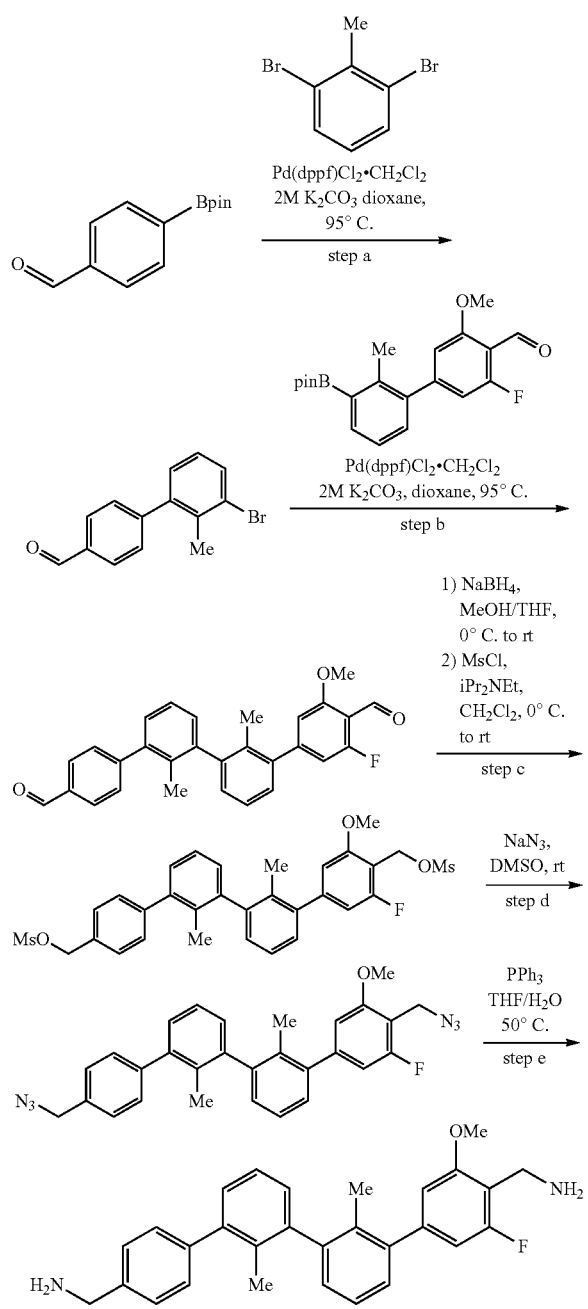

Step a: To a mixture of 1,3-dibromo-2-methylbenzene (1.6 g, 6.5 mmol), 4-(4,4,5,5-tetramethyl-1,3,2-dioxaborolan-2-yl)benzaldehyde (1.0 g, 4.3 mmol), and 2 M K₂CO₃ (6.4 mL, 12.9 mmol) in dioxane (30 mL) was added [1,1'-bis(diphenylphosphino)ferrocene]-dichloropalladium(II) complex with dichloromethane (528 mg, 0.7 mmol). The reaction mixture was degassed (N₂) for 2 min and stirred under N₂ at 95° C. for 5 hours. The reaction mixture was diluted with EtOAc and filtered through Celite®. The filtrate was washed with brine, dried over MgSO₄, filtered, and concentrated. Purification by silica gel flash chromatography (5-40% EtOAc/hexane) gave 3'-bromo-2'-methyl-[1,1'-biphenyl]-4-carbaldehyde. ¹H-NMR (400 MHz, CDCl₃) δ 10.07 (s, 1H), 7.95 (dd, J=6.3, 8.1 Hz, 2H), 7.90-7.68 (m, 1H), 7.67-7.37 (m, 2H), 7.22-7.07 (m, 2H), 2.30 (s, 3H).

Step b: To a mixture of 3'-bromo-2'-methyl-[1,1'-biphenyl]-4-carbaldehyde (223 mg, 0.81 mmol), 3-fluoro-5-methoxy-2'-methyl-3'-(4,4,5,5-tetramethyl-1,3,2-dioxaborolan-2-yl)-[1,1'-biphenyl]-4-carbaldehyde (200 mg, 0.54 mmol), and 2 M K₂CO₃ (0.81 mL, 1.62 mmol) in dioxane (4 mL) was added [1,1'-bis(diphenylphosphino)ferrocene]dichloropalladium(II) complex with dichloromethane (66 mg, 0.08 mmol). The reaction mixture was degassed (N₂) for 2 min and stirred under N₂ at 95° C. for 5 hours. The reaction mixture was diluted with EtOAc and filtered through Celite©. The filtrate was washed with brine, dried over MgSO₄, filtered, and concentrated. Purification by silica gel flash chromatography (5-40% EtOAc/hexane) gave 3-fluoro-5-methoxy-2',2"-dimethyl-[1,1':3',1":3",1'''-quaterphenyl]-4,4'''-dicarbaldehyde. ¹H-NMR (400 MHz, CDCl₃) δ 10.46 (s, 1H), 10.08 (s, 1H), 7.99-7.92 (m, 2H), 7.54 (d, J=8.0 Hz, 2H), 7.37-7.16 (m, 6H), 6.79-6.66 (m, 2H), 3.96 (s, 3H), 2.00 (s, 3H), 1.97 (s, 3H).

Step c: 3-fluoro-5-methoxy-2',2"-dimethyl-[1,1':3',1":3",1'''-quaterphenyl]-4,4'''-dicarbaldehyde (129 mg, 0.29 mmol) was dissolved in a 1:1 mixture of methanol and tetrahydrofuran (12 mL). The reaction mixture was cooled to 0° C., and sodium borohydride (45 mg, 1.18 mmol) was slowly added. The reaction mixture was stirred while allowing to warm to room temperature gradually over 2 hours. The reaction was cooled to 0° C., diluted with saturated NaHCO₃ (50 mL), and extracted with CHCl₃ (3×50 mL). The combined organic fractions were dried over MgSO₄, filtered, and concentrated to afford (3-fluoro-5-methoxy-2',2"-dimethyl-[1,1':3',1":3",1'''-quaterphenyl]-4,4'''-diyl)dimethanol. The crude material was then dissolved in CH₂Cl₂ (7 mL) and cooled to 0° C., and iPr₂NEt (0.57 mL, 3.3 mmol) and methanesulfonyl chloride (0.13 mL, 1.6 mmol) were added. The reaction mixture was stirred while allowing to warm to room temperature gradually over 2 hours. The reaction mixture was cooled to 0° C., diluted with water (25 mL), and extracted with CH₂Cl₂ (3×25 mL). The combined organic fractions were dried over MgSO₄, filtered, and concentrated to afford (3-fluoro-5-methoxy-2',2"-dimethyl-[1,1':3',1":3",1'''-quaterphenyl]-4,4'''-diyl)bis(methylene) dimethanesulfonate.

Step d: (3-fluoro-5-methoxy-2',2"-dimethyl-[1,1':3',1":3",1'''-quaterphenyl]-4,4'''-diyl)bis(methylene) dimethanesulfonate (163 mg, 0.27 mmol) was dissolved in dimethyl sulfoxide (3 mL) at room temperature. Sodium azide (88 mg, 1.4 mmol) was added, and the reaction mixture was stirred at room temperature overnight. The reaction mixture was cooled to 0° C., diluted with water (25 mL), and extracted with CHCl₃ (3×25 mL). The combined organic fractions were dried over MgSO₄, filtered, and concentrated to afford 4,4'''-bis(azidomethyl)-3-fluoro-5-methoxy-2',2"-dimethyl-1,1':3',1":3",1'''-quaterphenyl.

Step e: 4,4'''-bis(azidomethyl)-3-fluoro-5-methoxy-2',2''-dimethyl-1,1':3',1'':3'',1'''-quaterphenyl (98 mg, 0.20 mmol) was dissolved in a 4:1 mixture of tetrahydrofuran and methanol (7.5 mL). Triphenylphosphine (261 mg, 0.99 mmol) was slowly added and the resultant solution was stirred at 50° C. over 2.5 hours. The reaction was cooled to room temperature, diluted with water (25 mL), and extracted with EtOAc (3×25 mL). The combined organic fractions were dried over MgSO$_4$, filtered, and concentrated. The residue was purified by preparative HPLC (H$_2$O/MeCN with 0.1% TFA) to give (3-fluoro-5-methoxy-2',2''-dimethyl-[1,1':3',1'':3'',1'''-quaterphenyl]-4,4'''-diyl)dimethanamine. $^1$H-NMR (400 MHz, CD$_3$OD) δ 7.56-7.49 (m, 2H), 7.43 (d, J=8.1 Hz, 2H), 7.36-7.28 (m, 2H), 7.25-7.12 (m, 4H), 6.89 (s, 1H), 6.82 (dd, J=1.4, 9.9 Hz, 1H), 4.23 (s, 2H), 4.18 (s, 2H), 3.97 (s, 3H), 1.97 (s, 3H), 1.94 (s, 3H). MS: (ES) m/z calculated for C$_{29}$H$_{27}$FNO [M−NH$_2$]$^+$ 424.2, found 424.2.

Example 18: (2'',3-difluoro-3'',5-dimethoxy-2'-methyl-[1,1':3',1''-terphenyl]-4-yl)methanamine raphy (5 to 20% to 40% EtOAc/hexane) to give tert-butyl ((2'',3-difluoro-3'',5-dimethoxy-2'-methyl-[1,1':3',1''-terphenyl]-4-yl)methyl)carbamate. $^1$H-NMR (400 MHz, CDCl$_3$) δ 7.33-7.17 (m, 3H), 7.15-7.10 (m, 1H), 7.03-6.96 (m, 1H), 6.87-6.82 (m, 1H), 6.74-6.63 (m, 2H), 3.93 (s, 3H), 3.86 (s, 3H), 3.70 (s, 2H), 2.04 (s, 3H), 1.45 (s, 9H).

Step b: To a solution of tert-butyl ((2'',3-difluoro-3'',5-dimethoxy-2'-methyl-[1,1':3',1''-terphenyl]-4-yl)methyl)carbamate (41 mg, 0.09 mmol) in CH$_2$Cl$_2$ (4 mL) was added trifluoroacetic acid (1 mL). The resultant mixture was stirred at room temperature for 2 hours. The mixture was concentrated, and the residue was purified by preparative HPLC (H$_2$O/MeCN with 0.1% TFA) to afford (2'',3-difluoro-3'',5-dimethoxy-2'-methyl-[1,1':3',1''-terphenyl]-4-yl)methanamine. $^1$H-NMR (400 MHz, CD$_3$OD) δ 7.35-7.30 (m, 1H), 7.28-7.10 (m, 4H), 6.90 (s, 1H), 6.85-6.77 (m, 2H), 4.23 (s, 2H), 3.97 (s, 3H), 3.91 (s, 3H), 2.03 (s, 3H). MS: (ES) m/z calculated for C$_{22}$H$_{19}$F$_2$O$_2$ [M−NH$_2$]$^+$ 353.1, found 353.2.

Example 19: (3-fluoro-5-methoxy-2'-methyl-3'-(5-methyl-2,3-dihydrobenzo[b][1,4]dioxin-6-yl)-[1,1'-biphenyl]-4-yl)methanamine

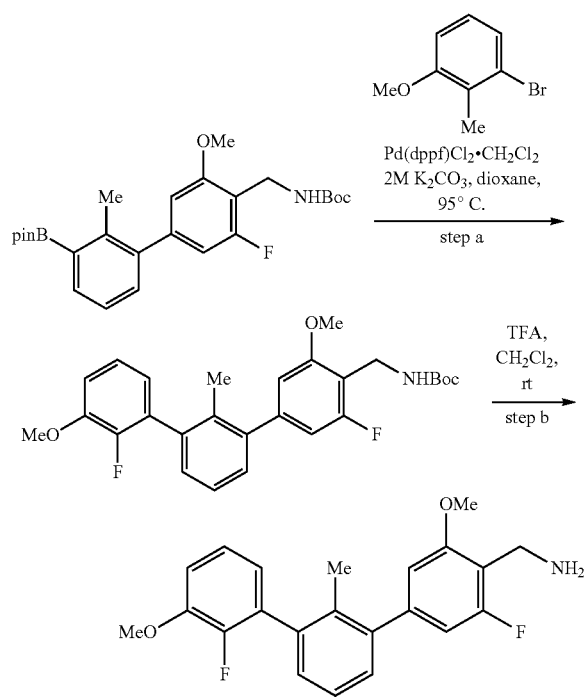

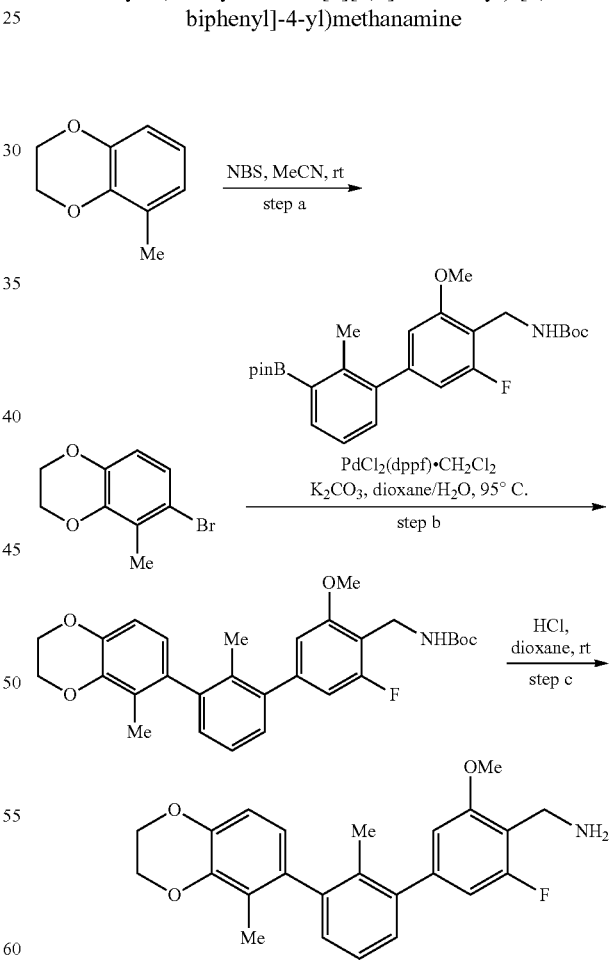

Step a: To a mixture of 1-bromo-2-fluoro-3-methoxybenzene (50 mg, 0.22 mmol), tert-butyl ((3-fluoro-5-methoxy-2'-methyl-3'-(4,4,5,5-tetramethyl-1,3,2-dioxaborolan-2-yl)-[1,1'-biphenyl]-4-yl)methyl)carbamate (70 mg, 0.15 mmol), 2 M K$_2$CO$_3$ (0.22 mL, 0.45 mmol), and dioxane (3 mL) was added [1,1'-bis(diphenylphosphino)ferrocene]dichloropalladium(II) complex with dichloromethane (18 mg, 0.02 mmol). The reaction mixture was degassed (N$_2$) for 2 min and stirred under N$_2$ at 95° C. for 5 hours. The reaction mixture was diluted with EtOAc, an filtered through Celite®. The filtrate was washed with brine and dried over MgSO$_4$. The solvent was removed under reduced pressure and the residue was purified by silica gel flash chromatog- Step a: A mixture of 5-methyl-2,3-dihydrobenzo[b][1,4]dioxine (0.100 g, 0.67 mmol), NBS (0.118 g, 0.67 mmol) in acetonitrile (2.5 mL) was stirred at room temperature for 30 min. The solvent was removed under reduced pressure and the residue was purified by silica gel flash chromatography (0-30% EtOAc/hexanes) to give 6-bromo-5-methyl-2,3-dihydrobenzo[b][1,4]dioxine. MS: (ES) m/z calculated for $C_9H_8BrO_2$ [M−H]⁻, 227.0, found 227.0.

Step b: A mixture of 6-bromo-5-methyl-2,3-dihydrobenzo[b][1,4]dioxine (0.044 g, 0.19 mmol), tert-butyl ((3-fluoro-5-methoxy-2'-methyl-3'-(4,4,5,5-tetramethyl-1,3,2-dioxaborolan-2-yl)-[1,1'-biphenyl]-4-yl)methyl)carbamate (0.060 mg, 0.13 mmol), $K_2CO_3$ (0.053 g, 0.38 mmol), [1,1'-bis(diphenylphosphino)ferrocene]dichloropalladium(II) complex with dichloromethane (0.035 g, 0.043 mmol) in p-dioxane (1.7 mL) and water (0.30 mL) was degassed ($N_2$) for 2 min and stirred under $N_2$ at 95° C. for 1.5 h. The mixture was diluted with EtOAc and filtered through Celite®/$Na_2SO_4$. The filtrate was concentrated under reduced pressure, and the residue was purified by silica gel flash chromatography (0-70% EtOAc/hexanes) to give tert-butyl ((3-fluoro-5-methoxy-2'-methyl-3'-(5-methyl-2,3-dihydrobenzo[b][1,4]dioxin-6-yl)-[1,1'-biphenyl]-4-yl)methyl)carbamate. MS: (ES) m/z calculated for $C_{29}H_{32}FNNaO_5$ [M+Na]⁺ 516.2, found 516.2.

Step c: A mixture of tert-butyl ((3-fluoro-5-methoxy-2'-methyl-3'-(5-methyl-2,3-dihydrobenzo[b][1,4]dioxin-6-yl)-[1,1'-biphenyl]-4-yl)methyl)carbamate (0.040 g, 0.080 mmol) was stirred in HCl (0.70 mL, 4 M/dioxane) for 30 min. The reaction mixture was then concentrated under reduced pressure. The obtained residue was purified by reverse phase preparative HPLC ($H_2O$/MeCN with 0.1% TFA) to give (3-fluoro-5-methoxy-2'-methyl-3'-(5-methyl-2,3-dihydrobenzo[b][1,4]dioxin-6-yl)-[1,1'-biphenyl]-4-yl)methanamine). ¹H-NMR (400 MHz, $CD_3OD$) δ 7.27 (t, J=7.6 Hz, 1H), 7.18 (dd, J=1.6, 7.2 Hz, 1H), 7.08 (dd, J=1.6, 7.6, Hz 1H), 6.88 (s, 1H), 6.81 (dd, J=1.2, 10 Hz, 1H), 6.71 (dd, J=0.8, 8.4 Hz, 1H), 6.55 (d, J=8.0 Hz, 1H), 4.32-4.29 (m, 2H), 4.26-4.23 (m, 2H), 4.22 (s, 2H), 3.96 (s, 3H), 1.91 (s, 3H), 1.89 (s, 3H). MS: (ES) m/z calculated for $C_{24}H_{22}FO_3$ [M−NH₂]⁺ 377.2, found 377.2.

Example 20: (3-fluoro-5-methoxy-2',2''-dimethyl-3''-(pyridin-2-yloxy)-[1,1':3',1''-terphenyl]-4-yl)methanamine

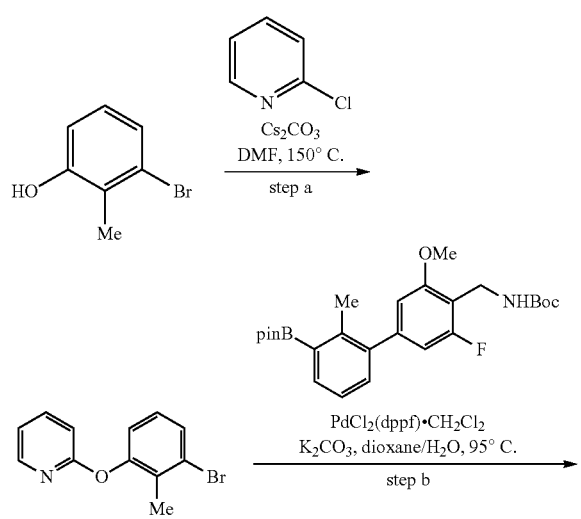

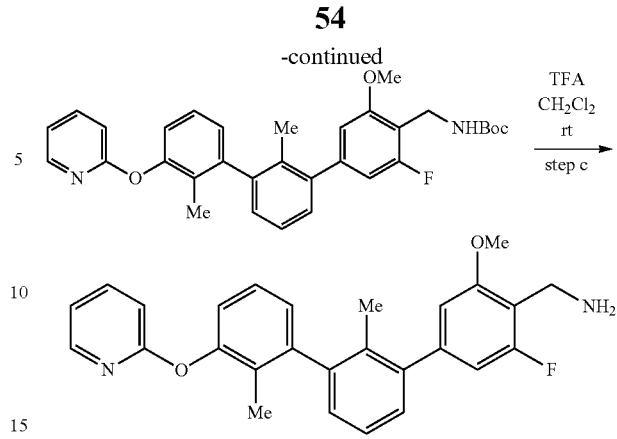

Step a: To a stirred solution of 3-bromo-2-methylphenol (1.0 g, 5.34 mmol) in anhydrous DMF (10 mL) were added 2-chloropyridine (0.78 g, 5.88 mmol) and cesium carbonate (2.6 g, 8.01 mmol) at room temperature. The reaction mixture was stirred at 150° C. for 24 h. The reaction mixture was then poured into water (25 mL) and extracted with EtOAc (2×50 mL). The combined organic layers were concentrated, and the crude residue was purified by silica gel flash chromatography (10-40% EtOAc/hexane) to give 2-(3-bromo-2-methylphenoxy)pyridine.

Step b: To a mixture of 2-(3-bromo-2-methylphenoxy)pyridine (75 mg, 0.24 mmol), tert-butyl ((3-fluoro-5-methoxy-2'-methyl-3'-(4,4,5,5-tetramethyl-1,3,2-dioxaborolan-2-yl)-[1,1'-biphenyl]-4-yl)methyl)carbamate (133 mg, 0.28 mmol), 2 M $K_2CO_3$ (0.35 mL, 0.71 mmol), and dioxane (10 mL) was added [1,1'-bis(diphenylphosphino)ferrocene]dichloropalladium(II) complex with dichloromethane (23 mg, 0.028 mmol). The reaction mixture was degassed ($N_2$) for 2 min and stirred under $N_2$ at 95° C. for 5 h. The reaction mixture was diluted with EtOAc and filtered through Celite®. The filtrate was washed with brine and dried over $MgSO_4$. The solvent was removed under reduced pressure and the residue was purified by silica gel flash chromatography (5-100% EtOAc/hexane) to give tert-butyl ((3-fluoro-5-methoxy-2',2''-dimethyl-3''-(pyridin-2-yloxy)-[1,1':3',1''-terphenyl]-4-yl)methyl)carbamate. MS: (ES) m/z calculated for $C_{32}H_{33}FN_2O_4$[M+H]⁺ 529.2, found 529.0.

Step c: To a stirred solution of tert-butyl ((3-fluoro-5-methoxy-2',2''-dimethyl-3''-(pyridin-2-yloxy)-[1,1':3',1''-terphenyl]-4-yl)methyl)carbamate (50 mg, 0.09 mmol) in anhydrous dichloromethane (2.5 mL) at room temperature was added trifluoroacetic acid (107 mg, 0.94 mmol) dropwise over 5 min. The reaction mixture was stirred at room temperature for 2 h. After completion of the reaction, the solvent was removed in vacuo, and the crude residue was purified by reverse phase preparative HPLC ($H_2O$/MeCN with 0.1% TFA) to give (3-fluoro-5-methoxy-2',2''-dimethyl-3''-(pyridin-2-yloxy)-[1,1':3',1''-terphenyl]-4-yl)methanamine. ¹H-NMR (400 MHz, $CD_3OD$) δ 8.12 (dd, J=2.2, 4.9 Hz, 1H), 7.83 (ddd, J=1.9, 2.2, 6.6 Hz, 1H), 7.45-7.30 (m, 2H), 7.27-7.16 (m, 2H), 7.14-7.02 (m, 3H), 6.95-6.79 (m, 3H), 4.22 (s, 2H), 3.96 (s, 3H), 1.96 (s, 3H), 1.89 (s, 3H). MS: (ES) m/z calculated for $C_{27}H_{23}FNO_2$ [M−NH₂]⁺ 412.2, found 412.0.

Example 21: (3'-(3-(aminomethyl)-2,3-dihydrobenzo[b][1,4]dioxin-6-yl)-3-fluoro-5-methoxy-2'-methyl-[1,1'-biphenyl]-4-yl)methanamine

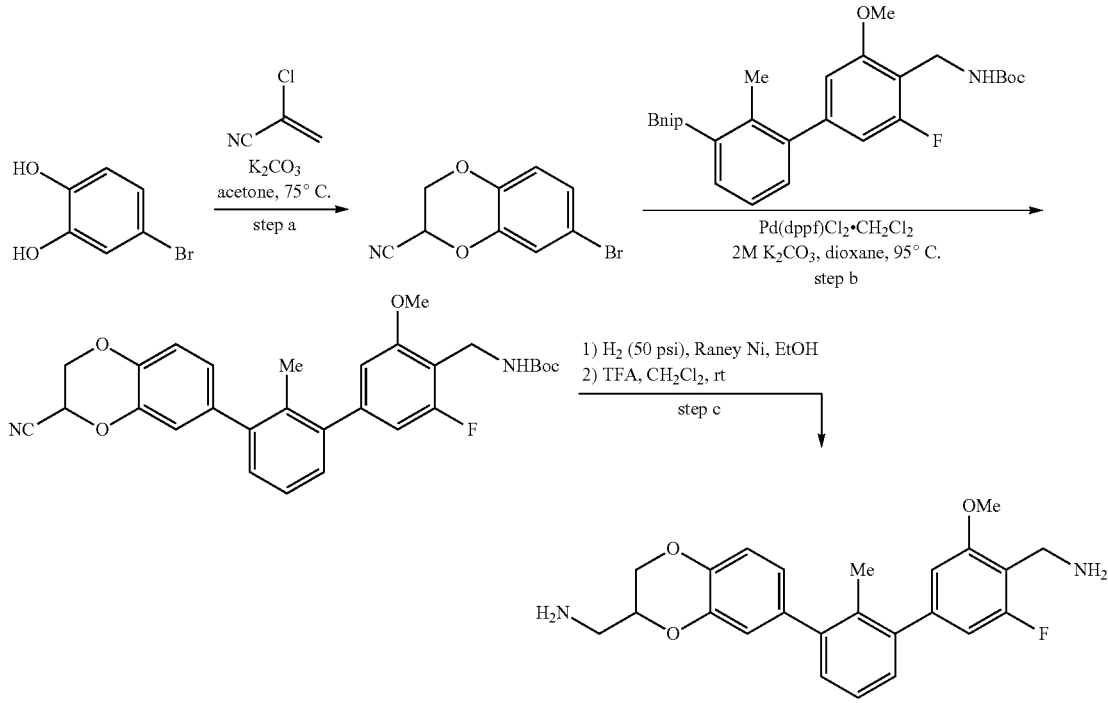

Step a: To a stirred solution of 4-bromobenzene-1,2-diol (5.0 g, 26.4 mmol) in anhydrous acetone (100 mL) were added 2-chloroacrylonitrile (3.0 mL, 26.4 mmol), and potassium carbonate (7.3 g, 52.9 mmol) at room temperature. The mixture was heated at 75° C. for 24 hours. After completion of the reaction, the solvent was removed. The residue was poured into water (150 mL) and extracted with EtOAc (150 mL). The organic layer was concentrated, and the crude product was purified by silica gel flash chromatography (10-40% EtOAc/hexane) to give 7-bromo-2,3-dihydrobenzo[b][1,4]dioxine-2-carbonitrile.

Step b: To a mixture of 7-bromo-2,3-dihydrobenzo[b][1,4]dioxine-2-carbonitrile (125 mg, 0.52 mmol), tert-butyl ((3-fluoro-5-methoxy-2'-methyl-3'-(4,4,5,5-tetramethyl-1,3,2-dioxaborolan-2-yl)-[1,1'-biphenyl]-4-yl)methyl)carbamate (245 mg, 0.52 mmol), 2 M $K_2CO_3$ (0.65 mL, 1.30 mmol), and dioxane (4 mL) was added [1,1'-bis(diphenylphosphino)ferrocene]-dichloropalladium(II) complex with dichloromethane (42 mg, 0.052 mmol). The reaction mixture was degassed ($N_2$) for 2 min and stirred under $N_2$ at 95° C. for 4 h. The reaction mixture was diluted with EtOAc and filtered through Celite®. The filtrate was washed with brine and dried over $MgSO_4$. The solvent was removed under reduced pressure, and the residue was purified by silica gel flash chromatography (5-40% EtOAc/hexane) to give tert-butyl ((3'-(3-cyano-2,3-dihydrobenzo[b][1,4]dioxin-6-yl)-3-fluoro-5-methoxy-2'-methyl-[1,1'-biphenyl]-4-yl)methyl)carbamate. MS: (ES) m/z calculated for $C_{29}H_{29}FN_2O_5[M+H]^+$ 505.21, found 505.2.

Step c: To a solution of tert-butyl ((3'-(3-cyano-2,3-dihydrobenzo[b][1,4]dioxin-6-yl)-3-fluoro-5-methoxy-2'-methyl-[1,1'-biphenyl]-4-yl)methyl)carbamate (100 mg, 0.19 mmol) in MeOH (10 mL) was added Raney Ni (approx. 200 mg). The reaction mixture was hydrogenated under 50 psi for 5 h. After completion of the reaction, the mixture was filtered through Celite®, rinsed with 1:1 EtOAc/MeOH (50 mL), and concentrated to dryness. The residue was dissolved in anhydrous dichloromethane (4 mL) at room temperature, and trifluoroacetic acid (141 mg, 1.23 mmol) was added dropwise over 5 min. The reaction mixture was stirred at room temperature for 2 h. After completion of the reaction, the solvent was removed in vacuo, and the crude residue was purified by reverse phase preparative HPLC ($H_2O$/MeCN with 0.1% TFA) to give (3'-(3-(aminomethyl)-2,3-dihydrobenzo[b][1,4]dioxin-6-yl)-3-fluoro-5-methoxy-2'-methyl-[1,1'-biphenyl]-4-yl)methanamine. $^1$H-NMR (400 MHz, $CD_3OD$) δ 7.33-7.14 (m, 3H), 7.07-6.92 (m, 2H), 6.91-6.78 (m, 3H), 4.55-4.45 (m, 1H), 4.39 (dd, J=2.3, 11.9 Hz, 1H), 4.22 (s, 2H), 4.07 (dd, J=6.9, 11.9 Hz, 1H), 3.96 (s, 3H), 3.37 (dd, J=3.2, 13.5 Hz, 1H), 3.32 (dd, J=3.2, 13.5 Hz, 1H), 2.12 (s, 3H). MS: (ES) m/z calculated for $C_{24}H_{23}FNO_3$ [M–$NH_2$]$^+$ 392.2, found 392.1.

Example 22: 7-(4'-(aminomethyl)-3'-fluoro-5'-methoxy-2-methyl-[1,1'-biphenyl]-3-yl)-3,4-dihydroquinolin-2(1H)-one

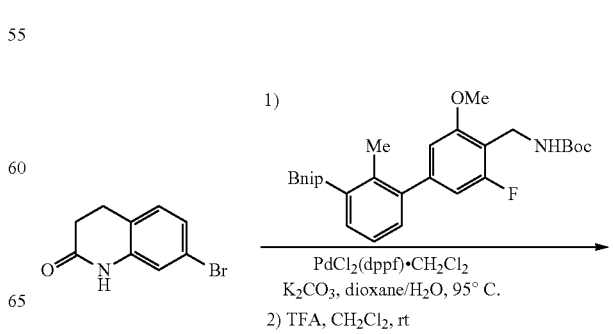

-continued

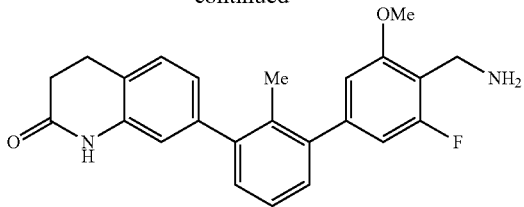

The compound was prepared from 7-bromo-3,4-dihydroquinolin-2(1H)-one and tert-butyl ((3-fluoro-5-methoxy-2'-methyl-3'-(4,4,5,5-tetramethyl-1,3,2-dioxaborolan-2-yl)-[1,1'-biphenyl]-4-yl)methyl)carbamate using the procedure from Example 21 (step b and step c). Purification by reverse phase preparative HPLC (H₂O/MeCN with 0.1% TFA) to give 7-(4'-(aminomethyl)-3'-fluoro-5'-methoxy-2-methyl-[1,1'-biphenyl]-3-yl)-3,4-dihydroquinolin-2(1H)-one as a white solid. $^1$H-NMR (400 MHz, CD₃OD) δ 7.93-7.87 (m, 1H), 7.52-7.45 (m, 1H), 7.43-7.19 (m, 4H), 6.92 (d, J=1.4 Hz, 1H), 6.85 (d, J=9.9 Hz, 1H), 4.22 (s, 2H), 3.97 (s, 3H), 3.55 (t, J=6.7 Hz, 2H), 3.05 (t, J=6.7 Hz, 2H), 2.10 (s, 3H). MS: (ES) m/z calculated for $C_{24}H_{24}FN_2O_2[M+H]^+$ 391.2, found 391.2.

Example 23: Methyl 6-(4'-(aminomethyl)-3'-fluoro-5'-methoxy-2-methyl-[1,1'-biphenyl]-3-yl)-2H-chromene-3-carboxylate

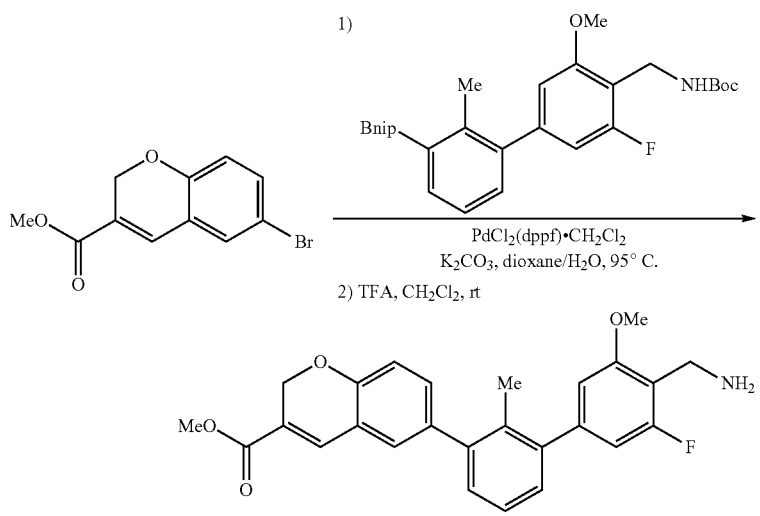

The compound was prepared from methyl 6-bromo-2H-chromene-3-carboxylate and tert-butyl ((3-fluoro-5-methoxy-2'-methyl-3'-(4,4,5,5-tetramethyl-1,3,2-dioxaborolan-2-yl)-[1,1'-biphenyl]-4-yl)methyl)carbamate using the procedure from Example 21 (step b and step c). The product was purified by reverse phase HPLC (C18 column, acetonitrile-H₂O with 0.1% TFA as eluent) to give the desired product methyl 6-(4'-(aminomethyl)-3'-fluoro-5'-methoxy-2-methyl-[1,1'-biphenyl]-3-yl)-2H-chromene-3-carboxylate as a white solid. $^1$H-NMR (400 MHz, CD₃OD) δ 7.55 (s, 1H), 7.34-7.15 (m, 5H), 6.94-6.80 (m, 3H), 5.00 (s, 2H), 4.22 (s, 2H), 3.97 (s, 3H), 3.81 (s, 3H), 2.10 (s, 3H). MS: (ES) m/z calculated for $C_{26}H_{25}FNO_4$ [M+H]$^+$ 434.2, found 434.1.

Example 24: 2,2'-(((3,3'''-difluoro-5,5'''-dimethoxy-2',2''-dimethyl-[1,1':3',1'':3'',1'''-quaterphenyl]-4,4'''-diyl)bis(methylene))bis(azanediyl))bis(ethane-1-sulfonic Acid)

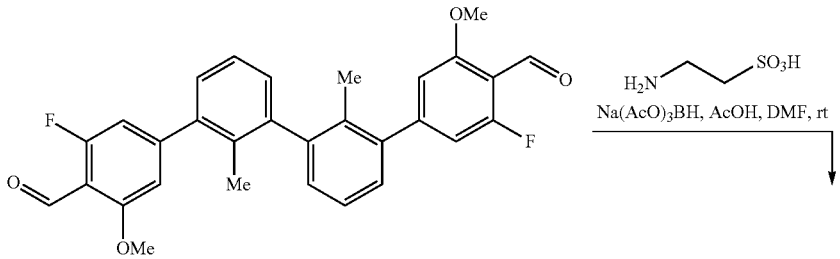

-continued

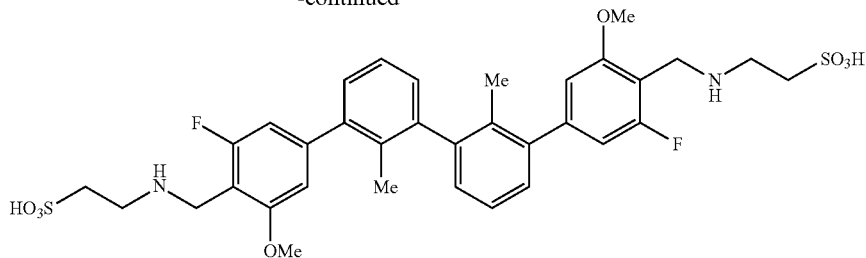

To a stirred solution of 3,3'''-difluoro-5,5'''-dimethoxy-2',2''-dimethyl-[1,1':3',1'':3'',1'''-quaterphenyl]-4,4'''-dicarbaldehyde (65 mg, 0.133 mmol), and 2-aminoethane-1-sulfonic acid (10 mg, 0.16 mmol) in DMF (2 mL) was added Na(AcO)$_3$BH (52 mg, 0.24 mmol) and AcOH (5 drops). The reaction mixture was stirred at room temperature for 16 hours. The solvent was removed under reduced pressure, and the residue was purified by reverse phase preparative HPLC (H$_2$O/MeCN with 0.1% TFA) to give 2,2'-(((3,3'''-difluoro-5,5'''-dimethoxy-2',2''-dimethyl-[1,1':3',1'':3'',1'''-quaterphenyl]-4,4'''-diyl)bis(methylene))bis(azanediyl))-bis(ethane-1-sulfonic acid). $^1$H-NMR (400 MHz, CD$_3$OD) δ 7.33 (t, J=7.6 Hz, 2H), 7.25 (dd, J=1.5, 7.6 Hz, 2H), 7.21-7.14 (m, 2H), 6.96-6.81 (m, 4H), 4.39 (s, 4H), 3.98 (s, 6H) 3.49 (d, J=6.3 Hz, 4H) 3.15 (t, J=6.3 Hz, 4H) 1.97 (s, 6H). MS: (ES) m/z calculated for C$_{34}$H$_{39}$F$_2$N$_2$O$_8$S$_2$ [M+H]$^+$ 705.2, found 705.2.

Example 25: 2-(((3-fluoro-5-methoxy-2',2''-dimethyl-3''-(1,2,3,4-tetrahydroisoquinolin-6-yl)-[1,1':3',1''-terphenyl]-4-yl)methyl)amino)ethan-1-ol

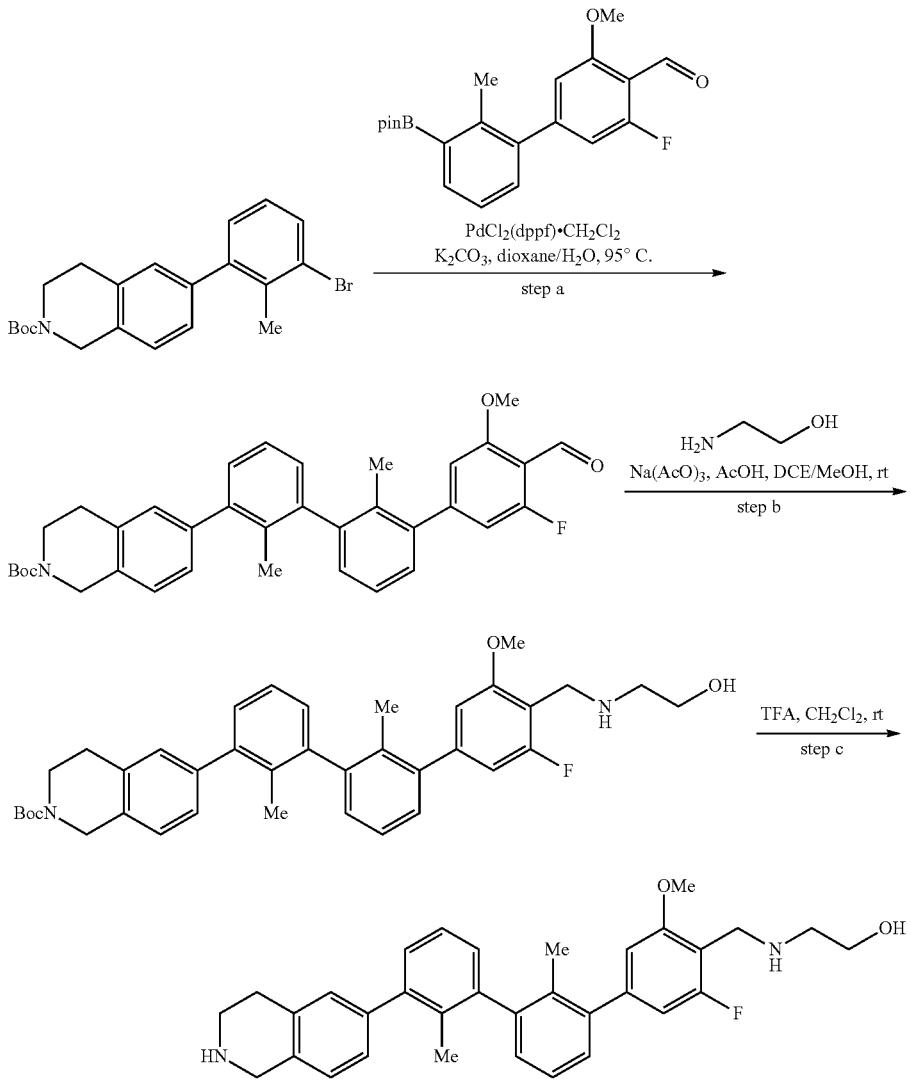

Step a: To a mixture of tert-butyl 6-(3-bromo-2-methylphenyl)-3,4-dihydroisoquinoline-2(1H)-carboxylate (100 mg, 0.249 mmol), and 3-fluoro-5-methoxy-2'-methyl-3'-(4,4,5,5-tetramethyl-1,3,2-dioxaborolan-2-yl)-[1,1'-biphenyl]-4-carbaldehyde (101 mg, 0.27 mmol), 2M $K_2CO_3$ (0.35 mL, 0.024 mmol), and dioxane (4 mL) was added [1,1'-bis(diphenylphosphino)ferrocene]dichloropalladium(II) complex with dichloromethane (1 mg, 0.148 mmol). The reaction mixture was degassed ($N_2$) for 2 min and stirred under $N_2$ at 95° C. for 5 hours. The reaction mixture was diluted with EtOAc and filtered through Celite®. The filtrate was washed with brine and dried over $MgSO_4$. The solvent was removed under reduced pressure, and the residue was purified by silica gel flash chromatography (5-100% EtOAc/hexane) to give tert-butyl 6-(3"-fluoro-4"-formyl-5"-methoxy-2,2'-dimethyl-[1,1':3',1"-terphenyl]-3-yl)-3,4-dihydroisoquinoline-2(1H)-carboxylate (100 mg). MS: (ES) m/z calculated for $C_{36}H_{36}FNO_4$ [M+H]$^+$ 566.3, found 566.2.

Step b: To a stirred solution of tert-butyl 6-(3"-fluoro-4"-formyl-5"-methoxy-2,2'-dimethyl-[1,1':3',1"-terphenyl]-3-yl)-3,4-dihydroisoquinoline-2(1H)-carboxylate (70 mg, 0.082 mmol) and 2-aminoethanol (30 mg, 0.16 mmol), in MeOH/DCE (2 mL) was added $Na(AcO)_3BH$ (65 mg, 0.24 mmol) and AcOH (5 drops). The reaction mixture was stirred at room temperature for 2 h. The solvent was removed under reduced pressure to give crude tert-butyl 6-(3"-fluoro-4"-(((2-hydroxyethyl)amino)methyl)-5"-methoxy-2,2'-dimethyl-[1,1':3',1"-terphenyl]-3-yl)-3,4-dihydroisoquinoline-2(1H)-carboxylate, which was used without further purification.

Step c: To a stirred solution of tert-butyl 6-(3"-fluoro-4"-(((2-hydroxyethyl)amino)methyl)-5"-methoxy-2,2'-dimethyl-[1,1':3',1"-terphenyl]-3-yl)-3,4-dihydroisoquinoline-2(1H)-carboxylate (70 mg, 0.114 mmol) in anhydrous dichloromethane (2.5 mL) at room temperature was added trifluoroacetic acid (130 mg, 1.14 mmol) dropwise over 5 min. The reaction mixture was stirred at room temperature for 2 h. After completion of the reaction, the solvent was removed in vacuo. Purification by reverse phase preparative HPLC ($H_2O$/MeCN with 0.1% TFA) gave 2-(((3-fluoro-5-methoxy-2',2"-dimethyl-3"-(1,2,3,4-tetrahydroisoquinolin-6-yl)-[1,1':3',1"-terphenyl]-4-yl)methyl)amino)ethan-1-ol.
$^1$H-NMR (400 MHz, $CD_3OD$) δ 7.38-7.09 (m, 9H), 6.94-6.82 (m, 2H), 4.41 (s, 2H), 4.36 (s, 2H), 3.98 (s, 3H), 3.84 (dd, J=1.4, 6.1 Hz, 2H), 3.54 (t, J=6.4 Hz, 2H), 3.18 (m, 4H), 1.97 (s, 3H), 1.93 (s, 3H). MS: (ES) m/z calculated for $C_{33}H_{36}FN_2O_2$ [M+H]$^+$ 511.3, found 511.2.

Characterization Conditions

Reverse phase HPLC conditions used for determination of retention times in Table 1:
Column: ZORBAX (SB-C18 2.1×50 mm, 5 μm)
Mobile phase A: 95% $H_2O$, 5% MeCN (with 0.1% Formic Acid)
Mobile phase B: 5% $H_2O$, 95% MeCN (with 0.1% Formic Acid)
Flow rate: 1.0 mL/min
Gradient: 20 to 100% B in 3.5 min (for Method A) or 0 to 100% phase B in 4.5 min (for Method B).

Biological Example: Enzyme-Linked Immunosorbent Assay—ELISA

96 Well plates were coated with 1 μg/mL of human PD-L1 (obtained from R&D) in PBS overnight at 4'° C. The wells were then blocked with 2% BSA in PBS (W/V) with 0.05% TWEEN-20 for 1 hour at 37'° C. The plates were washed 3 times with PBS/0.05% TWEEN-20 and the compounds were serial diluted (1:5) in dilution medium and added to the ELISA plates. Human PD-1 and biotin 0.3 μg/mL (ACRO Biosystems) were added and incubated for 1 hour at 37° C. then washed 3 times with PBS/0.05% TWEEN-20. A second block was performed with 2% BSA in PBS (WNV)/0.05% TWEEN-20 for 10 min at 37° C. and the plates were washed 3 times with PBS/0.05% TWEEN-20. Streptavidin-HIRP was added for 1 hour at 37° C. then the plates were washed 3 times with PBS/0.05% TWEEN-20. TMB substrate was added and reacted for 20 min at 37° C. A stop solution (2 N aqueous $H_2SO_4$) was added. The absorbance was read at 450 nm using a micro-plate spectrophotometer. The results are shown in Table 1: $IC_{50}$ values are provided as follows: from 1000 to 10,000 nM (+); Less than 1000 nM (++).

TABLE 1

| Compd ID | Structure | ELISA $IC_{50}$ (nM) | m/z ES | HPLC RT (min) | HPLC Method |
|---|---|---|---|---|---|
| 1.001 | (structure) | + | 500.3 [M + H]$^+$ | 2.9 | A |
| 1.002 | (structure) | ++ | 482.2 [M + H]$^+$ | 2.6 | A |

TABLE 1-continued

| Compd ID | Structure | ELISA IC$_{50}$ (nM) | m/z ES | HPLC RT (min) | HPLC Method |
| --- | --- | --- | --- | --- | --- |
| 1.003 | 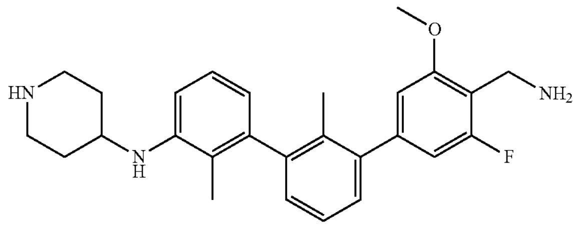 [SMILES: COc1cc(-c2cccc(-c3cccc(NC4CCNCC4)c3C)c2C)cc(F)c1CN] | ++ | 434.2 [M + H]$^+$ | 2.1 | B |
| 1.004 | 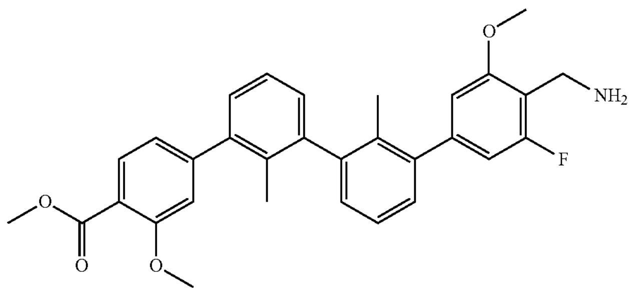 | ++ | 483.2 [M + H]$^+$ | 3.3 | A |
| 1.005 | 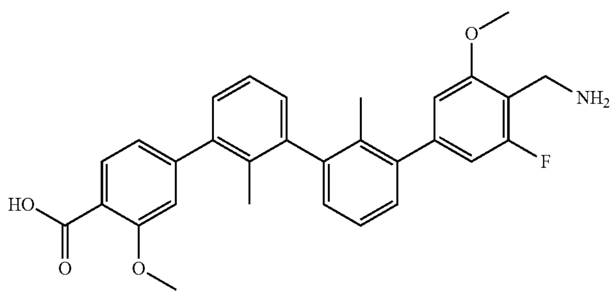 [SMILES: COc1cc(-c2cccc(-c3cccc(-c4cc(F)c(CN)c(OC)c4)c3C)c2C)ccc1C(=O)O] | + | 486.4 [M + H]$^+$ | 2.5 | A |
| 1.006 | 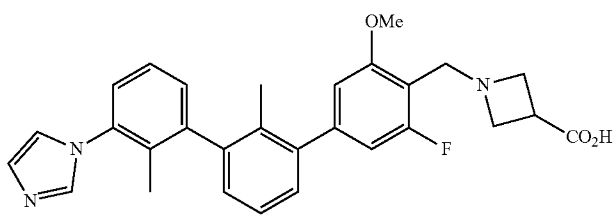 [SMILES: COc1cc(-c2cccc(-c3cccc(-n4ccnc4)c3C)c2C)cc(F)c1CN1CC(C(=O)O)C1] | + | 486.2 [M + H]$^+$ | 2.1 | B |
| 1.007 | 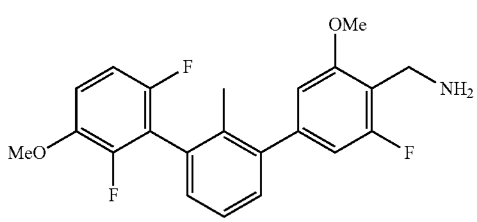 [SMILES: COc1ccc(F)c(-c2cccc(-c3cc(F)c(CN)c(OC)c3)c2C)c1F] | ++ | 371.1 [M − NH$_2$]$^+$ | 2.5 | A |
| 1.008 | 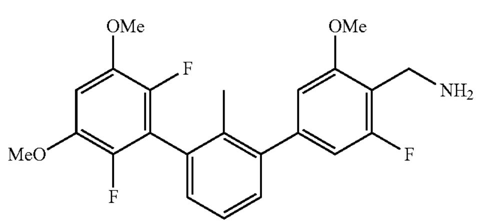 [SMILES: COc1cc(OC)c(F)c(-c2cccc(-c3cc(F)c(CN)c(OC)c3)c2C)c1F] | ++ | 401.2 [M − NH$_2$]$^+$ | 2.4 | A |

TABLE 1-continued

| Compd ID | Structure | ELISA IC$_{50}$ (nM) | m/z ES | HPLC RT (min) | HPLC Method |
|---|---|---|---|---|---|
| 1.009 | 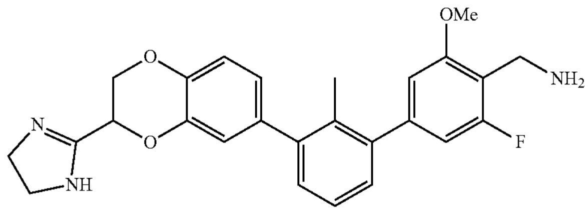 [SMILES: COc1cc(-c2cccc(-c3ccc4c(c3)OC(C3=NCCN3)CO4)c2C)cc(F)c1CN] | + | 448.1 [M + H]$^+$ | 2.1 | B |
| 1.010 | 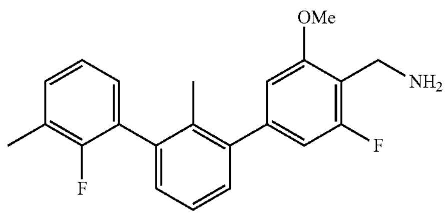 [SMILES: COc1cc(-c2cccc(-c3cccc(C)c3F)c2C)cc(F)c1CN] | ++ | 337.2 [M − NH$_2$]$^+$ | 2.9 | A |
| 1.011 | 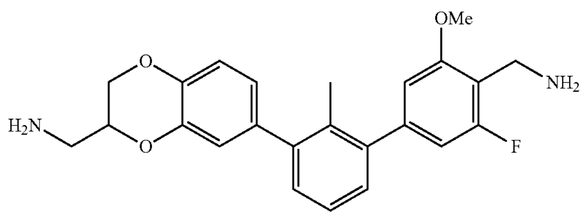 [SMILES: COc1cc(-c2cccc(-c3ccc4c(c3)OC(CN)CO4)c2C)cc(F)c1CN] | ++ | 392.1 [M − NH$_2$]$^+$ | 2.0 | B |
| 1.012 | 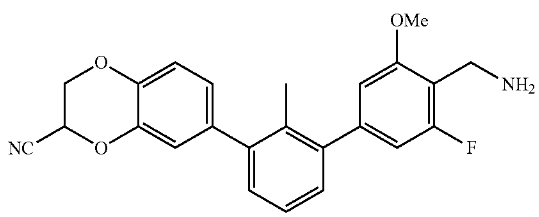 [SMILES: COc1cc(-c2cccc(-c3ccc4c(c3)OC(C#N)CO4)c2C)cc(F)c1CN] | + | 338.0 [M − NH$_2$]$^+$ | 2.1 | B |
| 1.013 | 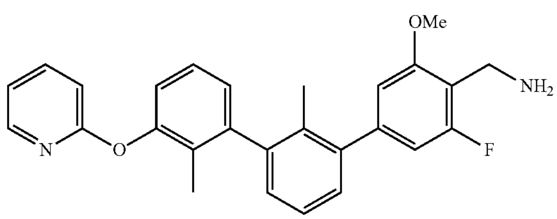 | + | 415.0 [M + H]$^+$ | 2.8 | B |
| 1.014 | 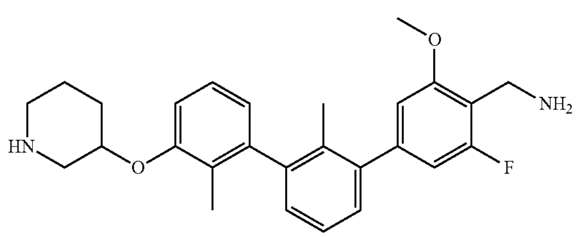 [SMILES: COc1cc(-c2cccc(-c3cccc(OC4CCCNC4)c3C)c2C)cc(F)c1CN] | + | 435.1 [M + H]$^+$ | 2.1 | B |
| 1.015 | 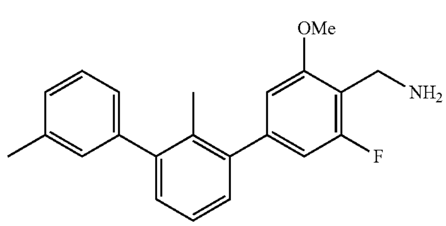 [SMILES: COc1cc(-c2cccc(-c3cccc(C)c3)c2C)cc(F)c1CN] | ++ | 319.1 [M − NH$_2$]$^+$ | 2.5 | A |

TABLE 1-continued

| Compd ID | Structure | ELISA IC$_{50}$ (nM) | m/z ES | HPLC RT (min) | HPLC Method |
|---|---|---|---|---|---|
| 1.016 | 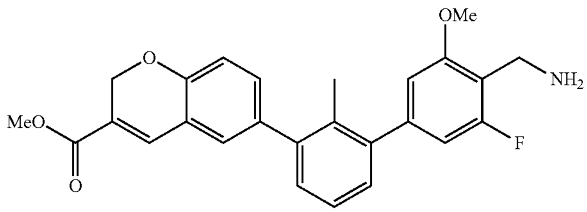 [SMILES: COC(=O)C1=Cc2cc(-c3cccc(-c4cc(F)c(CN)c(OC)c4)c3C)ccc2OC1] | ++ | 434.1 [M + H]$^+$ | 2.3 | B |
| 1.017 | 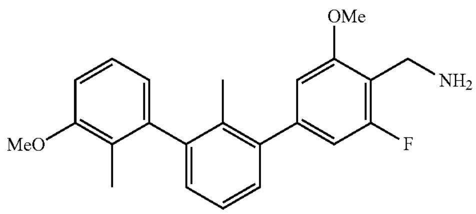 [SMILES: COc1cccc(-c2cccc(-c3cc(F)c(CN)c(OC)c3)c2C)c1C] | ++ | 349.1 [M − NH$_2$]$^+$ | 2.6 | A |
| 1.018 | 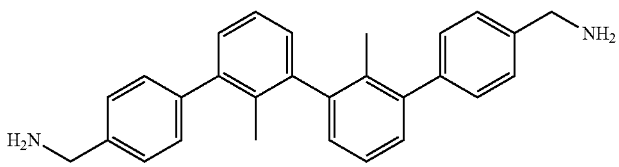 [SMILES: Cc1c(-c2ccc(CN)cc2)cccc1-c1cccc(-c2ccc(CN)cc2)c1C] | ++ | 376.2 [M − NH$_2$]$^+$ | 2.2 | B |
| 1.019 | 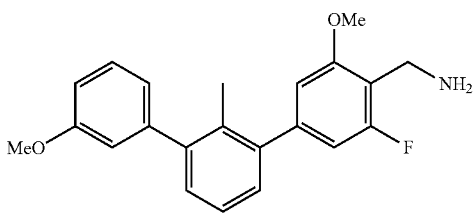 [SMILES: COc1cccc(-c2cccc(-c3cc(F)c(CN)c(OC)c3)c2C)c1] | ++ | 335.2 [M − NH$_2$]$^+$ | 3.0 | A |
| 1.020 | 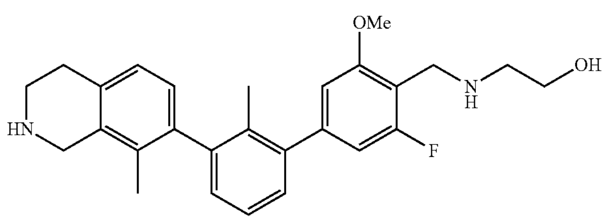 [SMILES: COc1cc(-c2cccc(-c3ccc4c(c3C)CNCC4)c2C)cc(F)c1CNCCO] | + | 435.1 [M + H]$^+$ | 2.1 | B |
| 1.021 | 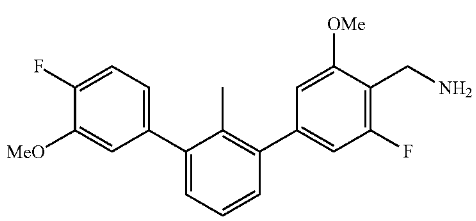 [SMILES: COc1cc(-c2cccc(-c3cc(F)c(CN)c(OC)c3)c2C)ccc1F] | + | 353.2 [M − NH$_2$]$^+$ | 2.4 | A |
| 1.022 | 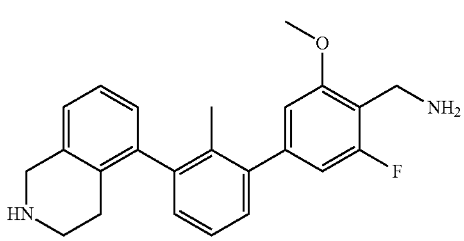 | + | 377.1 [M + H]$^+$ | 1.9 | B |

TABLE 1-continued

| Compd ID | Structure | ELISA IC$_{50}$ (nM) | m/z ES | HPLC RT (min) | HPLC Method |
| --- | --- | --- | --- | --- | --- |
| 1.023 | 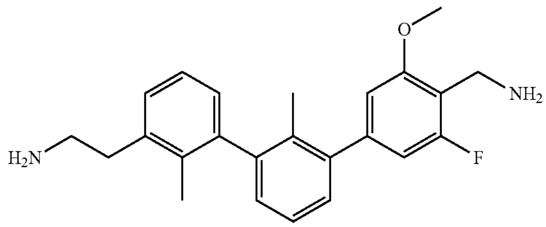 [SMILES: COc1cc(-c2cccc(-c3cccc(CCN)c3C)c2C)cc(F)c1CN] | + | 362.1 [M − NH$_2$]$^+$ | 2.1 | B |
| 1.024 | 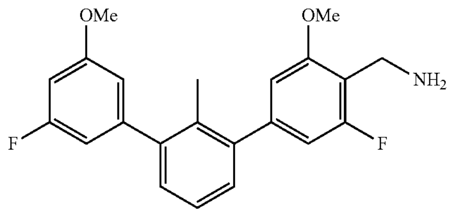 [SMILES: COc1cc(F)cc(-c2cccc(-c3cc(F)c(CN)c(OC)c3)c2C)c1] | ++ | 353.2 [M − NH$_2$]$^+$ | 2.5 | A |
| 1.025 | 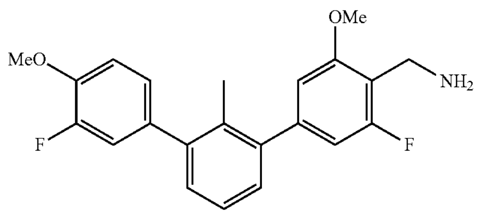 [SMILES: COc1ccc(-c2cccc(-c3cc(F)c(CN)c(OC)c3)c2C)cc1F] | + | 353.2 [M − NH$_2$]$^+$ | 2.2 | A |
| 1.026 | 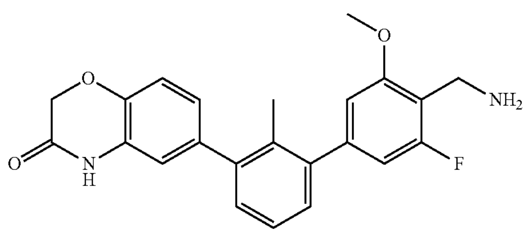 [SMILES: COc1cc(-c2cccc(-c3ccc4c(c3)NC(=O)CO4)c2C)cc(F)c1CN] | ++ | 376.0 [M − NH$_2$]$^+$ | 2.4 | B |
| 1.027 | 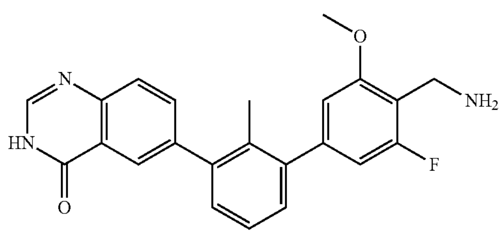 [SMILES: COc1cc(-c2cccc(-c3ccc4nc[nH]c(=O)c4c3)c2C)cc(F)c1CN] | ++ | 373.1 [M − NH$_2$]$^+$ | 1.6 | A |
| 1.028 | 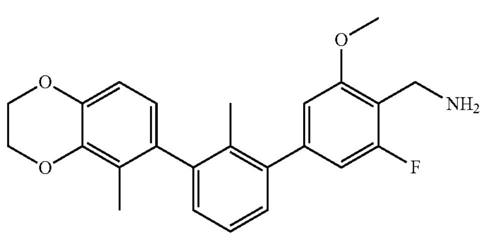 [SMILES: COc1cc(-c2cccc(-c3ccc4c(c3C)OCCO4)c2C)cc(F)c1CN] | ++ | 377.2 [M − NH$_2$]$^+$ | 3.2 | B |
| 1.029 | 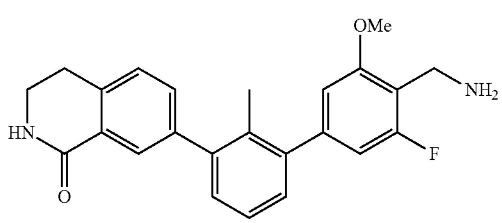 [SMILES: COc1cc(-c2cccc(-c3ccc4c(c3)C(=O)NCC4)c2C)cc(F)c1CN] | + | 391.2 [M + H]$^+$ | 2.3 | B |

TABLE 1-continued

| Compd ID | Structure | ELISA IC$_{50}$ (nM) | m/z ES | HPLC RT (min) | HPLC Method |
|---|---|---|---|---|---|
| 1.030 | 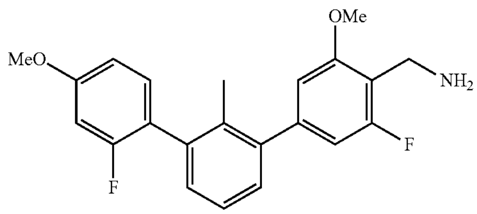 [SMILES: COc1ccc(-c2cccc(-c3cc(F)c(CN)c(OC)c3)c2C)c(F)c1] | + | 353.1 [M − NH$_2$]$^+$ | 2.9 | A |
| 1.031 | 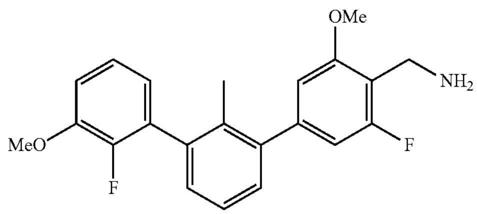 [SMILES: COc1cccc(-c2cccc(-c3cc(F)c(CN)c(OC)c3)c2C)c1F] | ++ | 353.2 [M − NH$_2$]$^+$ | 1.9 | A |
| 1.032 | 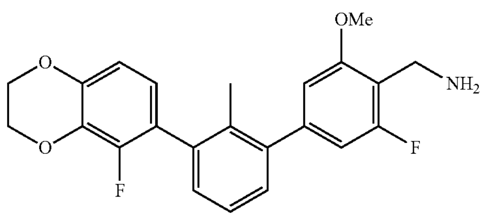 [SMILES: COc1cc(-c2cccc(-c3ccc4c(c3F)OCCO4)c2C)cc(F)c1CN] | ++ | 381.2 [M − NH$_2$]$^+$ | 2.4 | A |
| 1.033 | 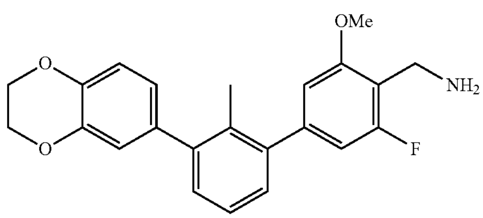 [SMILES: COc1cc(-c2cccc(-c3ccc4c(c3)OCCO4)c2C)cc(F)c1CN] | ++ | 363.2 [M − NH$_2$]$^+$ | 2.3 | A |
| 1.034 | 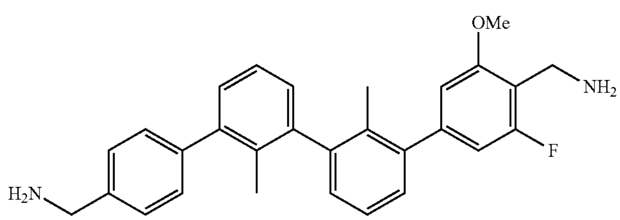 [SMILES: COc1cc(-c2cccc(-c3cccc(-c4ccc(CN)cc4)c3C)c2C)cc(F)c1CN] | ++ | 424.2 [M − NH$_2$]$^+$ | 1.5 | A |
| 1.035 | 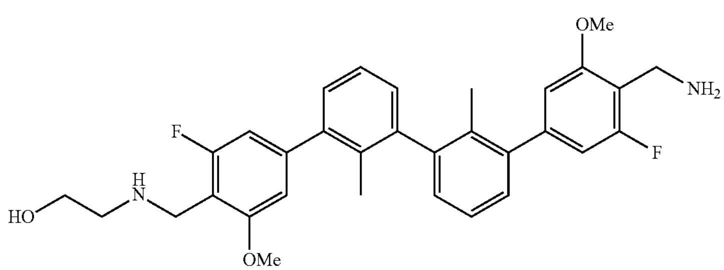 [SMILES: COc1cc(-c2cccc(-c3cccc(-c4cc(F)c(CNCCO)c(OC)c4)c3C)c2C)cc(F)c1CN] | ++ | 533.3 [M + H]$^+$ | 1.7 | A |
| 1.036 | 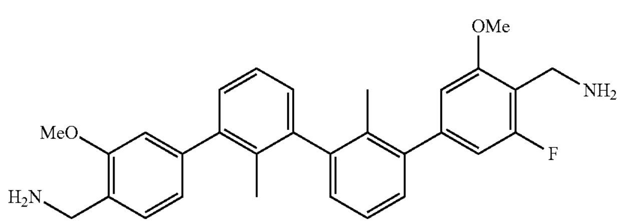 [SMILES: COc1cc(-c2cccc(-c3cccc(-c4cc(F)c(CN)c(OC)c4)c3C)c2C)ccc1CN] | ++ | 471.3 [M + H]$^+$ | 1.6 | A |

TABLE 1-continued

| Compd ID | Structure | ELISA IC$_{50}$ (nM) | m/z ES | HPLC RT (min) | HPLC Method |
|---|---|---|---|---|---|
| 1.037 | 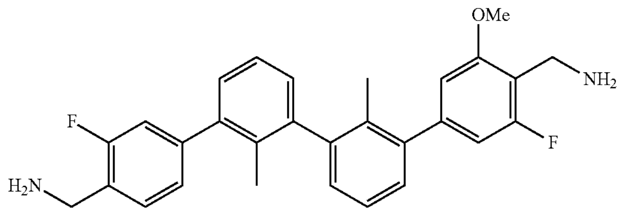 [SMILES: COc1cc(-c2cccc(-c3cccc(-c4ccc(CN)c(F)c4)c3C)c2C)cc(F)c1CN] | ++ | 459.2 [M + H]$^+$ | 1.6 | A |
| 1.038 | 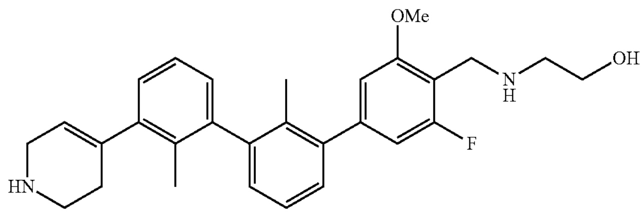 | + | 421.2 [M + H]$^+$ | 1.9 | B |
| 1.039 | 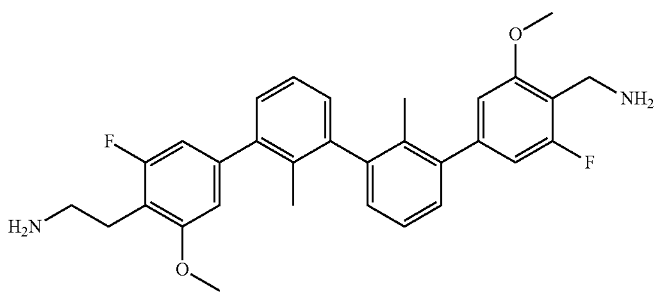 [SMILES: COc1cc(-c2cccc(-c3cccc(-c4cc(F)c(CCN)c(OC)c4)c3C)c2C)cc(F)c1CN] | ++ | 503.2 [M + H]$^+$ | 2.4 | B |
| 1.040 | 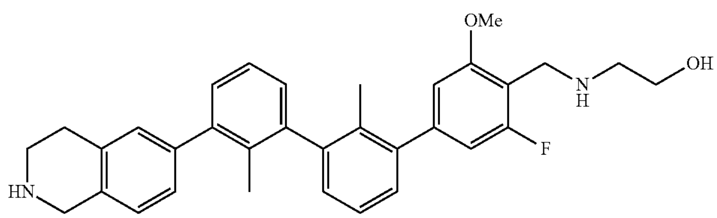 [SMILES: COc1cc(-c2cccc(-c3cccc(-c4ccc5c(c4)CCNC5)c3C)c2C)cc(F)c1CNCCO] | ++ | 511.2 [M + H]$^+$ | 2.2 | B |
| 1.041 | 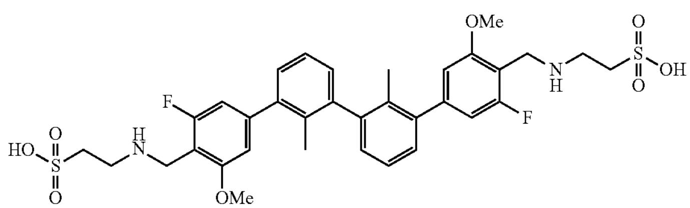 [SMILES: COc1cc(-c2cccc(-c3cccc(-c4cc(F)c(CNCCS(=O)(=O)O)c(OC)c4)c3C)c2C)cc(F)c1CNCCS(=O)(=O)O] | ++ | 705.2 [M + H]$^+$ | 2.5 | B |
| 1.042 | 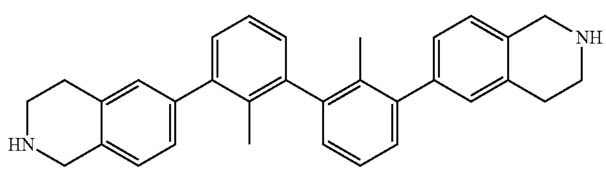 [SMILES: Cc1c(-c2ccc3c(c2)CCNC3)cccc1-c1cccc(-c2ccc3c(c2)CCNC3)c1C] | ++ | 445.2 [M + H]$^+$ | 1.5 | A |
| 1.043 | 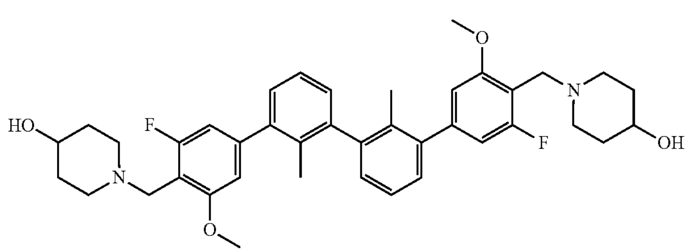 [SMILES: COc1cc(-c2cccc(-c3cccc(-c4cc(F)c(CN5CCC(O)CC5)c(OC)c4)c3C)c2C)cc(F)c1CN1CCC(O)CC1] | ++ | 657.2 [M + H]$^+$ | 1.5 | A |

TABLE 1-continued

| Compd ID | Structure | ELISA IC$_{50}$ (nM) | m/z ES | HPLC RT (min) | HPLC Method |
|---|---|---|---|---|---|
| 1.044 | 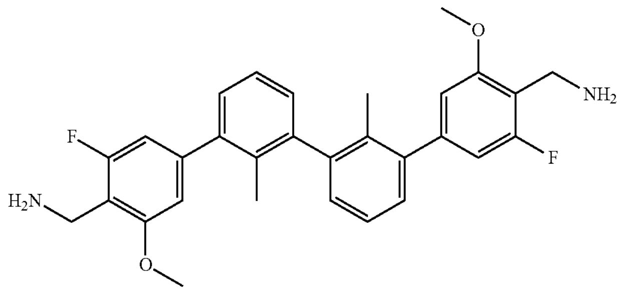 [SMILES: COc1cc(-c2cccc(-c3cccc(-c4cc(F)c(CN)c(OC)c4)c3C)c2C)cc(F)c1CN] | ++ | 472.0 [M − NH$_2$]$^+$ | 1.6 | A |
| 1.045 | 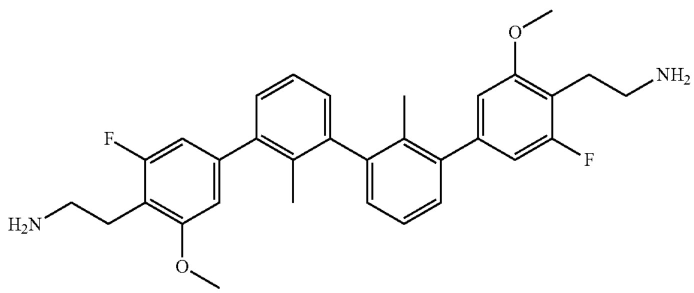 [SMILES: COc1cc(-c2cccc(-c3cccc(-c4cc(F)c(CCN)c(OC)c4)c3C)c2C)cc(F)c1CCN] | ++ | 517.2 [M + H]$^+$ | 2.4 | B |
| 1.046 | 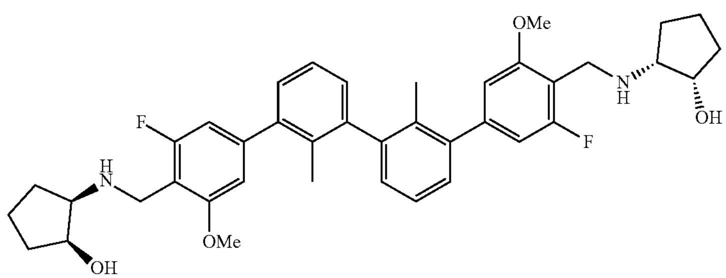 [SMILES: COc1cc(-c2cccc(-c3cccc(-c4cc(F)c(CN[C@@H]5CCC[C@@H]5O)c(OC)c4)c3C)c2C)cc(F)c1CN[C@@H]1CCC[C@@H]1O] | ++ | 657.3 [M + H]$^+$ | 2.1 | A |
| 1.047 | 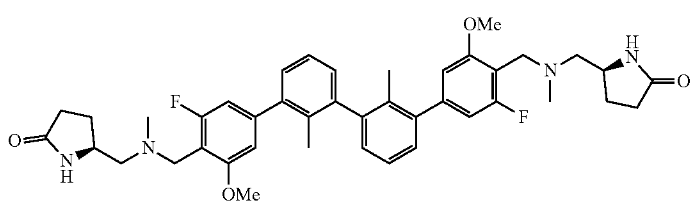 [SMILES: COc1cc(-c2cccc(-c3cccc(-c4cc(F)c(CN(C)C[C@@H]5CCC(=O)N5)c(OC)c4)c3C)c2C)cc(F)c1CN(C)C[C@@H]1CCC(=O)N1] | ++ | 711.3 [M + H]$^+$ | 1.7 | A |
| 1.048 | 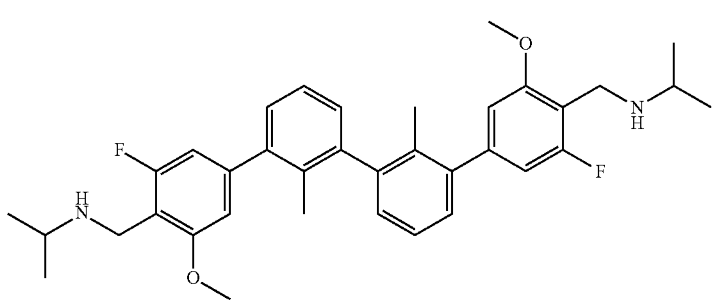 [SMILES: COc1cc(-c2cccc(-c3cccc(-c4cc(F)c(CNC(C)C)c(OC)c4)c3C)c2C)cc(F)c1CNC(C)C] | ++ | 573.3 [M + H]$^+$ | 2.3 | B |
| 1.049 | 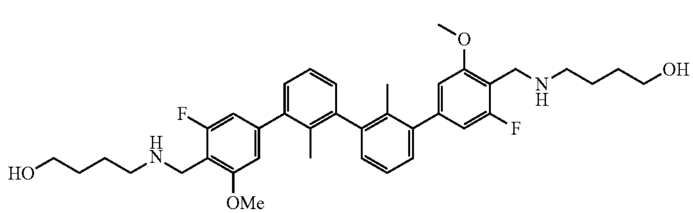 [SMILES: COc1cc(-c2cccc(-c3cccc(-c4cc(F)c(CNCCCCO)c(OC)c4)c3C)c2C)cc(F)c1CNCCCCO] | ++ | 633.3 [M + H]$^+$ | 1.5 | A |

TABLE 1-continued

| Compd ID | Structure | ELISA IC$_{50}$ (nM) | m/z ES | HPLC RT (min) | HPLC Method |
|---|---|---|---|---|---|
| 1.050 | 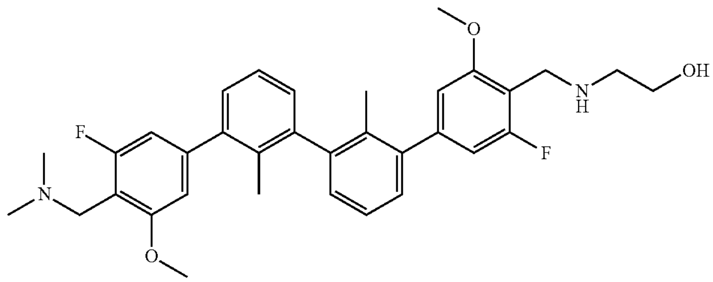 [SMILES: COc1cc(-c2cccc(-c3cccc(-c4cc(F)c(CN(C)C)c(OC)c4)c3C)c2C)cc(F)c1CNCCO] | ++ | 561.2 [M + H]$^+$ | 1.6 | A |
| 1.051 | 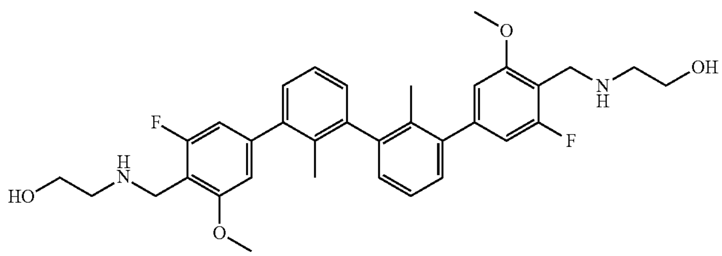 [SMILES: COc1cc(-c2cccc(-c3cccc(-c4cc(F)c(CNCCO)c(OC)c4)c3C)c2C)cc(F)c1CNCCO] | ++ | 577.2 [M + H]$^+$ | 1.6 | A |
| 1.052 | 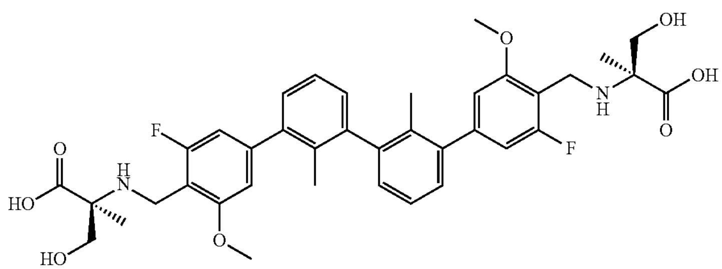 | ++ | 639.2 [M + H]$^+$ | 2.2 | B |
| 1.053 | 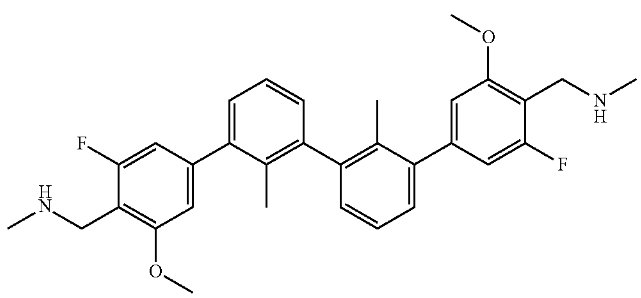 | ++ | 517.2 [M + H]$^+$ | 1.5 | A |
| 1.054 | 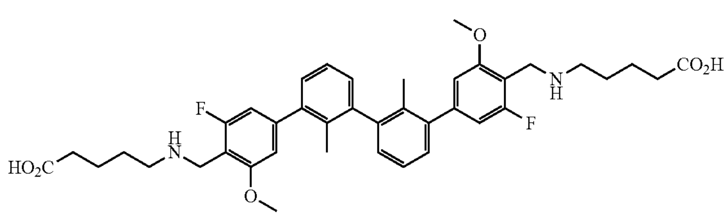 [SMILES: COc1cc(-c2cccc(-c3cccc(-c4cc(F)c(CNCCCCC(=O)O)c(OC)c4)c3C)c2C)cc(F)c1CNCCCCC(=O)O] | ++ | 689.3 [M + H]$^+$ | 2.3 | B |
| 1.055 | 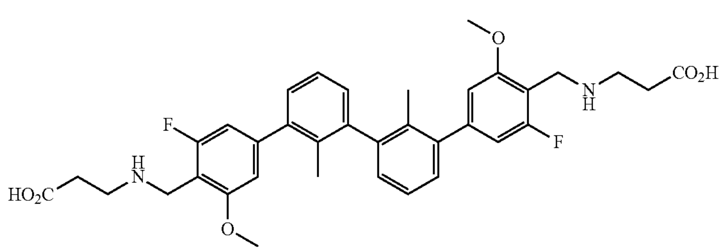 [SMILES: COc1cc(-c2cccc(-c3cccc(-c4cc(F)c(CNCCC(=O)O)c(OC)c4)c3C)c2C)cc(F)c1CNCCC(=O)O] | ++ | 633.2 [M + H]$^+$ | 2.2 | B |

TABLE 1-continued

| Compd ID | Structure | ELISA IC$_{50}$ (nM) | m/z ES | HPLC RT (min) | HPLC Method |
|---|---|---|---|---|---|
| 1.056 | 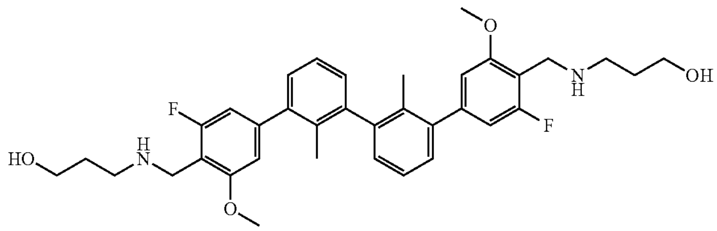 [SMILES: COc1cc(-c2cccc(-c3cccc(-c4cc(F)c(CNCCCO)c(OC)c4)c3C)c2C)cc(F)c1CNCCCO] | ++ | 605.3 [M + H]$^+$ | 1.6 | A |
| 1.057 | 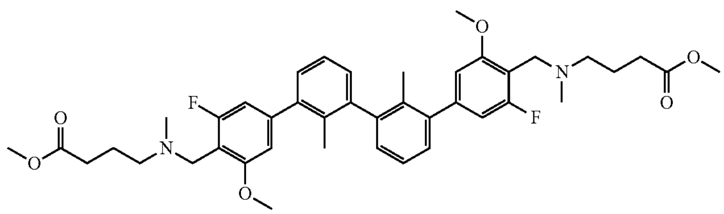 | ++ | 717.3 [M + H]$^+$ | 2.4 | B |
| 1.058 | 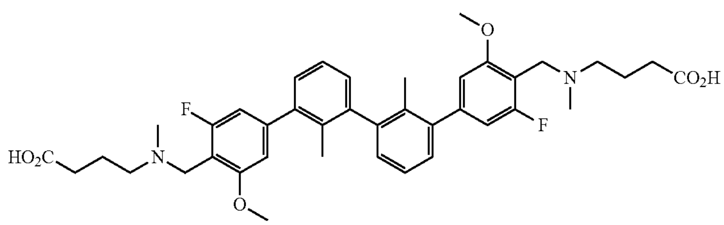 [SMILES: COc1cc(-c2cccc(-c3cccc(-c4cc(F)c(CN(C)CCCC(=O)O)c(OC)c4)c3C)c2C)cc(F)c1CN(C)CCCC(=O)O] | ++ | 689.3 [M + H]$^+$ | 2.3 | B |
| 1.059 | 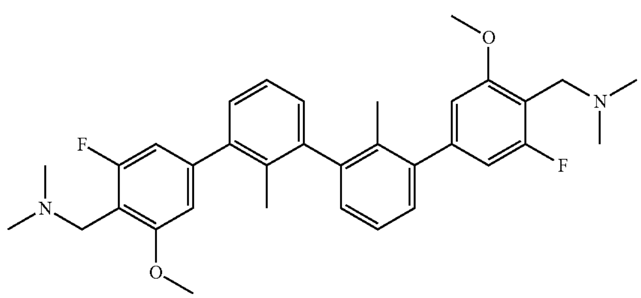 | ++ | 545.3 [M + H]$^+$ | 2.2 | B |
| 1.060 | 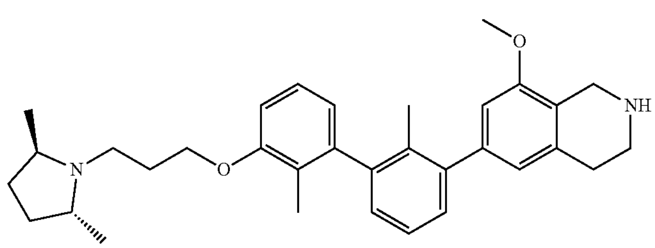 [SMILES: COc1cc(-c2cccc(-c3cccc(OCCCN4[C@H](C)CC[C@H]4C)c3C)c2C)cc2c1CNCC2] | ++ | 499.2 [M + H]$^+$ | 2.1 | B |
| 1.061 | 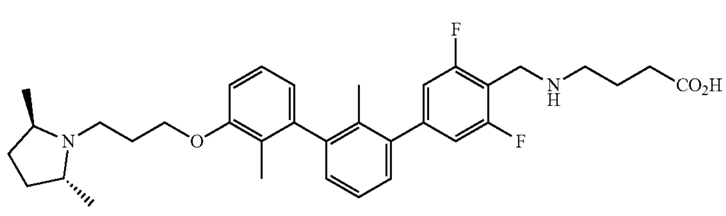 [SMILES: Cc1c(OCCCN2[C@H](C)CC[C@H]2C)cccc1-c1cccc(-c2cc(F)c(CNCCCC(=O)O)c(F)c2)c1C] | ++ | 565.2 [M + H]$^+$ | 2.0 | B |

TABLE 1-continued

| Compd ID | Structure | ELISA IC$_{50}$ (nM) | m/z ES | HPLC RT (min) | HPLC Method |
|---|---|---|---|---|---|
| 1.062 | 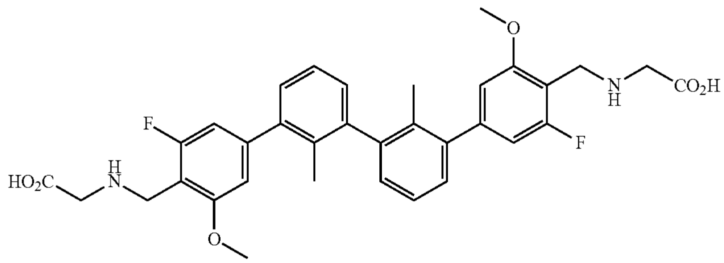 [SMILES: COc1cc(-c2cccc(-c3cccc(-c4cc(F)c(CNCC(=O)O)c(OC)c4)c3C)c2C)cc(F)c1CNCC(=O)O] | ++ | 605.2 [M + H]$^+$ | 2.2 | B |
| 1.063 | 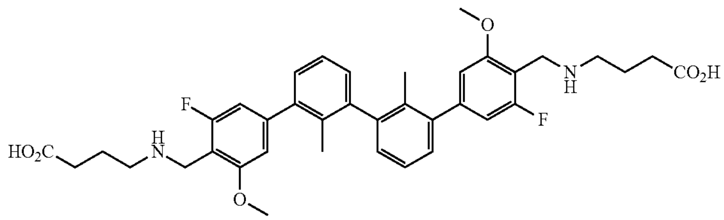 [SMILES: COc1cc(-c2cccc(-c3cccc(-c4cc(F)c(CNCCCC(=O)O)c(OC)c4)c3C)c2C)cc(F)c1CNCCCC(=O)O] | ++ | 661.2 [M + H]$^+$ | 2.2 | B |
| 1.064 | 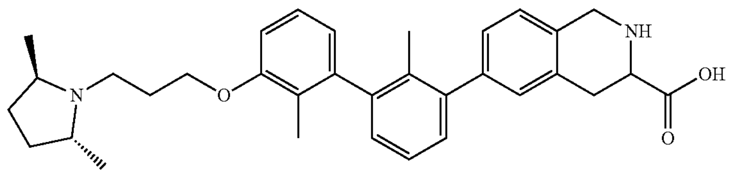 [SMILES: Cc1c(OCCCN2[C@H](C)CC[C@H]2C)cccc1-c1cccc(-c2ccc3c(c2)CC(C(=O)O)NC3)c1C] | + | 513.3 [M + H]$^+$ | 2.2 | B |
| 1.065 | 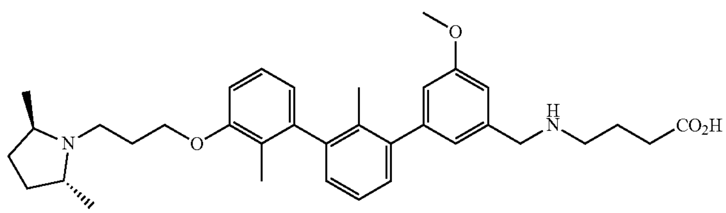 [SMILES: COc1cc(CNCCCC(=O)O)cc(-c2cccc(-c3cccc(OCCCN4[C@H](C)CC[C@H]4C)c3C)c2C)c1] | + | 559.3 [M + H]$^+$ | 2.2 | B |
| 1.066 | 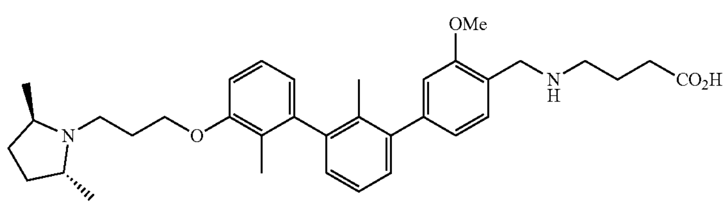 [SMILES: COc1cc(-c2cccc(-c3cccc(OCCCN4[C@H](C)CC[C@H]4C)c3C)c2C)ccc1CNCCCC(=O)O] | ++ | 559.3 [M + H]$^+$ | 2.2 | B |
| 1.067 | 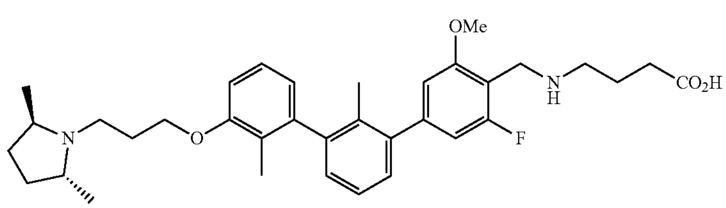 [SMILES: COc1cc(-c2cccc(-c3cccc(OCCCN4[C@H](C)CC[C@H]4C)c3C)c2C)cc(F)c1CNCCCC(=O)O] | ++ | 577.3 [M + H]$^+$ | 2.1 | B |
| 1.068 | 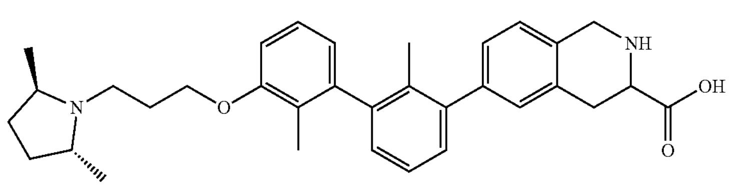 [SMILES: Cc1c(OCCCN2[C@H](C)CC[C@H]2C)cccc1-c1cccc(-c2ccc3c(c2)CC(C(=O)O)NC3)c1C] | ++ | 513.3 [M + H]$^+$ | 2.0 | B |

TABLE 1-continued

| Compd ID | Structure | ELISA IC$_{50}$ (nM) | m/z ES | HPLC RT (min) | HPLC Method |
|---|---|---|---|---|---|
| 1.069 | 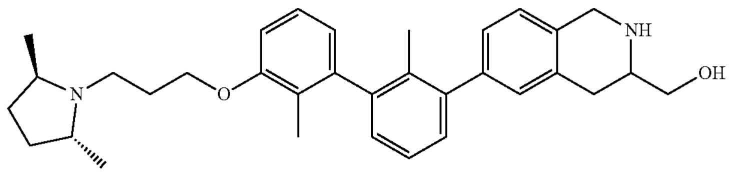 [SMILES: Cc1c(OCCCN2[C@H](C)CC[C@H]2C)cccc1-c1cccc(-c2ccc3c(c2)CC(CO)NC3)c1C] | ++ | 499.2 [M + H]$^+$ | 2.1 | B |
| 1.070 | 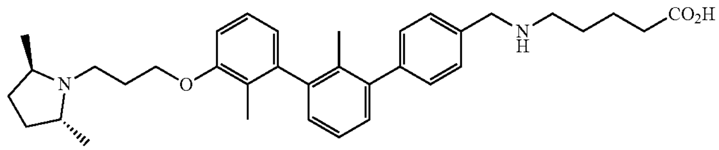 [SMILES: Cc1c(OCCCN2[C@H](C)CC[C@H]2C)cccc1-c1cccc(-c2ccc(CNCCCCC(=O)O)cc2)c1C] | + | 525.3 [M + H]$^+$ | 2.5 | B |
| 1.071 | 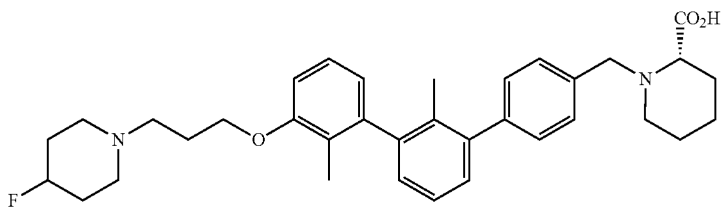 [SMILES: Cc1c(OCCCN2CCC(F)CC2)cccc1-c1cccc(-c2ccc(CN3CCCC[C@H]3C(=O)O)cc2)c1C] | + | 559.2 [M + H]$^+$ | 2.0 | B |
| 1.072 | 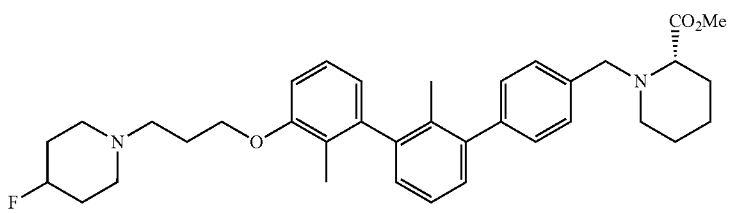 [SMILES: COC(=O)[C@@H]1CCCCN1Cc1ccc(-c2cccc(-c3cccc(OCCCN4CCC(F)CC4)c3C)c2C)cc1] | + | 573.3 [M + H]$^+$ | 2.2 | B |
| 1.073 | 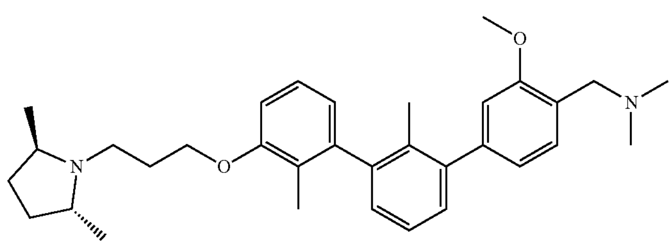 [SMILES: COc1cc(-c2cccc(-c3cccc(OCCCN4[C@H](C)CC[C@H]4C)c3C)c2C)ccc1CN(C)C] | ++ | 501.3 [M + H]$^+$ | 2.2 | B |
| 1.074 | 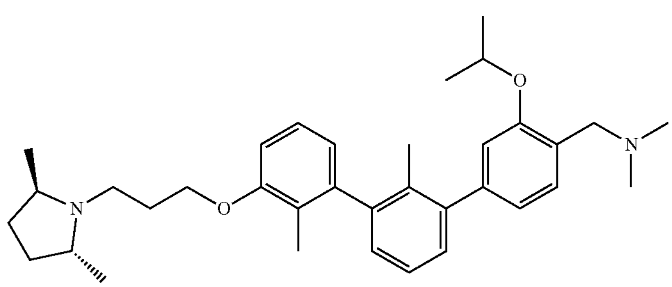 [SMILES: Cc1c(OCCCN2[C@H](C)CC[C@H]2C)cccc1-c1cccc(-c2ccc(CN(C)C)c(OC(C)C)c2)c1C] | ++ | 529.3 [M + H]$^+$ | 2.1 | B |
| 1.075 | 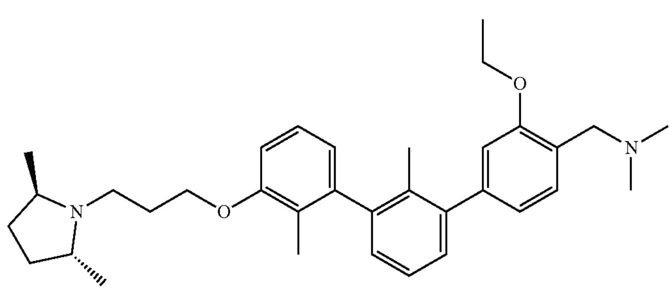 [SMILES: CCOc1cc(-c2cccc(-c3cccc(OCCCN4[C@H](C)CC[C@H]4C)c3C)c2C)ccc1CN(C)C] | ++ | 515.2 [M + H]$^+$ | 2.1 | B |

…
TABLE 1-continued
| Compd ID | Structure | ELISA IC$_{50}$ (nM) | m/z ES | HPLC RT (min) | HPLC Method |
|---|---|---|---|---|---|
| 1.076 | 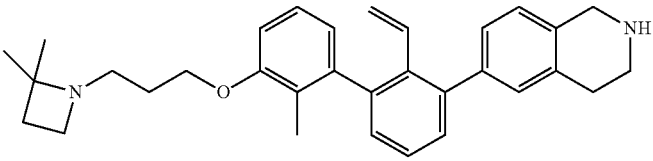 [SMILES: C=Cc1c(-c2ccc3c(c2)CCNC3)cccc1-c1cccc(OCCCN2CCC2(C)C)c1C] | ++ | 467.3 [M + H]$^+$ | 2.2 | B |
| 1.077 | 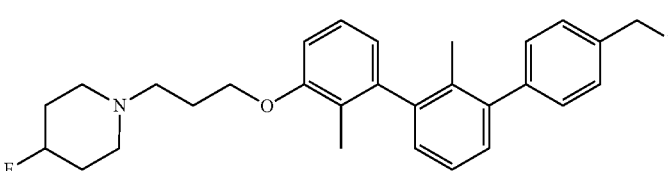 | ++ | 447.1 [M + H]$^+$ | 2.0 | B |
| 1.078 | 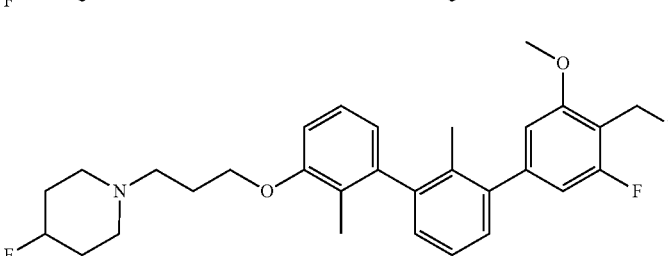 | ++ | 523.2 [M + H]$^+$ | 1.8 | B |
| 1.079 | 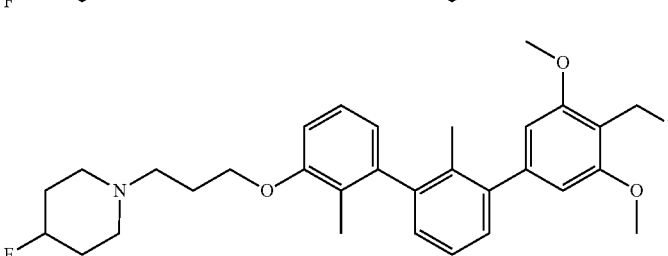 | + | 535.2 [M + H]$^+$ | 2.1 | B |
| 1.080 | 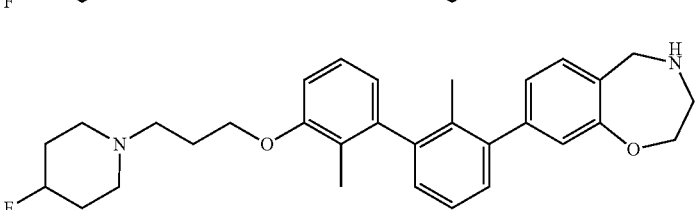 | ++ | 489.2 [M + H]$^+$ | 1.9 | B |
| 1.081 | 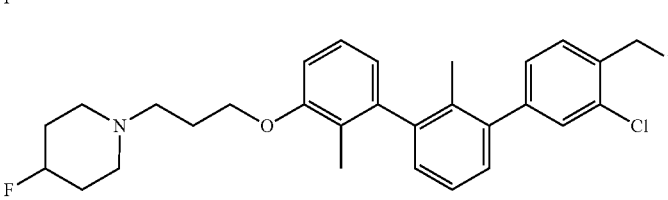 | ++ | 509.2 [M + H]$^+$ | 2.0 | B |
| 1.082 | 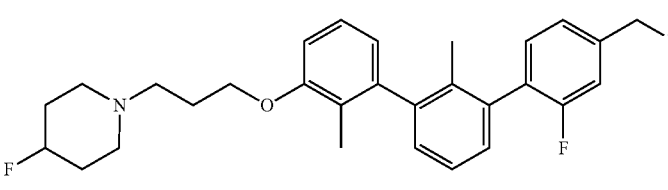 | ++ | 465.1 [M + H]$^+$ | 2.0 | B |
| 1.083 | 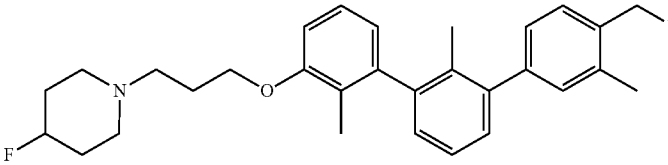 | ++ | 489.3 [M + H]$^+$ | 2.1 | B |

TABLE 1-continued

| Compd ID | Structure | ELISA IC$_{50}$ (nM) | m/z ES | HPLC RT (min) | HPLC Method |
|---|---|---|---|---|---|
| 1.084 | 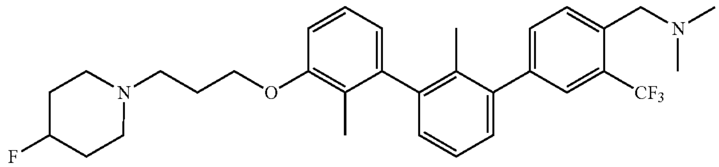 [SMILES: Cc1c(OCCCN2CCC(F)CC2)cccc1-c1cccc(-c2ccc(CN(C)C)c(C(F)(F)F)c2)c1C] | + | 543.2 [M + H]$^+$ | 2.2 | B |
| 1.085 | 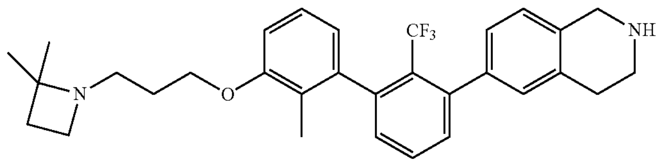 | + | 509.4 [M + H]$^+$ | 1.6 | A |
| 1.086 | 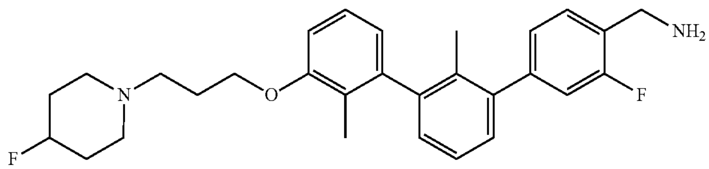 [SMILES: Cc1c(OCCCN2CCC(F)CC2)cccc1-c1cccc(-c2ccc(CN)c(F)c2)c1C] | ++ | 465.1 [M + H]$^+$ | 2.0 | B |
| 1.087 | 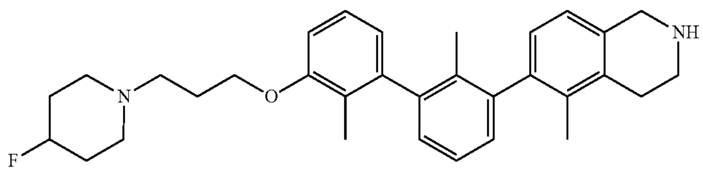 [SMILES: Cc1c(OCCCN2CCC(F)CC2)cccc1-c1cccc(-c2ccc3c(c2C)CCNC3)c1C] | + | 487.2 [M + H]$^+$ | 1.8 | B |
| 1.088 | 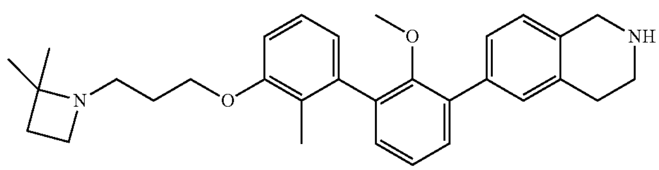 [SMILES: COc1c(-c2ccc3c(c2)CCNC3)cccc1-c1cccc(OCCCN2CCC2(C)C)c1C] | ++ | 471.4 [M + H]$^+$ | 2.1 | B |
| 1.089 | 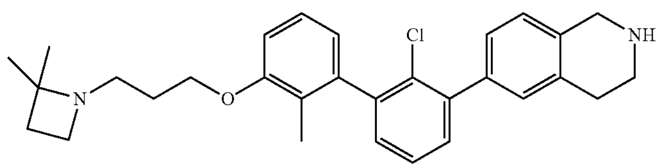 [SMILES: Cc1c(OCCCN2CCC2(C)C)cccc1-c1cccc(-c2ccc3c(c2)CCNC3)c1Cl] | ++ | 475.3 [M + H]$^+$ | 2.1 | B |
| 1.090 | 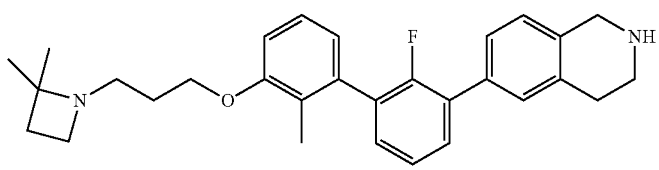 | ++ | 459.4 [M + H]$^+$ | 2.1 | B |
| 1.091 | 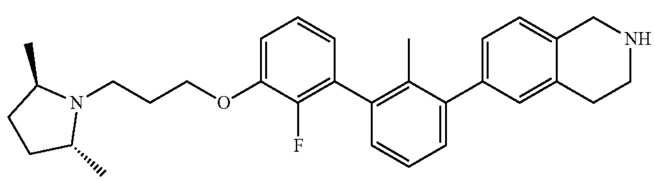 [SMILES: Cc1c(-c2ccc3c(c2)CCNC3)cccc1-c1cccc(OCCCN2[C@H](C)CC[C@H]2C)c1F] | ++ | 473.3 [M + H]$^+$ | 1.7 | A |
| 1.092 | 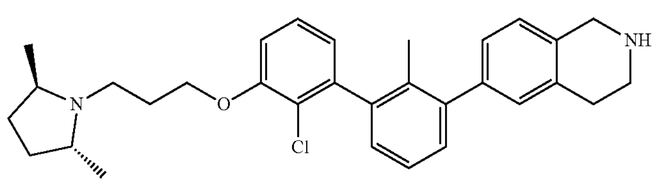 [SMILES: Cc1c(-c2ccc3c(c2)CCNC3)cccc1-c1cccc(OCCCN2[C@H](C)CC[C@H]2C)c1Cl] | ++ | 489.1 [M + H]$^+$ | 1.4 | A |

TABLE 1-continued

| Compd ID | Structure | ELISA IC$_{50}$ (nM) | m/z ES | HPLC RT (min) | HPLC Method |
|---|---|---|---|---|---|
| 1.093 | 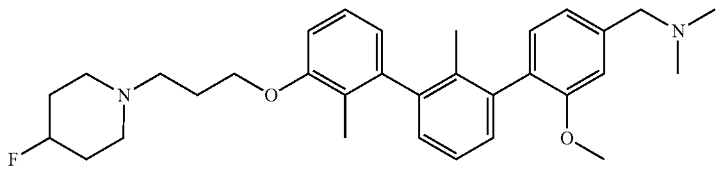 [SMILES: COc1cc(CN(C)C)ccc1-c1cccc(-c2cccc(OCCCN3CCC(F)CC3)c2C)c1C] | + | 505.2 [M + H]$^+$ | 1.9 | B |
| 1.094 | 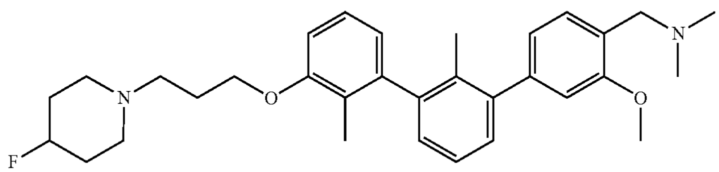 [SMILES: COc1cc(-c2cccc(-c3cccc(OCCCN4CCC(F)CC4)c3C)c2C)ccc1CN(C)C] | ++ | 505.2 [M + H]$^+$ | 1.7 | B |
| 1.095 | 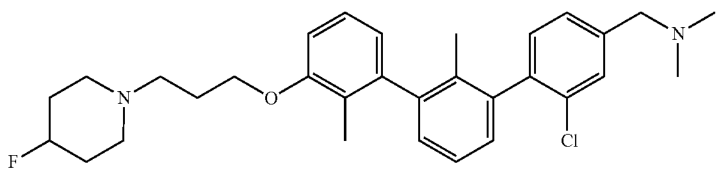 [SMILES: Cc1c(OCCCN2CCC(F)CC2)cccc1-c1cccc(-c2ccc(CN(C)C)cc2Cl)c1C] | + | 509.2 [M + H]$^+$ | 1.9 | B |
| 1.096 | 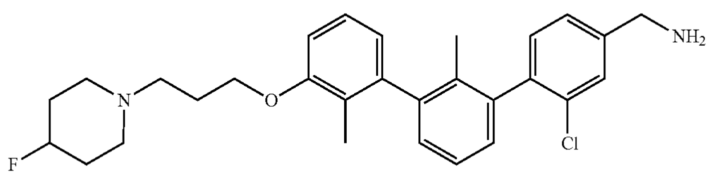 | + | 481.2 [M + H]$^+$ | 2.0 | B |
| 1.097 | 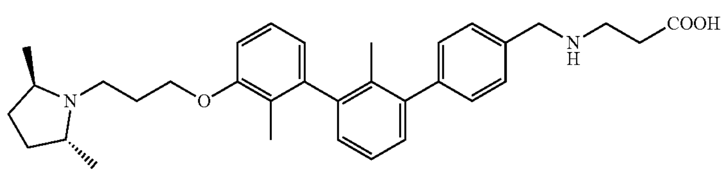 [SMILES: Cc1c(OCCCN2[C@H](C)CC[C@H]2C)cccc1-c1cccc(-c2ccc(CNCCC(=O)O)cc2)c1C] | ++ | 515.2 [M + H]$^+$ | 2.0 | B |
| 1.098 | 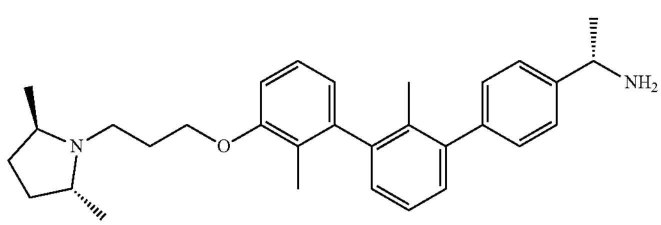 [SMILES: Cc1c(OCCCN2[C@H](C)CC[C@H]2C)cccc1-c1cccc(-c2ccc([C@H](C)N)cc2)c1C] | ++ | 457.2 [M + H]$^+$ | 2.1 | B |
| 1.099 | 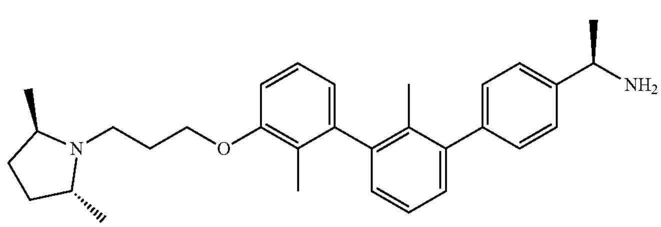 [SMILES: Cc1c(OCCCN2[C@H](C)CC[C@H]2C)cccc1-c1cccc(-c2ccc([C@@H](C)N)cc2)c1C] | ++ | 457.2 [M + H]$^+$ | 1.9 | B |
| 1.100 | 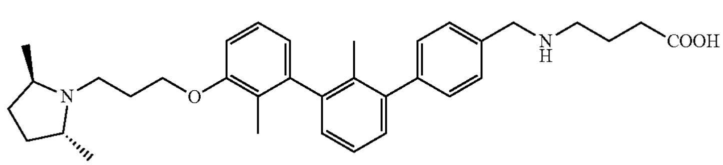 [SMILES: Cc1c(OCCCN2[C@H](C)CC[C@H]2C)cccc1-c1cccc(-c2ccc(CNCCCC(=O)O)cc2)c1C] | ++ | 529.3 [M + H]$^+$ | 2.0 | B |

TABLE 1-continued

| Compd ID | Structure | ELISA IC$_{50}$ (nM) | m/z ES | HPLC RT (min) | HPLC Method |
|---|---|---|---|---|---|
| 1.101 | 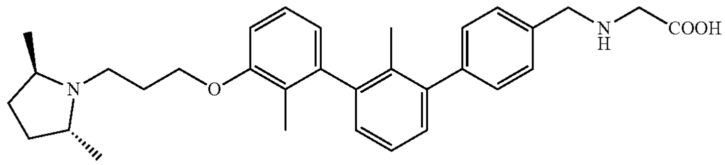 [SMILES: Cc1c(OCCCN2[C@H](C)CC[C@H]2C)cccc1-c1cccc(-c2ccc(CNCC(=O)O)cc2)c1C] | ++ | 501.3 [M + H]$^+$ | 2.1 | B |
| 1.102 | 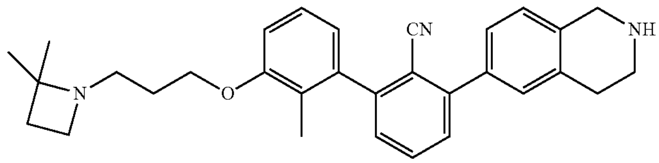 [SMILES: Cc1c(OCCCN2CCC2(C)C)cccc1-c1cccc(-c2ccc3c(c2)CCNC3)c1C#N] | ++ | 466.4 [M + H]$^+$ | 1.9 | B |
| 1.103 | 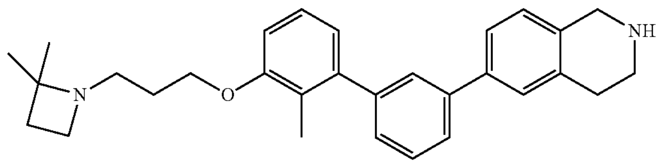 [SMILES: Cc1c(OCCCN2CCC2(C)C)cccc1-c1cccc(-c2ccc3c(c2)CCNC3)c1] | + | 441.3 [M + H]$^+$ | 1.9 | B |
| 1.104 | 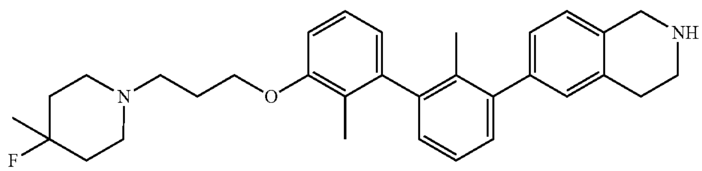 [SMILES: Cc1c(OCCCN2CCC(C)(F)CC2)cccc1-c1cccc(-c2ccc3c(c2)CCNC3)c1C] | ++ | 487.2 [M + H]$^+$ | 2.0 | B |
| 1.105 | 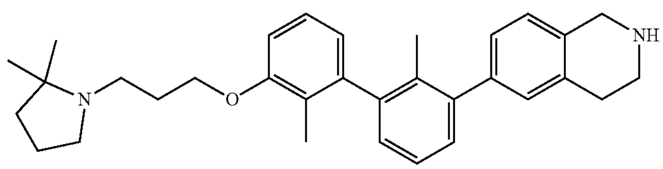 [SMILES: Cc1c(OCCCN2CCCC2(C)C)cccc1-c1cccc(-c2ccc3c(c2)CCNC3)c1C] | ++ | 469.2 [M + H]$^+$ | 2.0 | B |
| 1.106 | 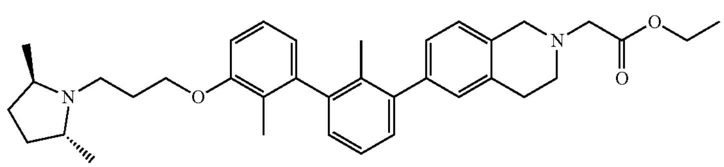 [SMILES: CCOC(=O)CN1CCc2cc(-c3cccc(-c4cccc(OCCCN5[C@H](C)CC[C@H]5C)c4C)c3C)ccc2C1] | + | 555.3 [M + H]$^+$ | 1.7 | A |
| 1.107 | 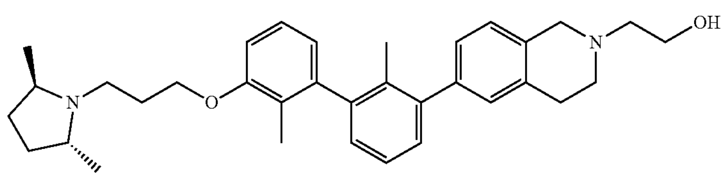 [SMILES: Cc1c(OCCCN2[C@H](C)CC[C@H]2C)cccc1-c1cccc(-c2ccc3c(c2)CCN(CCO)C3)c1C] | ++ | 513.3 [M + H]$^+$ | 1.9 | A |
| 1.108 | 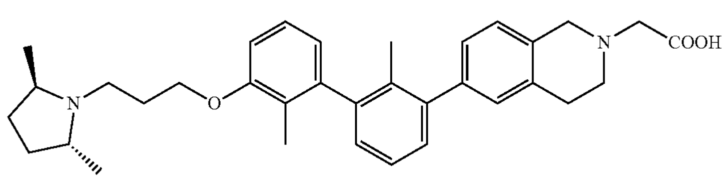 [SMILES: Cc1c(OCCCN2[C@H](C)CC[C@H]2C)cccc1-c1cccc(-c2ccc3c(c2)CCN(CC(=O)O)C3)c1C] | ++ | 527.2 [M + H]$^+$ | 1.7 | A |
| 1.109 | 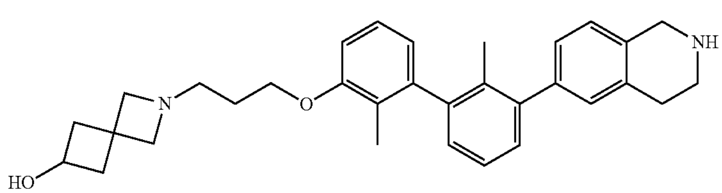 [SMILES: Cc1c(OCCCN2CC3(CC(O)C3)C2)cccc1-c1cccc(-c2ccc3c(c2)CCNC3)c1C] | ++ | 483.3 [M + H]$^+$ | 1.7 | B |

TABLE 1-continued

| Compd ID | Structure | ELISA IC$_{50}$ (nM) | m/z ES | HPLC RT (min) | HPLC Method |
|---|---|---|---|---|---|
| 1.110 | 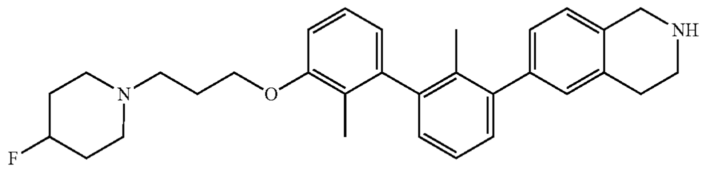 [SMILES: Cc1c(OCCCN2CCC(F)CC2)cccc1-c1cccc(-c2ccc3c(c2)CCNC3)c1C] | ++ | 473.3 [M + H]$^+$ | 2.1 | B |
| 1.111 | 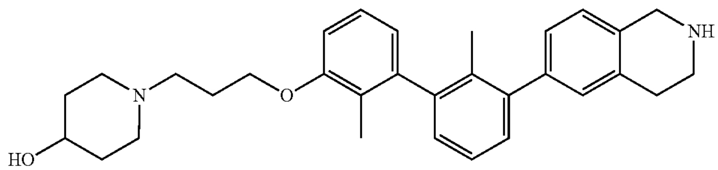 [SMILES: Cc1c(OCCCN2CCC(O)CC2)cccc1-c1cccc(-c2ccc3c(c2)CCNC3)c1C] | ++ | 471.3 [M + H]$^+$ | 1.9 | B |
| 1.112 | 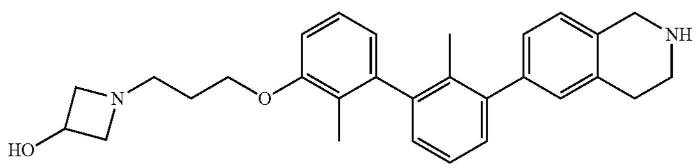 [SMILES: Cc1c(OCCCN2CC(O)C2)cccc1-c1cccc(-c2ccc3c(c2)CCNC3)c1C] | ++ | 443.2 [M + H]$^+$ | 2.0 | B |
| 1.113 | 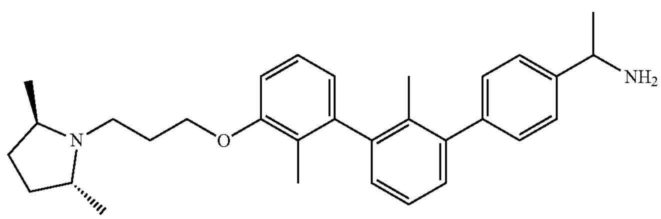 [SMILES: Cc1c(OCCCN2[C@H](C)CC[C@H]2C)cccc1-c1cccc(-c2ccc(C(C)N)cc2)c1C] | ++ | 457.2 [M + H]$^+$ | 1.4 | A |
| 1.114 | 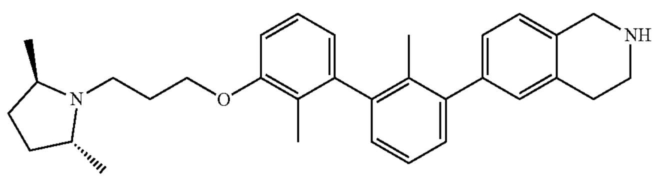 [SMILES: Cc1c(OCCCN2[C@H](C)CC[C@H]2C)cccc1-c1cccc(-c2ccc3c(c2)CCNC3)c1C] | ++ | 469.2 [M + H]$^+$ | 1.4 | A |
| 1.115 | 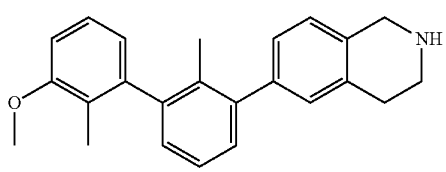 [SMILES: COc1cccc(-c2cccc(-c3ccc4c(c3)CCNC4)c2C)c1C] | + | 344.2 [M + H]$^+$ | 2.0 | A |
| 1.116 | 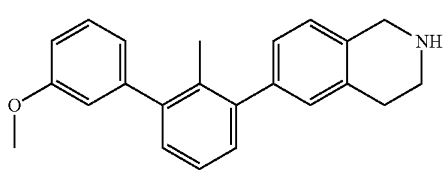 [SMILES: COc1cccc(-c2cccc(-c3ccc4c(c3)CCNC4)c2C)c1] | + | 330.1 [M + H]$^+$ | 1.9 | A |
| 1.117 | 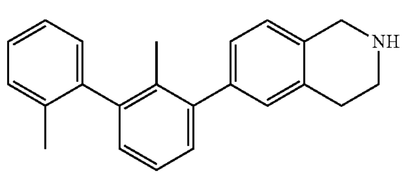 [SMILES: Cc1ccccc1-c1cccc(-c2ccc3c(c2)CCNC3)c1C] | + | 314.1 [M + H]$^+$ | 2.0 | A |

TABLE 1-continued

| Compd ID | Structure | ELISA IC$_{50}$ (nM) | m/z ES | HPLC RT (min) | HPLC Method |
|---|---|---|---|---|---|
| 1.118 | 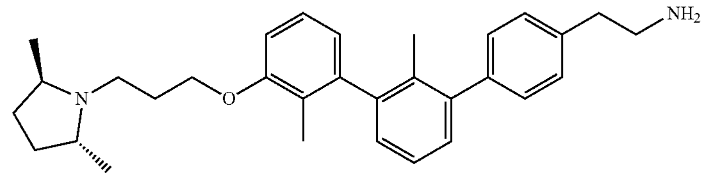 [SMILES: Cc1c(OCCCN2[C@H](C)CC[C@H]2C)cccc1-c1cccc(-c2ccc(CCN)cc2)c1C] | ++ | 457.0 [M + H]$^+$ | 1.6 | A |
| 1.119 | 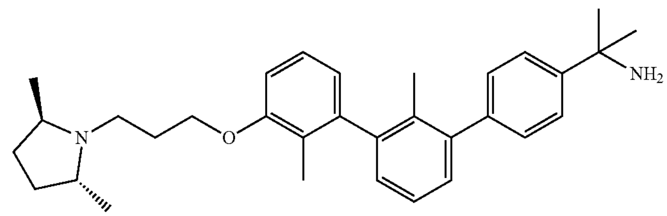 [SMILES: Cc1c(OCCCN2[C@H](C)CC[C@H]2C)cccc1-c1cccc(-c2ccc(C(C)(C)N)cc2)c1C] | ++ | 471.3 [M + H]$^+$ | 1.4 | A |
| 1.120 | 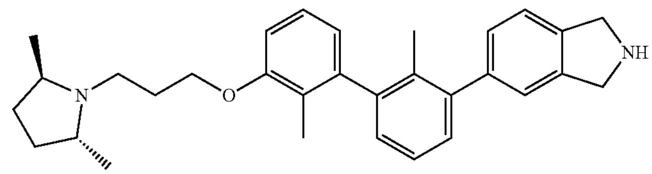 [SMILES: Cc1c(OCCCN2[C@H](C)CC[C@H]2C)cccc1-c1cccc(-c2ccc3c(c2)CNC3)c1C] | ++ | 455.3 [M + H]$^+$ | 1.4 | A |
| 1.121 | 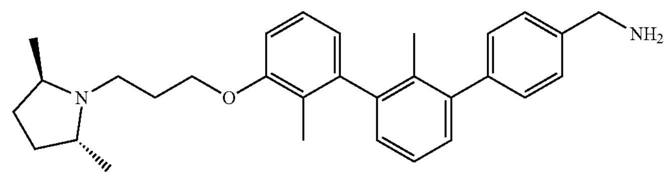 [SMILES: Cc1c(OCCCN2[C@H](C)CC[C@H]2C)cccc1-c1cccc(-c2ccc(CN)cc2)c1C] | ++ | 443.2 [M + H]$^+$ | 1.6 | A |
| 1.122 | 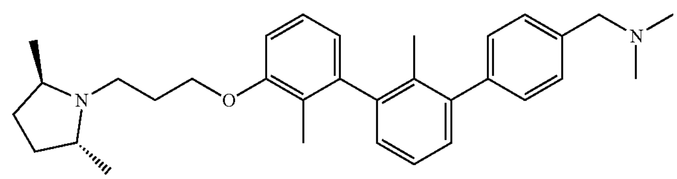 [SMILES: Cc1c(OCCCN2[C@H](C)CC[C@H]2C)cccc1-c1cccc(-c2ccc(CN(C)C)cc2)c1C] | ++ | 471.3 [M + H]$^+$ | 1.7 | A |
| 1.123 | 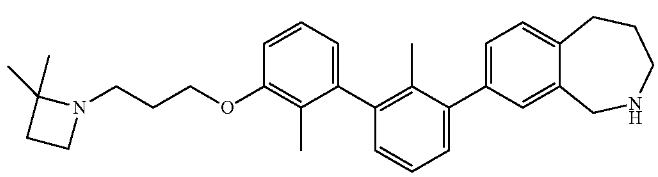 [SMILES: Cc1c(OCCCN2CCC2(C)C)cccc1-c1cccc(-c2ccc3c(c2)CNCCC3)c1C] | ++ | 469.2 [M + H]$^+$ | 1.6 | A |
| 1.124 | 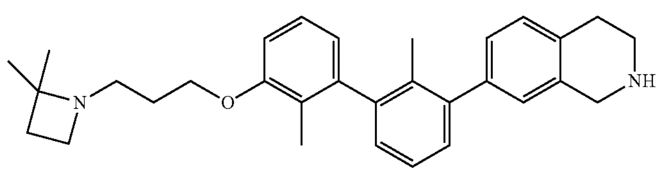 [SMILES: Cc1c(OCCCN2CCC2(C)C)cccc1-c1cccc(-c2ccc3c(c2)CNCC3)c1C] | ++ | 455.3 [M + H]$^+$ | 1.8 | A |
| 1.125 | 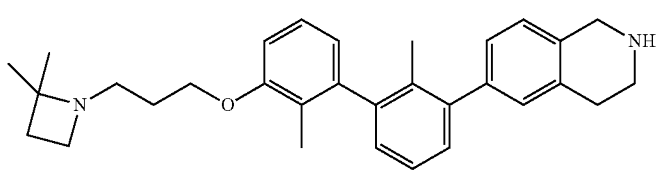 [SMILES: Cc1c(OCCCN2CCC2(C)C)cccc1-c1cccc(-c2ccc3c(c2)CCNC3)c1C] | ++ | 455.3 [M + H]$^+$ | 1.7 | A |

TABLE 1-continued

| Compd ID | Structure | ELISA IC$_{50}$ (nM) | m/z ES | HPLC RT (min) | HPLC Method |
|---|---|---|---|---|---|
| 1.126 | 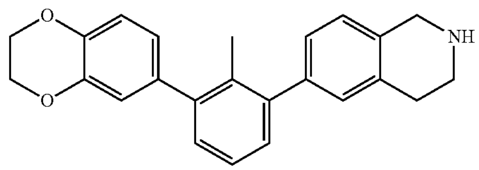 [SMILES: Cc1c(-c2ccc3c(c2)CCNC3)cccc1-c1ccc2c(c1)OCCO2] | ++ | 358.2 [M + H]$^+$ | 2.1 | A |
| 1.127 | 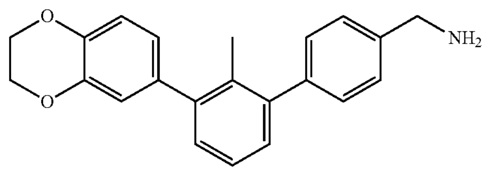 | + | 315.1 [M + H]$^+$ | 1.9 | A |
| 1.128 | 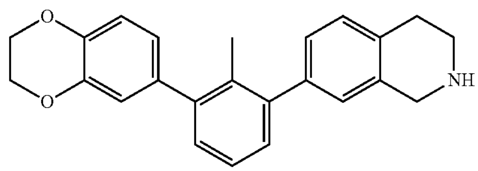 [SMILES: Cc1c(-c2ccc3c(c2)CNCC3)cccc1-c1ccc2c(c1)OCCO2] | + | 358.2 [M + H]$^+$ | 1.7 | A |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound of Formula (I):

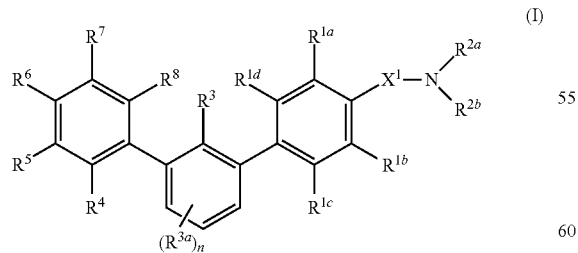

(I)

or a pharmaceutically acceptable salt thereof, or a prodrug or bioisostere thereof, wherein:

$R^{1a}$, $R^{1b}$, $R^{1c}$ and $R^{1d}$ are each independently selected from the group consisting of H, F, Cl, $C_{1-3}$ alkyl, $C_{1-3}$ haloalkyl, $C_{1-3}$ alkoxy and CN;

$X^1$ is $C_{1-3}$ alkylene, optionally substituted with one or two $C_{1-2}$ alkyl or $CO_2H$;

$R^{2a}$ and $R^{2b}$ are each independently selected from the group consisting of H, $C_{1-2}$ alkyl, $C_{1-8}$ haloalkyl, —Y, —$X^2$—C(O)$_2R^a$, —$X^2$—OR$^a$, —$X^2$—NR$^a$R$^b$, —$X^2$—CONR$^a$R$^b$, —$X^2$—SO$_2$R$^a$, —$X^2$—SO$_2$NR$^a$R$^b$, —$X^2$—SO$_3$R$^a$ and —$X^2$—Y wherein each $X^2$ is $C_{1-6}$ alkylene and any $C_{1-8}$ alkyl or $C_{1-6}$ alkylene, is optionally further substituted with one or two members independently selected from OH, SO$_2$NH$_2$, CONH$_2$, C(O)NHOH, PO$_3$H$_2$, COO—$C_{1-8}$alkyl or CO$_2$H, and each Y is selected from the group consisting of $C_{3-6}$ cycloalkyl, $C_{4-8}$ heterocyclyl and 5- to 6-membered heteroaryl, each of which is optionally further substituted with one to four substituents independently selected from the group consisting of oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, SO$_2$NH$_2$, CONH$_2$, C(O)NHOH, PO$_3$H$_2$, COO—$C_{1-8}$alkyl, and CO$_2$H;

or $R^{2a}$ and $R^{2b}$ are combined to form a 4- to 8-membered ring or spirocyclic ring, optionally having one or two additional ring vertices selected from O, N or S;

or $R^{1a}$ and $R^{2a}$ or $X^1$ are combined to form a 5- to 7-membered ring;

or $R^{1b}$ and $R^{2b}$ or $X^1$ are combined to form a 5- to 7-membered ring;

wherein the rings formed by combining $R^{2a}$ and $R^{2b}$, $R^{1a}$ and $R^{2a}$ or $X^1$, or $R^{1b}$ and $R^{2b}$ or $X^1$, are substituted with 0 to 4 substituents independently selected from the group consisting of oxo, $C_{1-8}$ alkyl, $C_{1-8}$ haloalkyl, —$X^3$—C(O)$_2R^a$, —$X^3$—OR$^a$, —$X^3$—NR$^a$R$^b$, —$X^3$—CONR$^a$R$^b$, —$X^3$—SO$_2$R$^a$, —$X^3$—SO$_2$NR$^a$R$^b$, and —$X^3$—SO$_3$R$^a$; wherein $X^3$ is a bond or $C_{1-6}$ alkylene;

$R^3$ is selected from the group consisting of H, F, Cl, $C_{1-3}$ alkyl, $C_{1-3}$ alkoxy, $C_{1-3}$ haloalkyl, $C_{1-3}$ haloalkoxy, $C_{2-3}$ alkenyl and CN;

the subscript n is 0, 1 or 2;

each $R^{3a}$ is independently selected from the group consisting of F, Cl, $C_{1-3}$ alkyl, $C_{1-3}$ alkoxy, $C_{1-3}$ haloalkyl, $C_{1-3}$ haloalkoxy, $C_{2-3}$ alkenyl and CN;

each of $R^4$, $R^6$, $R^7$ and $R^8$ is independently selected from the group consisting of H, halogen, CN, $C_{1-6}$ alkyl, $C_{2-6}$ alkenyl, $C_{2-6}$ alkynyl, $C_{1-6}$ haloalkyl, $C_{1-6}$ hydroxyalkyl, $-Y^1$, $-X^4-C(O)_2R^a$, $-X^4-OR^a$, $-X^4-NR^aR^b$, $-X^4-CONR^aR^b$, $-X^4-SO_2R^a$, $-X^4-SO_2NR^aR^b$, $-X^4-SO_3R^a$, $-O-X^4-Y^1$ and $-X^4-Y^1$ wherein each $X^4$ is a bond or $C_{1-6}$ alkylene and is optionally further substituted with OH, $SO_2NH_2$, $CONH_2$, $C(O)NHOH$, $PO_3H_2$, $COO-C_{1-8}$alkyl or $CO_2H$, and each $Y^1$ is selected from the group consisting of $C_{3-6}$ cycloalkyl, $C_{4-8}$ heterocyclyl and 5- to 6-membered heteroaryl, each of which is optionally further substituted with one to four substituents independently selected from the group consisting of oxo, OH, $C_{1-4}$ alkyl, $C_{1-4}$ haloalkyl, $C_{1-4}$hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO-C_{1-8}$alkyl, and $CO_2H$;

$R^5$ is a member selected from the group consisting of H, halogen, CN, $C_{1-6}$ alkyl, $C_{1-6}$ haloalkyl, $C_{1-6}$ hydroxyalkyl, $-Y^2$, $-X^5-C(O)_2R^a$, $-X^5-OR^a$, $-X^5-NR^aR^b$, $-X^5-CONR^aR^b$, $-X^5-SO_2R^a$, $-X^5-SO_2NR^aR^b$, $-X^5-SO_3R^a$, $-X^5-Y^2$, $-O-X^5-Y^2$ and -A-Z, wherein each $X^5$ is a bond or $C_{1-6}$ alkylene and is optionally further substituted with OH, $SO_2NH_2$, $CONH_2$, $C(O)NHOH$, $PO_3H_2$, $COO-C_{1-8}$alkyl or $CO_2H$, and each $Y^2$ is selected from the group consisting of $C_{3-6}$ cycloalkyl, $C_{4-8}$ heterocyclyl, $C_{7-9}$ spiroheterocyclyl, and 5- to 6-membered heteroaryl, each of which is optionally further substituted with one to four substituents independently selected from the group consisting of oxo, halogen, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO-C_{1-8}$alkyl, and $CO_2H$;

wherein

A is a member selected from the group consisting of a bond, $-O-$ and $N(R^a)$;

Z is selected from the group consisting of:
  i) a monocyclic 5- or 6-membered heteroaryl ring, optionally substituted with one to three $R^c$;
  ii) phenyl, optionally substituted with one to three Re; and
  iii) a 5- or 6-membered non-aromatic heterocyclic ring, optionally substituted with one to three $R^c$;
  and when A is $-O-$ or $N(R^a)-$, then Z is other than phenyl;

and two of $R^4$, $R^5$, $R^6$, $R^7$ and $R^8$ on adjacent carbon atoms are optionally combined to form a 5- or 6-membered non-aromatic heterocyclic ring having one or two ring vertices selected from the group consisting of O, $-N(R^b)-$ and $=N-$; wherein said non-aromatic heterocyclic ring is optionally substituted with oxo and optionally with from one to four $R^e$;

and at least one of $R^4$, $R^5$, $R^6$, $R^7$ and $R^8$ is other than H;

each $R^a$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2H$, $C_{1-6}$ alkylene-$COO-C_{1-8}$alkyl, $C_{1-6}$ alkylene-$SO_3H$;

each $R^b$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2H$, $C_{1-6}$ alkylene-$SO_3H$ and $C_{1-6}$ alkylene-$Y^3$, wherein $Y^3$ is $C_{3-6}$ cycloalkyl or $C_{4-8}$ heterocyclyl, and each $R^b$ is optionally further substituted with one or two members independently selected from oxo, OH, $SO_2NH_2$, $CONH_2$, $C(O)NHOH$, $PO_3H_2$, $COO-C_{1-8}$alkyl and $CO_2H$;

and $R^a$ and $R^b$, when attached to the same nitrogen atom, are optionally combined to form a 4- to 8-membered ring or spirocyclic ring, optionally substituted with halogen, OH, $SO_2NH_2$, $CONH_2$, $C(O)NHOH$, $PO_3H_2$, $COO-C_{1-8}$alkyl or $CO_2H$;

each $R^c$ is independently selected from the group consisting of H, halogen, CN, $C_{1-6}$ alkyl, $C_{1-6}$ haloalkyl, $-Y^4$, $-X^6-C(O)_2R^a$, $-X^6-OR^a$, $-X^6-NR^aR^b$, $-X^6-CONR^aR^b$, $-X^6-SO_2R^a$, $-X^6-SO_2NR^aR^b$, $-X^6-SO_3R^a$, and $-N(R^a)-X^6-C(O)_2R^a$, wherein each $X^6$ is a bond or $C_{1-6}$ alkylene, and each $Y^4$ is selected from the group consisting of $C_{3-6}$ cycloalkyl and $C_{4-8}$ heterocyclyl; and optionally two $R^c$ on adjacent ring vertices are combined to form a fused 5- or 6-membered heterocyclic ring.

2. The compound of claim 1, or a pharmaceutically acceptable salt thereof wherein $R^5$ is -A-Z.

3. The compound of claim 1, or a pharmaceutically acceptable salt thereof wherein $R^5$ is $-O-X^5-Y^2$.

4. The compound of claim 1, or a pharmaceutically acceptable salt thereof wherein $R^5$ is -A-Z, A is a bond, and Z is phenyl, optionally substituted with one to three $R^c$.

5. The compound of claim 1, or a pharmaceutically acceptable salt thereof wherein $X^t$ is $-CH_2-$.

6. The compound of claim 1, or a pharmaceutically acceptable salt thereof wherein $R^{1c}$, $R^7$ and $R^8$ are H, and $R^3$ is selected from the group consisting of F, Cl, $CH_3$, $CF_3$ and $OCH_3$.

7. The compound of claim 1, or a pharmaceutically acceptable salt thereof wherein a ring is formed between one pair of $R^4$ and $R^5$, $R^5$ and $R^6$, $R^{1b}$ and $R^{2b}$, or $R^{1a}$ and $R^{2a}$.

8. The compound of claim 1, or a pharmaceutically acceptable salt thereof wherein $R^5$ is -A-Z, and Z is selected from the group consisting of piperidinyl, imidazolyl and pyridinyl.

9. The compound of claim 1, or a pharmaceutically acceptable salt thereof wherein n is 0.

10. The compound of claim 1, or a pharmaceutically acceptable salt thereof wherein $R^4$ is selected from the group consisting of F, Cl, $CH_3$, $CF_3$ and $OCH_3$.

11. The compound of claim 1, or a pharmaceutically acceptable salt thereof wherein the group $R^{1a}$ is $OCH_3$ and $R^{1b}$ is F.

12. The compound of claim 1, or a pharmaceutically acceptable salt thereof wherein $R^{2a}$ and $R^{2b}$ are each H.

13. The compound of claim 1, or a pharmaceutically acceptable salt thereof wherein $R^{2a}$ and $R^{2b}$ are combined to form a 4- to 8-membered ring or spirocyclic ring, optionally having one or two additional ring vertices selected from O, N or S; wherein said ring or spirocyclic ring is substituted with 0 to 4 substituents independently selected from the group consisting of oxo, $C_{1-8}$ alkyl, $C_{1-8}$ haloalkyl, $C_{1-8}$ hydroxyalkyl, $-X^2-C(O)_2R^a$, $-X^2-OR^a$, $-X^2-NR^aR^b$, $-X^2-CONR^aR^b$, $-X^2-SO_2R^a$, $-X^2-SO_2NR^aR^b$, and $-X^2-SO_3R^a$; wherein $X^2$ is a bond or $C_{1-6}$ alkylene.

14. The compound of claim 1, or a pharmaceutically acceptable salt thereof wherein $R^{2a}$ is H or $C_{1-8}$ alkyl; and $R^{2b}$ is $-Y$ or $-X^1-Y$.

15. The compound of claim 14, or a pharmaceutically acceptable salt thereof wherein Y is selected from the group consisting of $C_{3-6}$ cycloalkyl and $C_{4-8}$ heterocyclyl, each of which is optionally further substituted with one to four substituents independently selected from the group consisting of oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO-C_{1-8}$ alkyl, and $CO_2H$.

16. The compound of claim 1, or a pharmaceutically acceptable salt thereof having the formula (Ia):

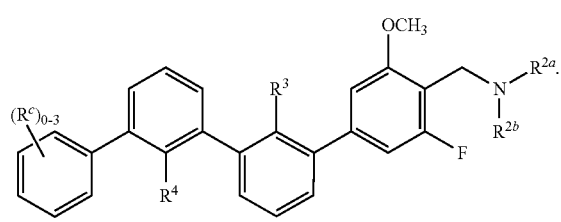
(Ia)

17. The compound of claim 1, or a pharmaceutically acceptable salt thereof having the formula (Ib):

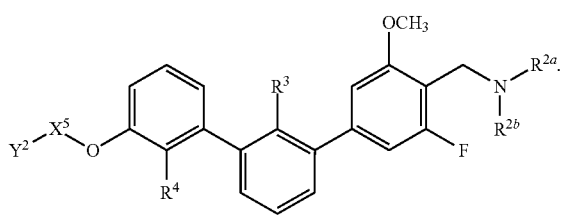
(Ib)

18. The compound of claim 1, or a pharmaceutically acceptable salt thereof having the formula (Ic):

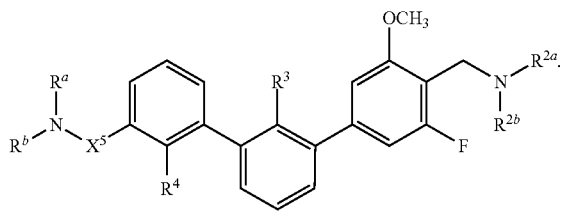
(Ic)

19. The compound of claim 17, or a pharmaceutically acceptable salt thereof wherein $Y^2$ is selected from the group consisting of:

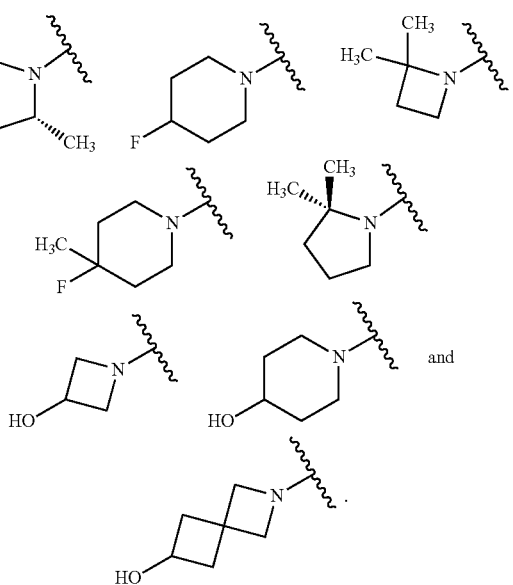

20. The compound of claim 1, or a pharmaceutically acceptable salt thereof, selected from the group consisting of

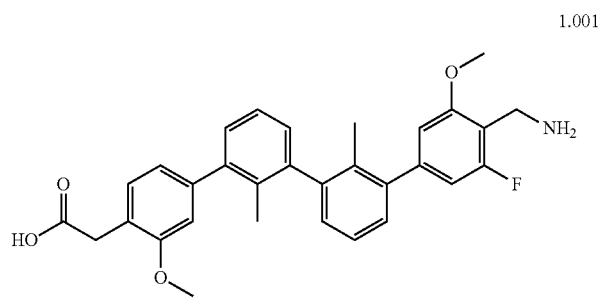
1.001

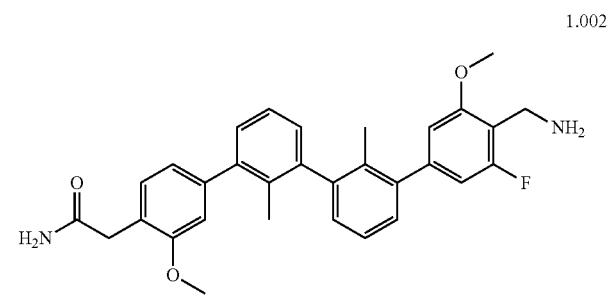
1.002

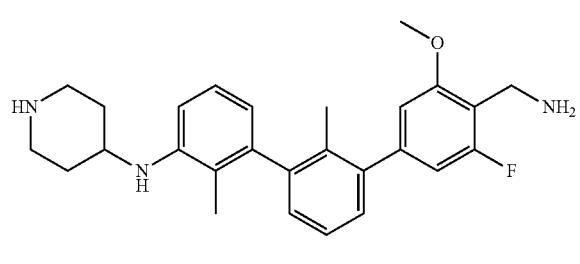
1.003

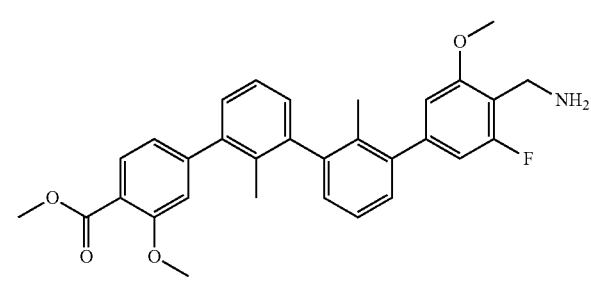
1.004

1.005 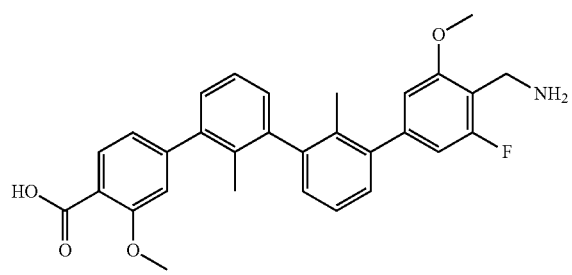
1.006 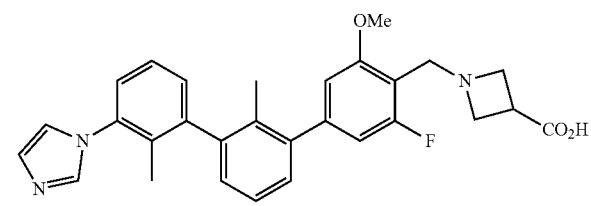
1.007 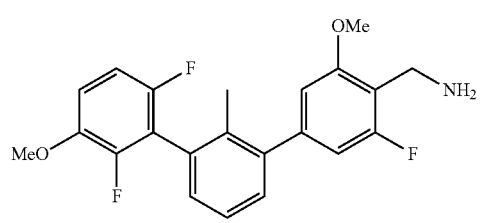
1.008 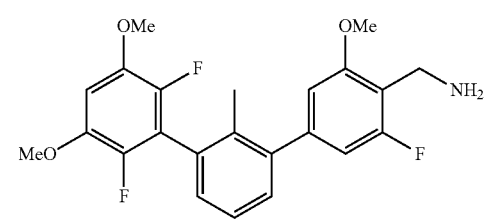
1.009 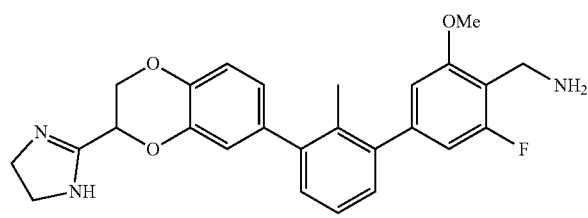
1.010 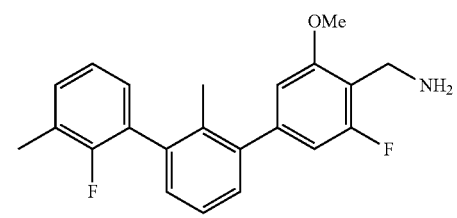
1.011 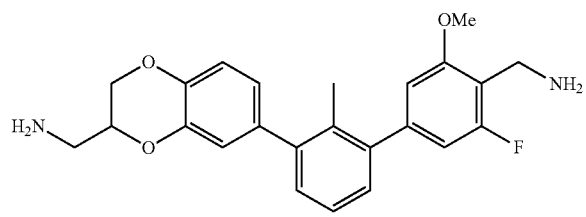
1.012 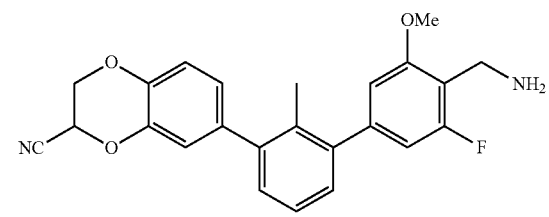
1.013 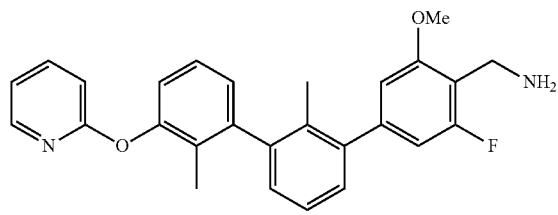
1.014 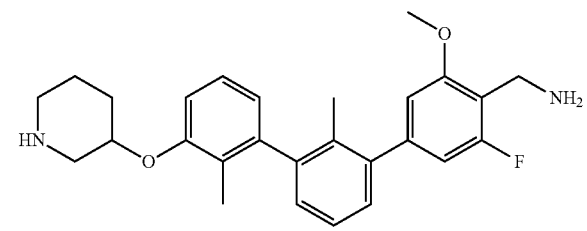
1.015 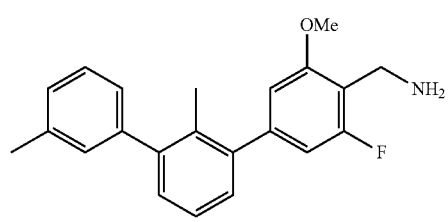
1.016 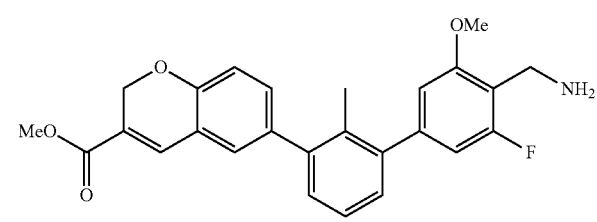

-continued
| 1.017 | 1.018 |
|---|---|
| 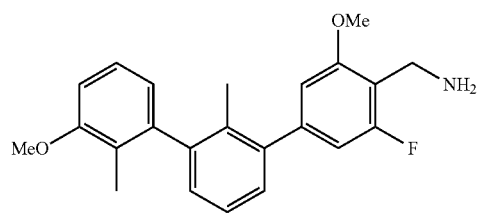 | 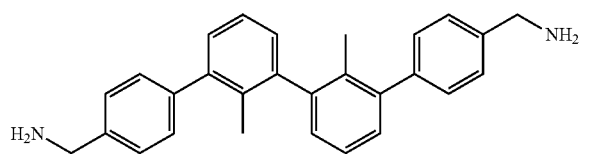 |
| 1.019 | 1.020 |
| 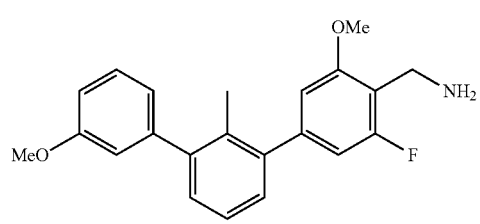 | 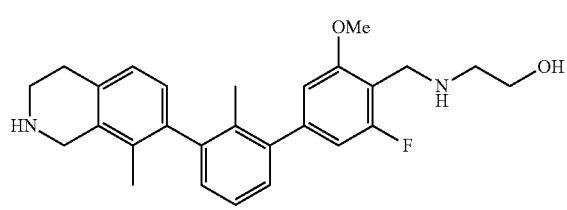 |
| 1.021 | 1.022 |
| 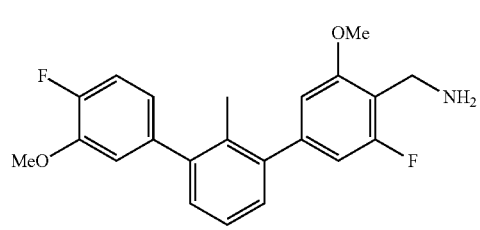 | 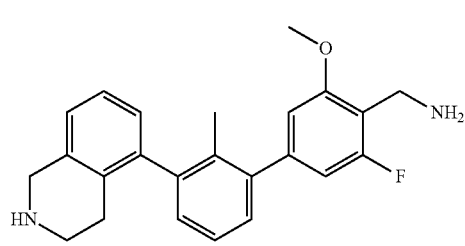 |
| 1.023 | 1.024 |
| 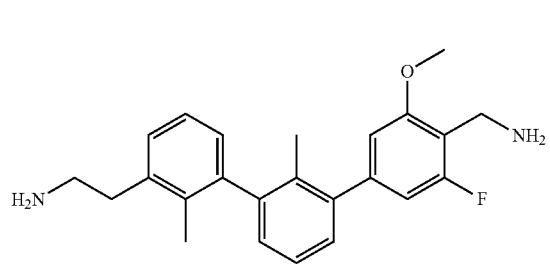 | 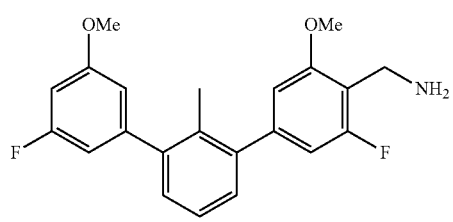 |
| 1.025 | 1.026 |
| 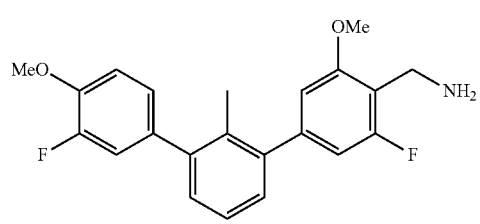 | 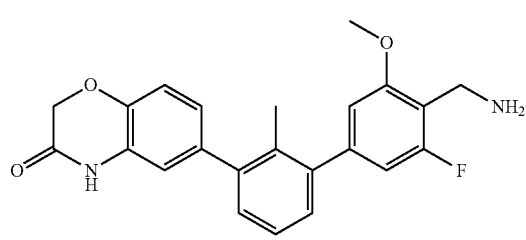 |
| 1.027 | 1.028 |
| 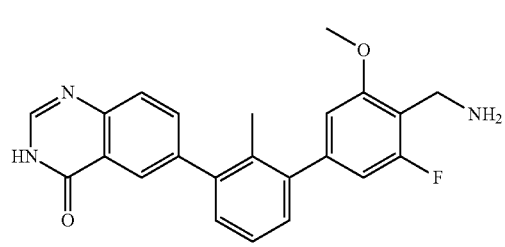 | 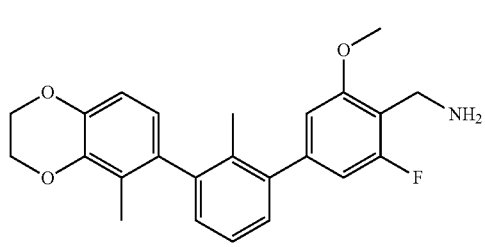 |
| 1.029 | 1.030 |
| 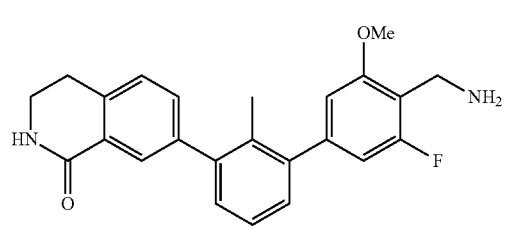 | 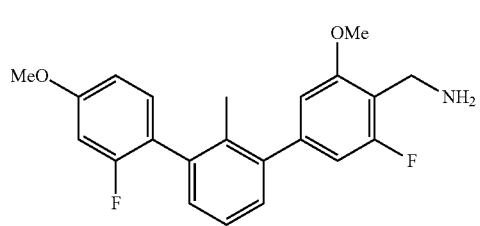 |

-continued
1.031
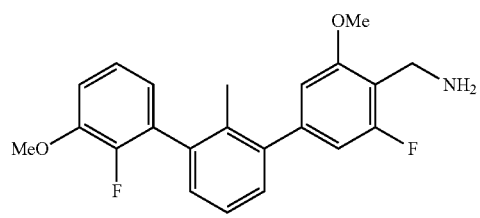
1.032
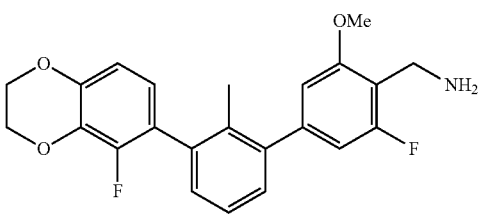
1.033
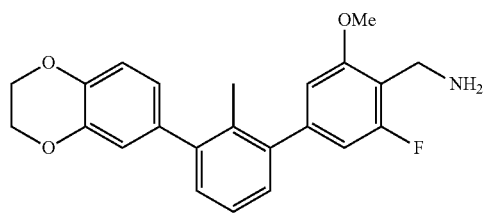
1.034
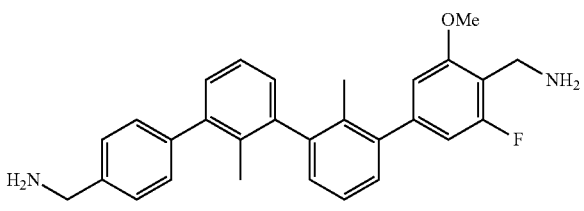
1.035
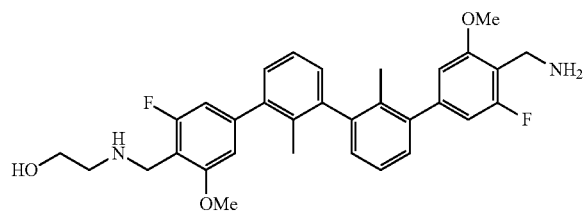
1.036
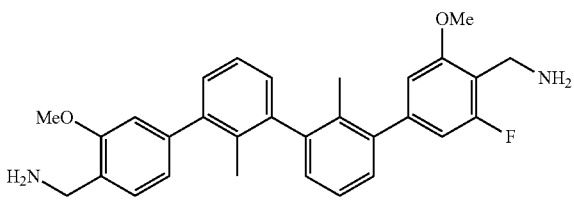
1.037
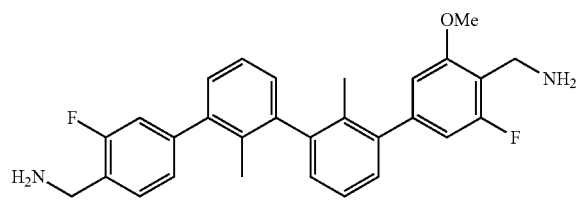
1.038
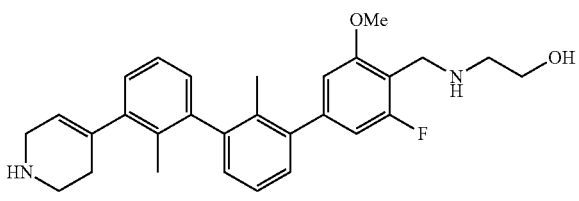
1.039
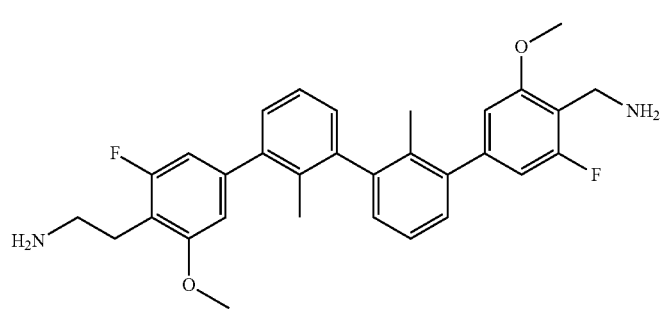
1.040
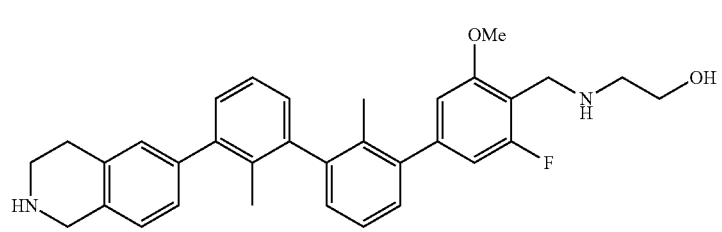

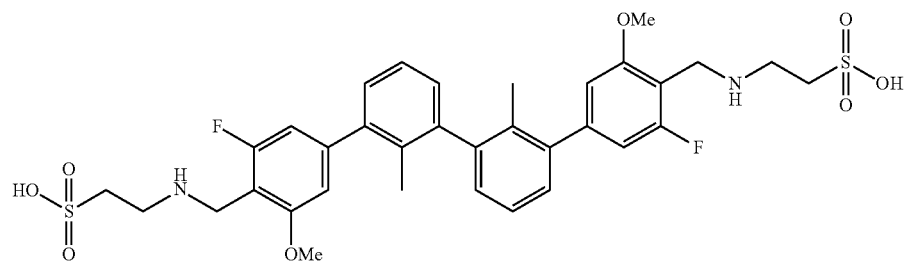
1.041
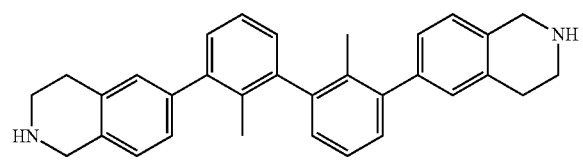
1.042
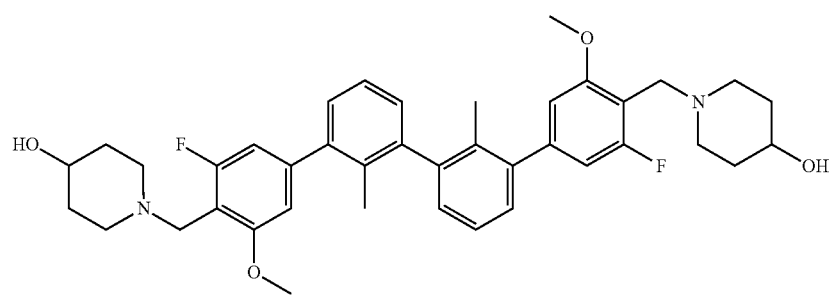
1.043
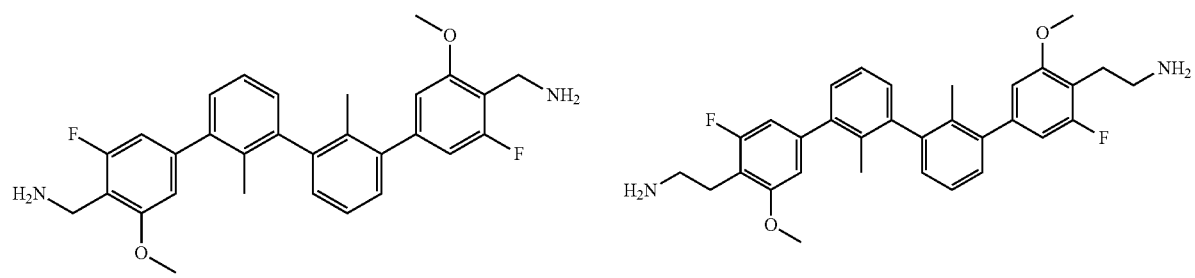
1.044
1.045
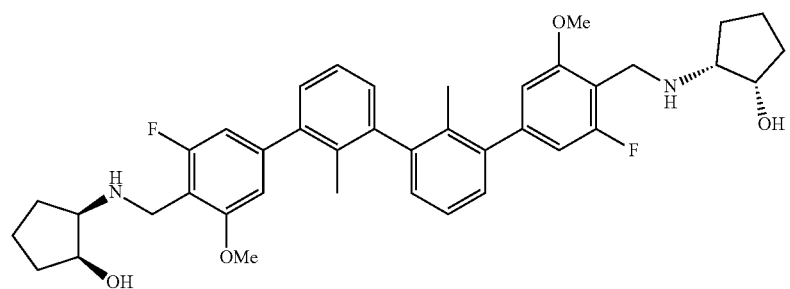
1.046
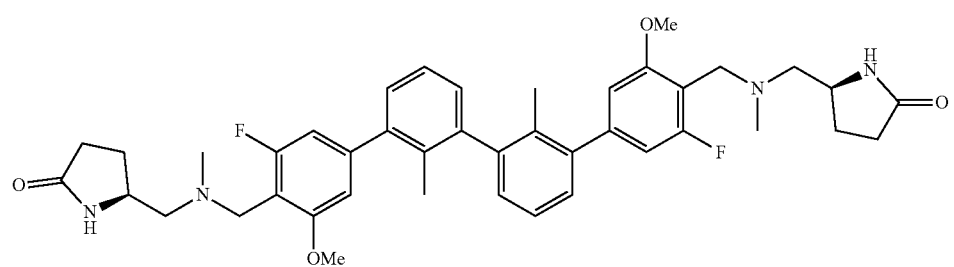
10.47

-continued
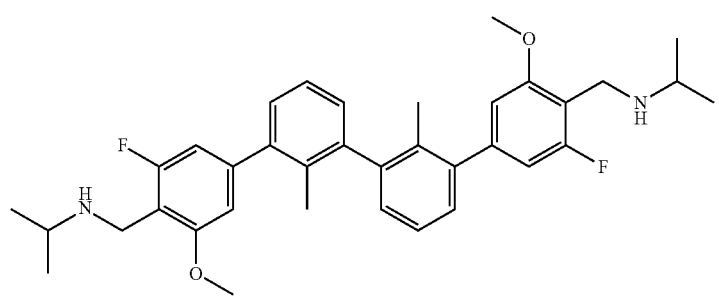
1.48
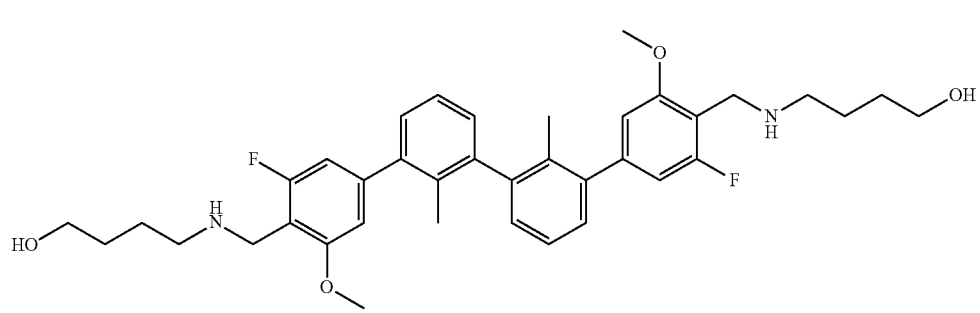
1.049
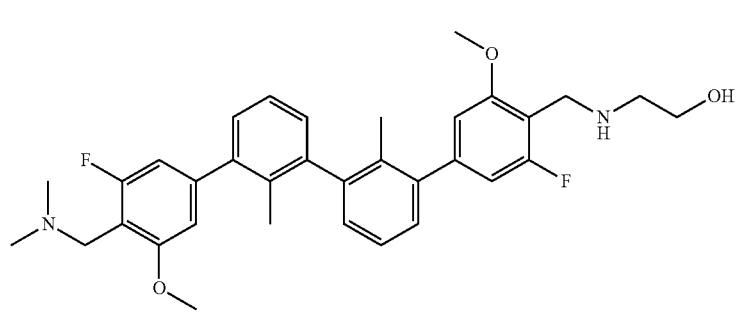
1.050
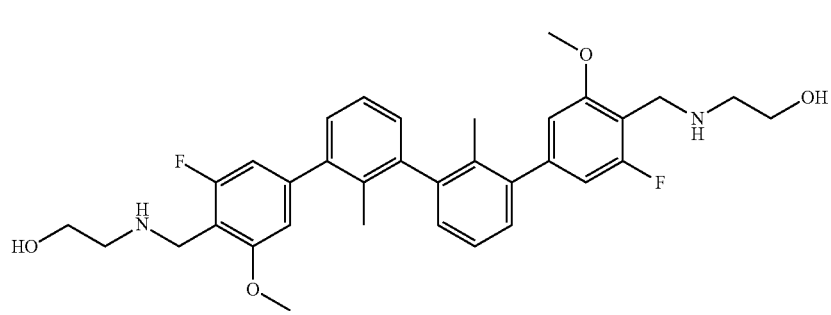
1.051
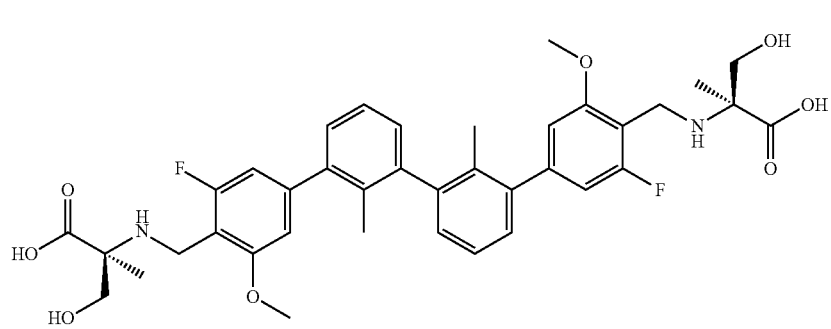
1.052

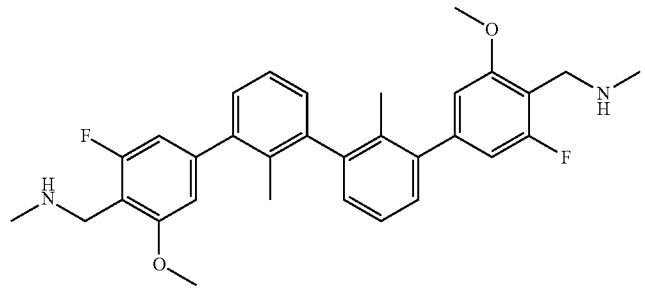
1.053
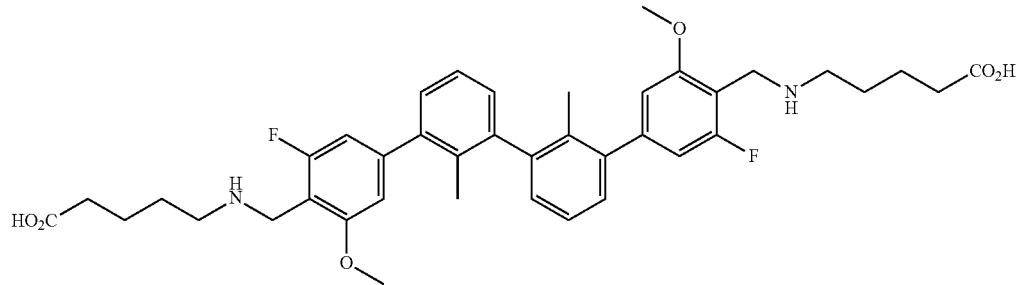
1.054
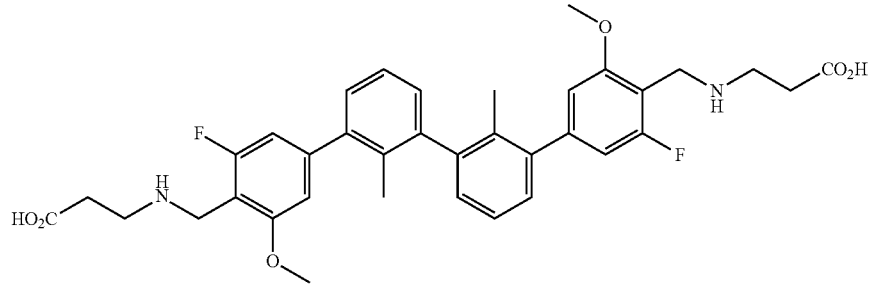
1.055
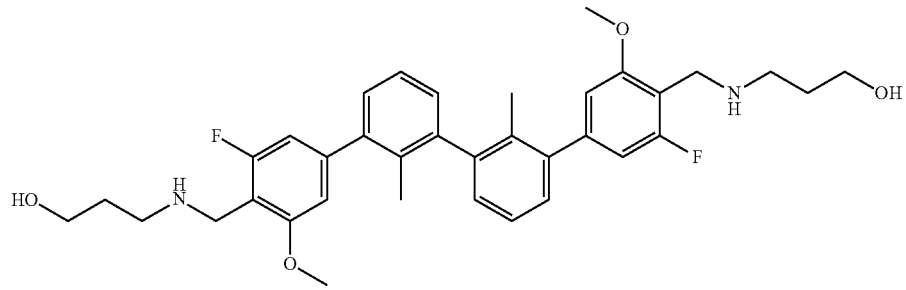
1.056
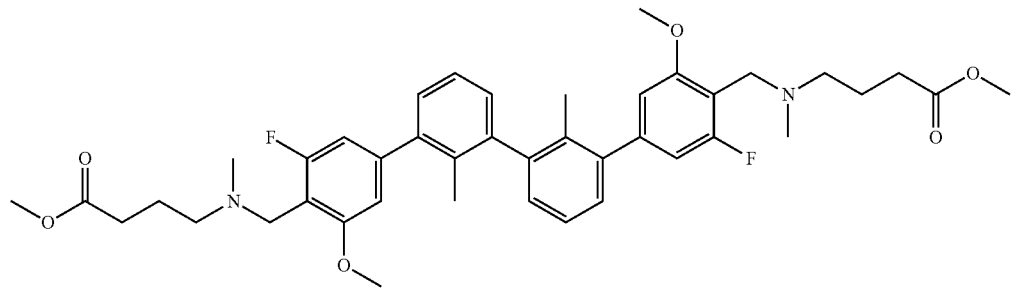
1.057

-continued
1.058
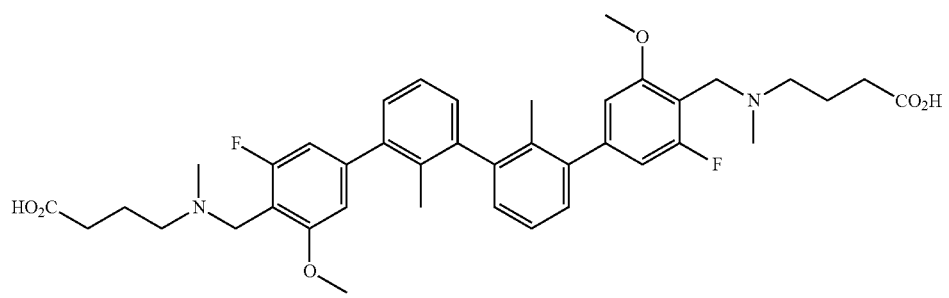
1.059
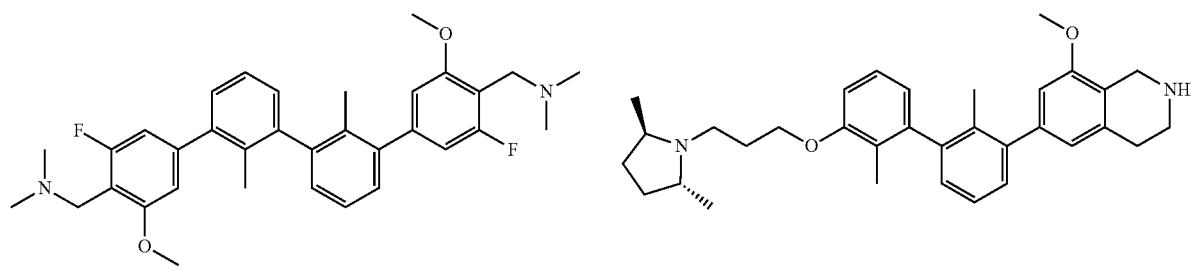
1.060
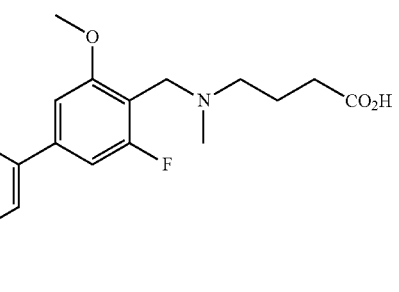
1.061
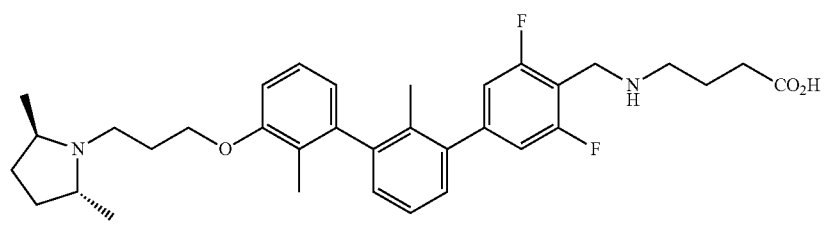
1.062
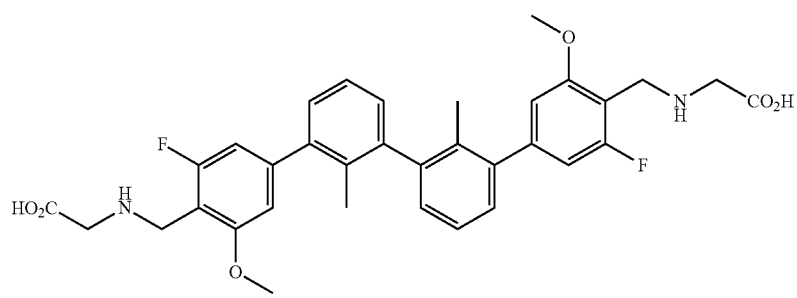
1.063
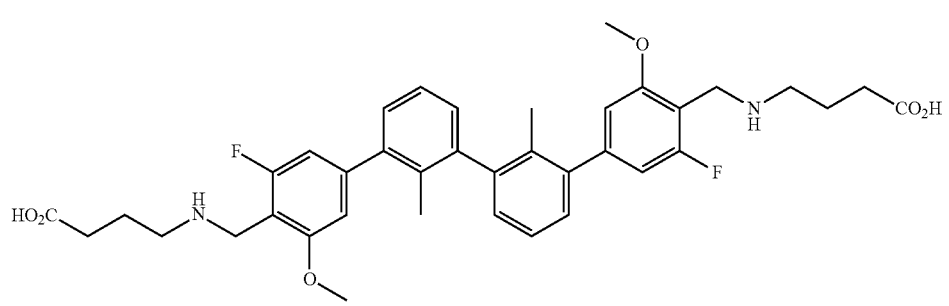
1.064
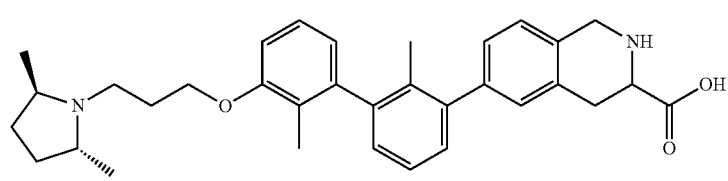

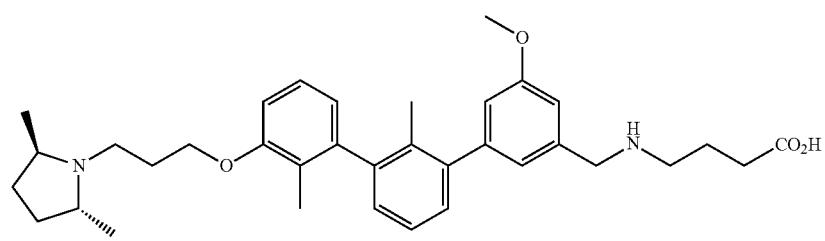
1.065
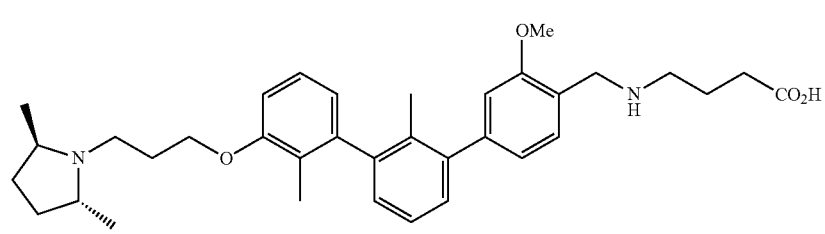
1.066
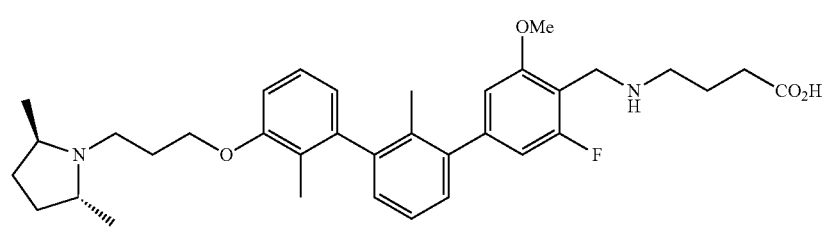
1.067
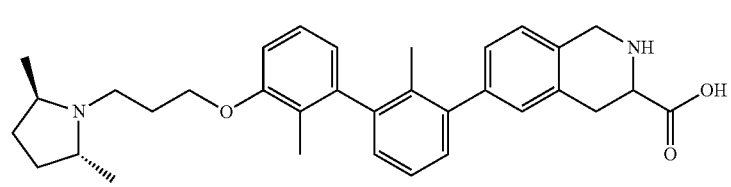
1.068
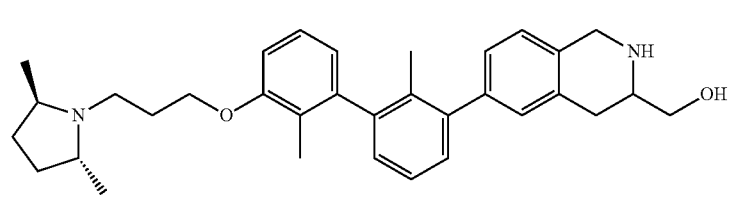
1.069
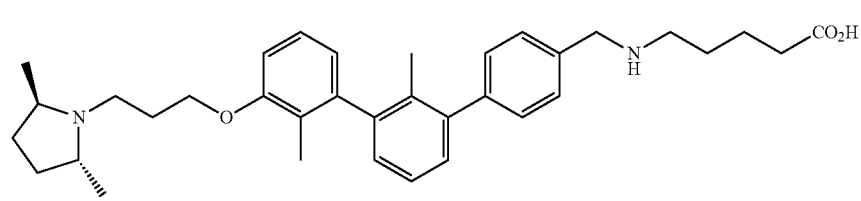
1.070
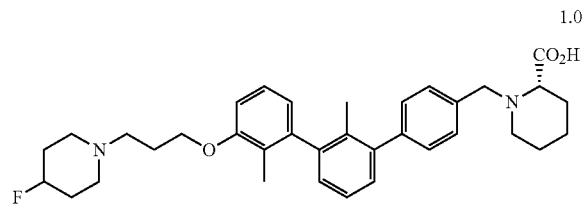
1.071
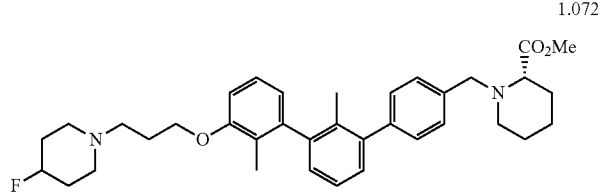
1.072

-continued
1.073
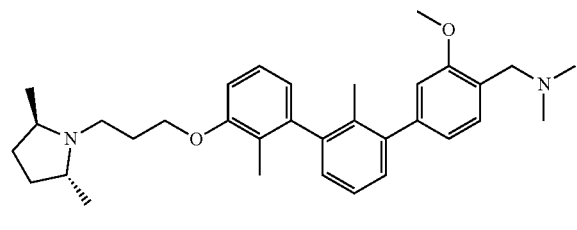
1.074
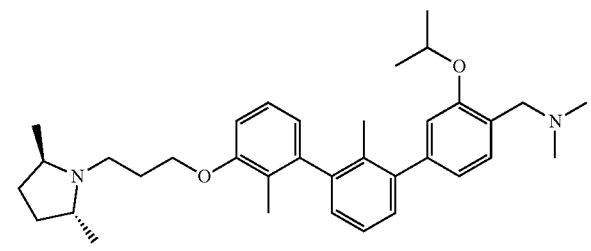
1.075
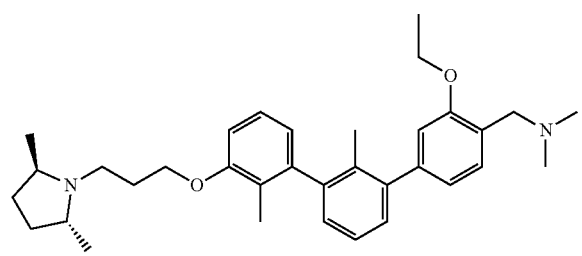
1.076
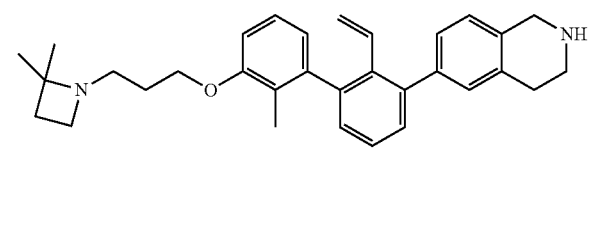
1.077
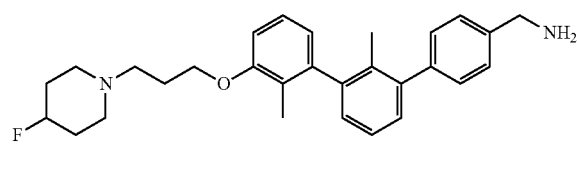
1.078
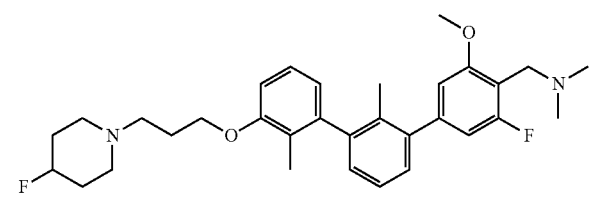
1.079
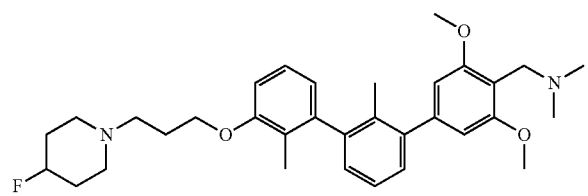
1.080
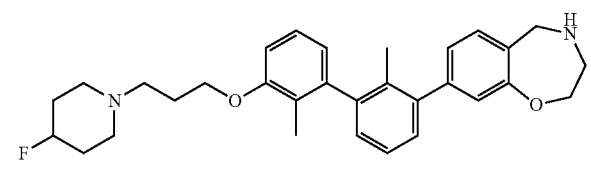
1.081
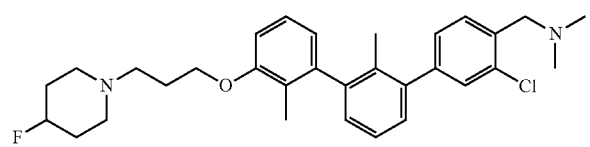
1.082
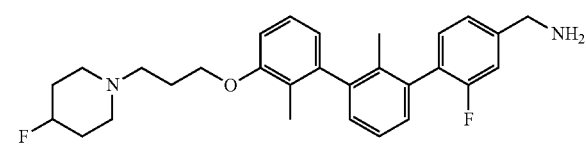
1.083
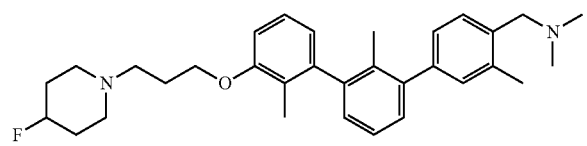
1.084
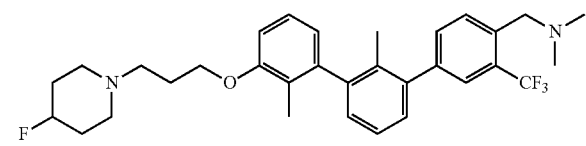
1.085
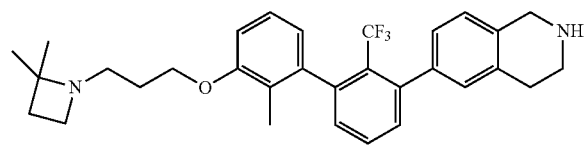
1.086
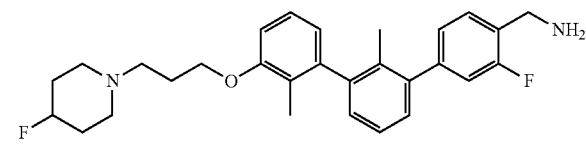

-continued
1.087
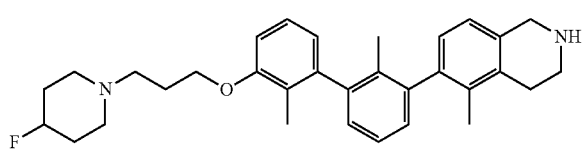
1.088
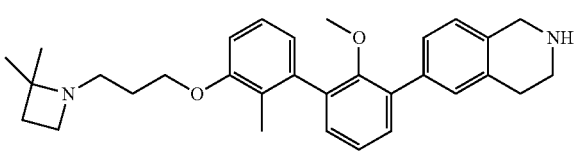
1.089
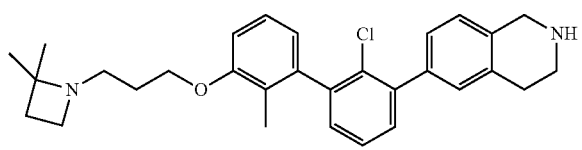
1.090
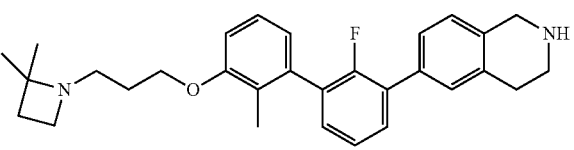
1.091
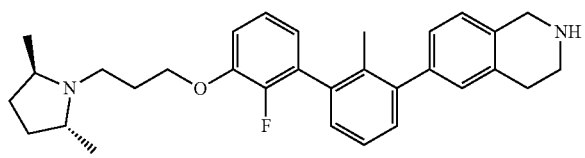
1.092
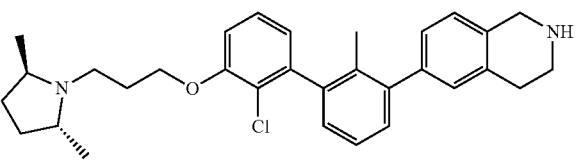
1.093
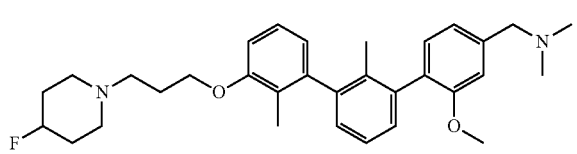
1.094
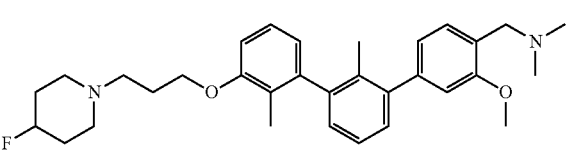
1.095
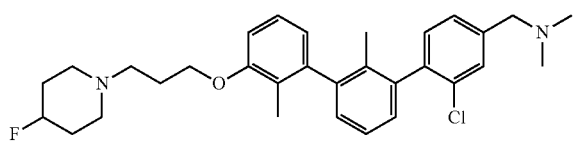
1.096
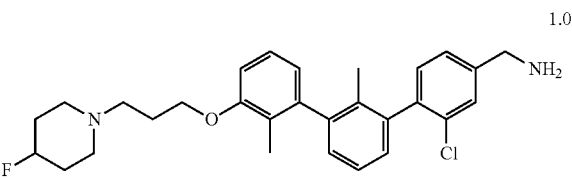
1.097
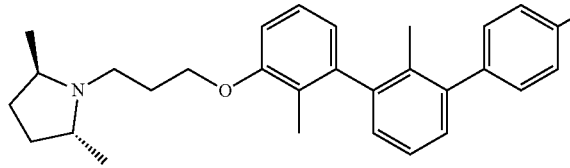
1.098
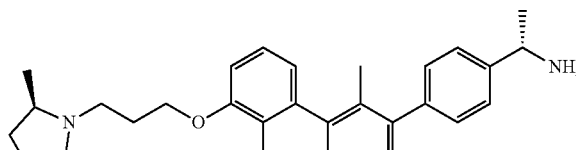
1.099
1.100
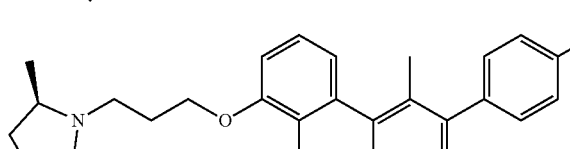
1.101
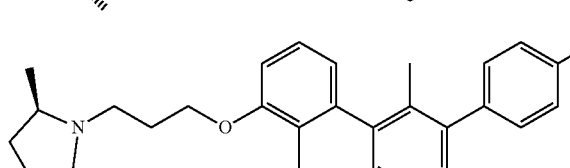

-continued
1.102
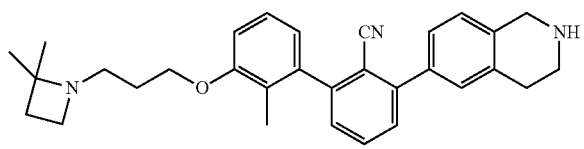
1.103
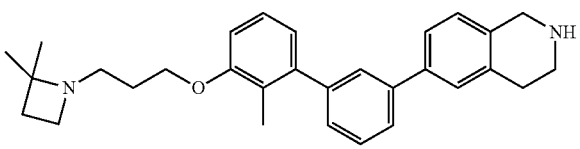
1.104
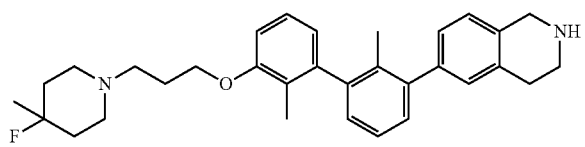
1.105
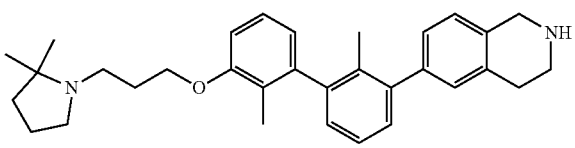
1.106
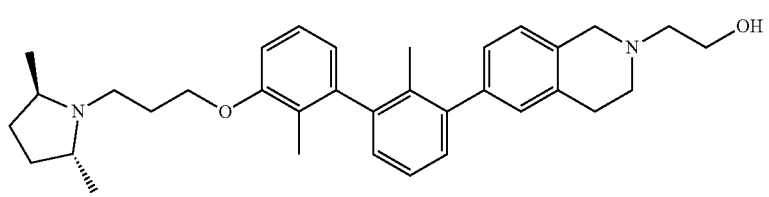
1.107
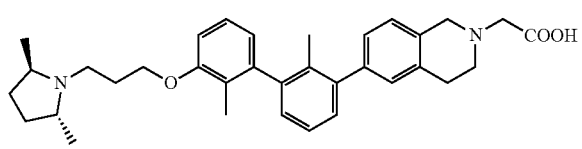
1.108
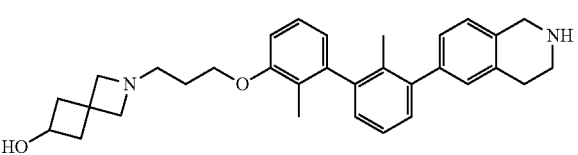
1.109
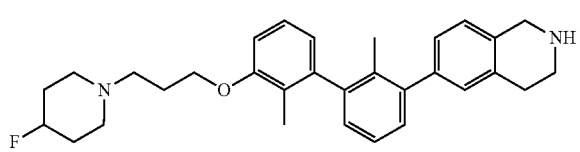
1.110
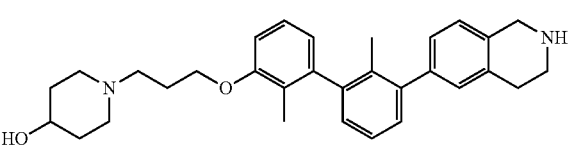
1.111
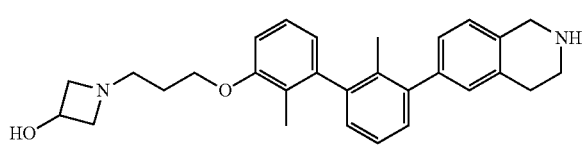
1.112
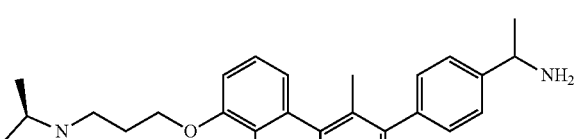
1.113
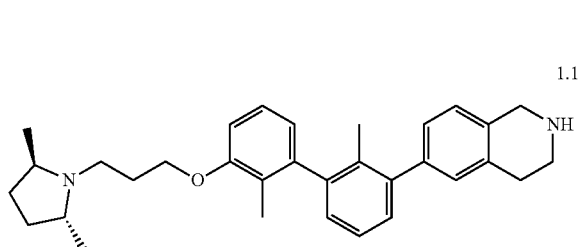
1.114
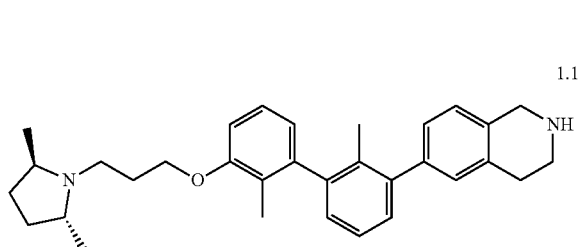
1.115
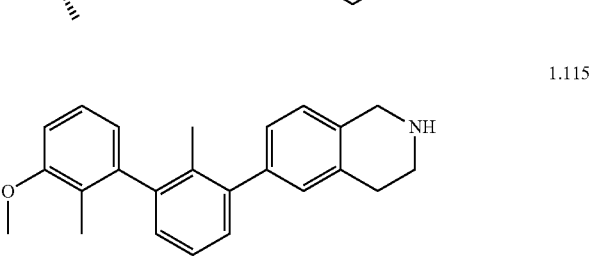

-continued
1.116 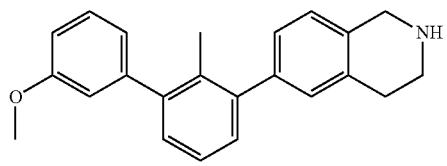 1.117 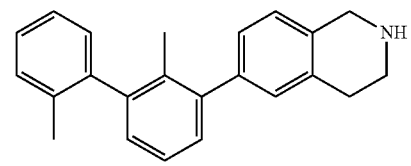
1.118 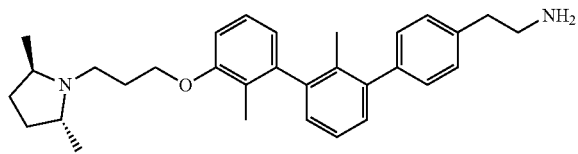 1.119 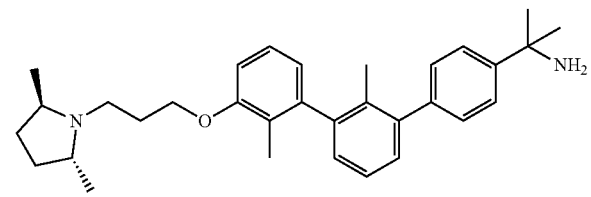
1.120 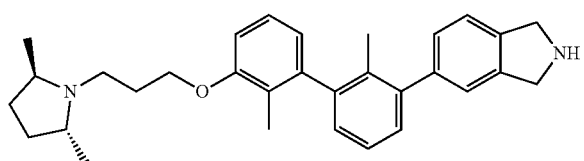 1.121 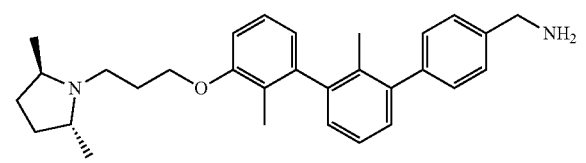
1.122 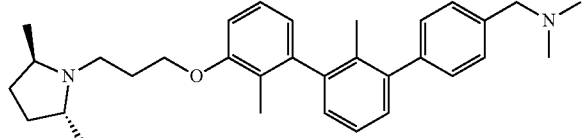 1.123 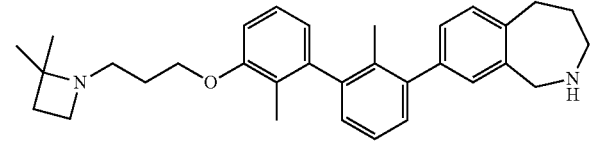
1.124 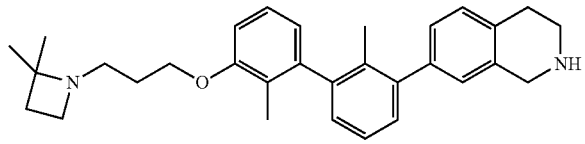 1.125 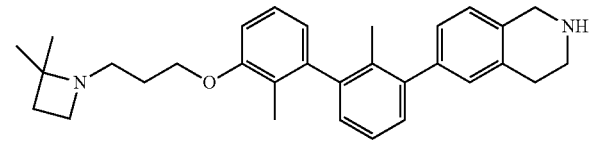
1.126 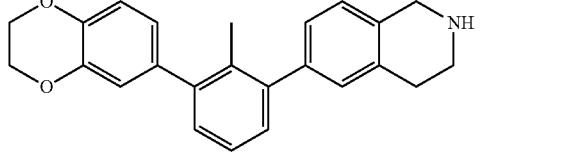 1.127 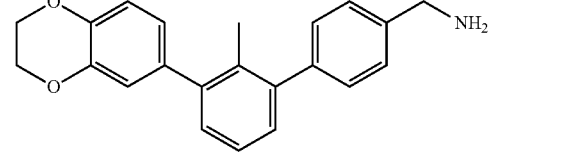
1.128 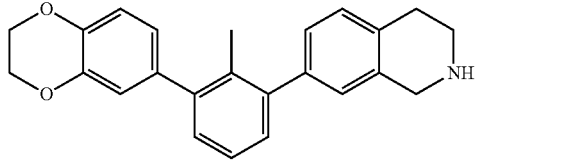
21. A pharmaceutical composition comprising a compound of claim 1, or a pharmaceutically acceptable salt thereof, and a pharmaceutically acceptable excipient.
* * * * *